US 7,896,804 B2

(12) United States Patent
Uchimura et al.

(10) Patent No.: US 7,896,804 B2
(45) Date of Patent: Mar. 1, 2011

(54) ENDOSCOPE WITH FIRST AND SECOND IMAGING AND ILLUMINATION UNITS

(75) Inventors: Sumihiro Uchimura, Sagamihara (JP); Akira Taniguchi, Hachioji (JP); Toshiaki Noguchi, Tachikawa (JP); Fumiyuki Onoda, Tama (JP); Katsuya Suzuki, Sagamihara (JP)

(73) Assignee: Olympus Corporation, Tokyo (JP)

( * ) Notice: Subject to any disclaimer, the term of this patent is extended or adjusted under 35 U.S.C. 154(b) by 1220 days.

(21) Appl. No.: 11/510,830

(22) Filed: Aug. 25, 2006

(65) Prior Publication Data

US 2006/0293565 A1  Dec. 28, 2006

Related U.S. Application Data

(63) Continuation of application No. PCT/JP2005/003036, filed on Feb. 24, 2005.

(30) Foreign Application Priority Data

Feb. 27, 2004  (JP)  ............................. 2004-054678
Apr. 6, 2004  (JP)  ............................. 2004-112329

(51) Int. Cl.
  *A61B 1/05*  (2006.01)
  *A61B 1/012*  (2006.01)
  *A61B 1/06*  (2006.01)

(52) U.S. Cl. ................ 600/173; 600/156; 600/129; 600/179; 600/118; 600/131; 600/144

(58) Field of Classification Search ............ 600/117, 600/118, 173, 160, 179, 129, 178, 153, 156, 600/131, 141
See application file for complete search history.

(56) References Cited

U.S. PATENT DOCUMENTS

| | | | | | |
|---|---|---|---|---|---|
| 3,918,438 | A | * | 11/1975 | Hayamizu et al. | 600/168 |
| 4,204,528 | A | * | 5/1980 | Termanini | 600/109 |
| 4,319,563 | A | * | 3/1982 | Kubota | 600/129 |
| 4,667,230 | A | * | 5/1987 | Arakawa et al. | 348/76 |
| 4,996,975 | A | * | 3/1991 | Nakamura | 600/118 |
| 5,489,256 | A | * | 2/1996 | Adair | 600/133 |
| 5,494,483 | A | * | 2/1996 | Adair | 600/111 |
| 5,630,782 | A | * | 5/1997 | Adair | 600/133 |
| 5,728,044 | A | * | 3/1998 | Shan | 600/145 |
| 5,749,830 | A | * | 5/1998 | Kaneko et al. | 600/160 |
| 5,830,121 | A | * | 11/1998 | Enomoto et al. | 600/117 |
| 5,871,440 | A | * | 2/1999 | Okada | 600/129 |
| 5,873,814 | A | * | 2/1999 | Adair | 600/109 |
| 5,940,126 | A | * | 8/1999 | Kimura | 348/294 |
| 5,951,462 | A | * | 9/1999 | Yamanaka | 600/118 |
| 5,957,833 | A | * | 9/1999 | Shan | 600/117 |
| 6,099,465 | A | * | 8/2000 | Inoue | 600/134 |
| 6,142,932 | A | * | 11/2000 | Morizumi | 600/166 |

(Continued)

FOREIGN PATENT DOCUMENTS

EP  1 099 405 A1  5/2003

(Continued)

*Primary Examiner*—John P Leubecker
(74) *Attorney, Agent, or Firm*—Scully, Scott, Murphy & Presser, P.C.

(57) ABSTRACT

First and second illumination and image pickup units are provided in the container body having opposite reference view field directions and are respectively freely tilted in an arbitrary direction within predetermined inclination angles from the reference view field direction.

22 Claims, 38 Drawing Sheets

U.S. PATENT DOCUMENTS

| | | | |
|---|---|---|---|
| 6,398,725 B1 * | 6/2002 | Thompson | 600/173 |
| 6,436,032 B1 | 8/2002 | Eto et al. | |
| 6,641,529 B2 * | 11/2003 | Kuranishi | 600/160 |
| 6,902,527 B1 * | 6/2005 | Doguchi et al. | 600/109 |
| 2002/0198439 A1 | 12/2002 | Mizuno | |
| 2003/0069475 A1 | 4/2003 | Banik et al. | |
| 2003/0076411 A1 | 4/2003 | Iida et al. | |
| 2003/0093088 A1 * | 5/2003 | Long et al. | 606/129 |
| 2003/0125788 A1 * | 7/2003 | Long | 607/133 |
| 2003/0130562 A1 * | 7/2003 | Barbato et al. | 600/109 |
| 2003/0174208 A1 | 9/2003 | Glukhovsky et al. | |
| 2003/0213495 A1 | 11/2003 | Fujita et al. | |
| 2004/0143157 A1 | 7/2004 | Doguchi et al. | |
| 2004/0215059 A1 | 10/2004 | Homan et al. | |
| 2004/0215061 A1 * | 10/2004 | Kimmel et al. | 600/179 |

FOREIGN PATENT DOCUMENTS

| | | |
|---|---|---|
| EP | 1 310 207 A2 | 5/2003 |
| EP | 1 326 432 A2 | 7/2003 |
| JP | 05-237056 | 9/1993 |
| JP | 06-285043 | 10/1994 |
| JP | 11-072431 | 3/1999 |
| JP | 11-225966 | 8/1999 |
| JP | 2000-217780 | 8/2000 |
| JP | 2000-342522 | 12/2000 |
| JP | 2001-029313 | 2/2001 |
| JP | 2001-046326 | 2/2001 |
| JP | 2001-137182 | 5/2001 |
| JP | 2001-224551 | 8/2001 |
| JP | 2002-153419 | 5/2002 |
| JP | 2002-209839 | 7/2002 |
| JP | 2002-354300 | 12/2002 |
| JP | 2003-070728 | 3/2003 |
| JP | 2003-135388 | 5/2003 |
| JP | 2003-180631 | 7/2003 |
| JP | 2003-204909 | 7/2003 |
| JP | 2003-265405 | 9/2003 |
| JP | 2003-299613 | 10/2003 |
| JP | 2003-325439 | 11/2003 |
| JP | 2004-000640 | 1/2004 |
| JP | 2004-016504 | 1/2004 |
| WO | WO00/69324 | 11/2000 |

* cited by examiner

WIRED METHOD

OPTICAL COMMUNICATION METHOD

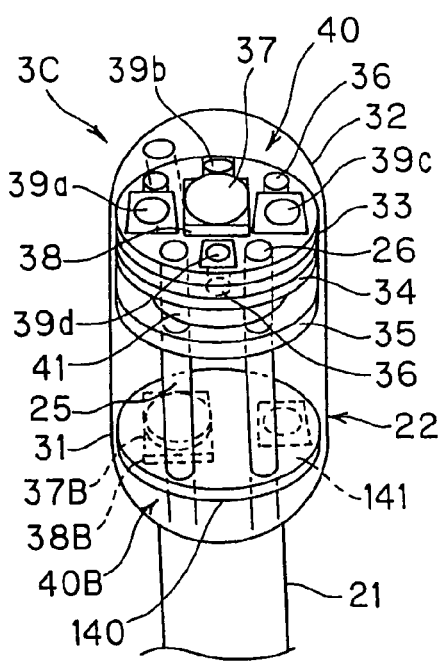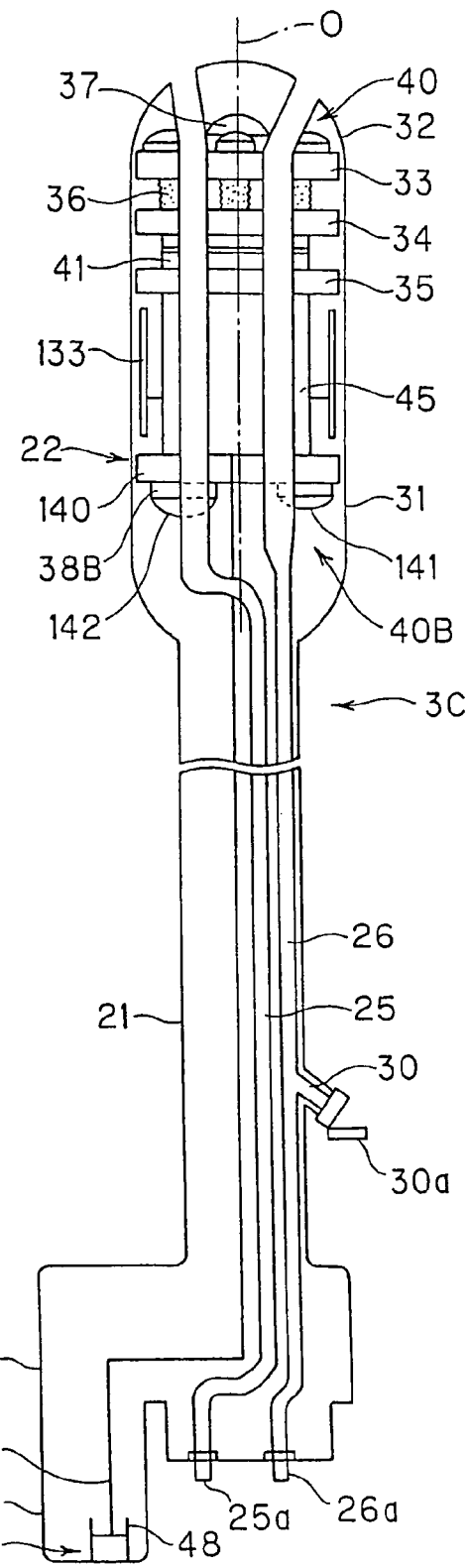

FIG.27A
FIG.27B
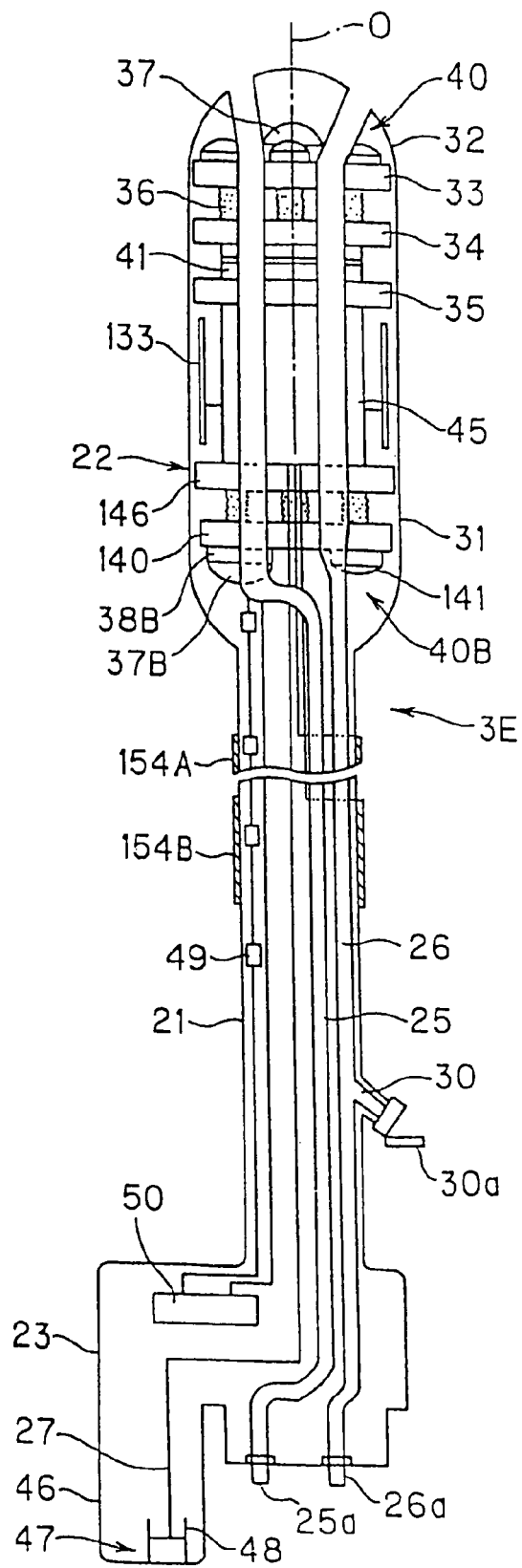
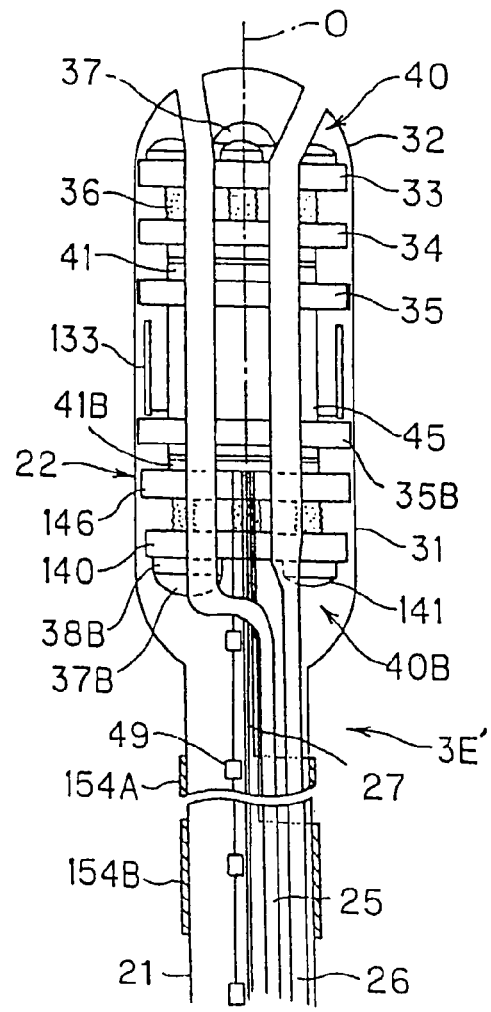

FIG.30A
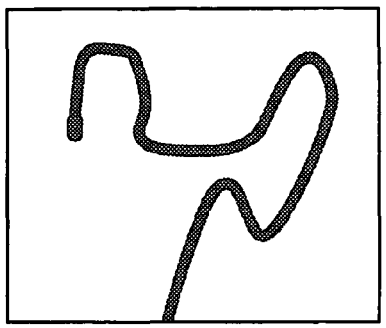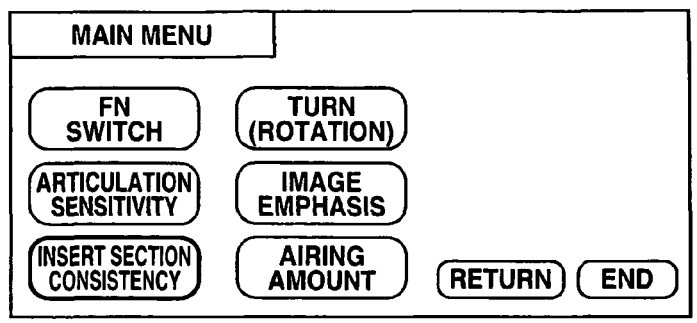
FIG.30B
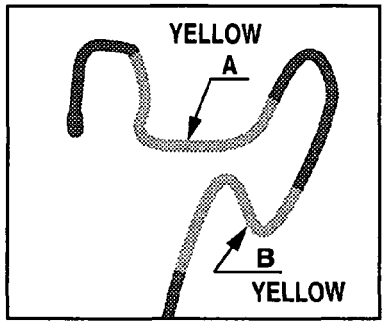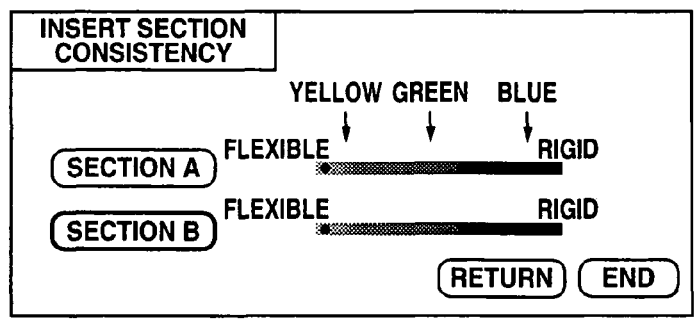
FIG.30C
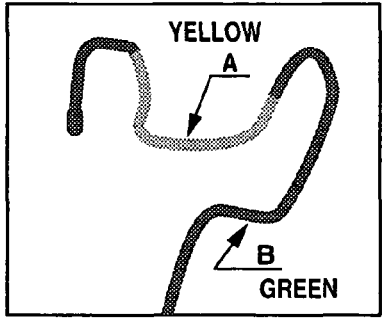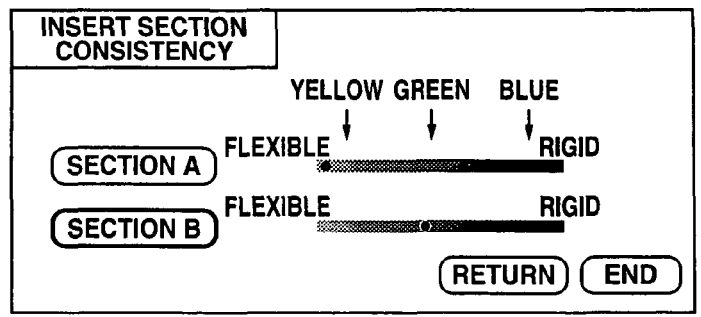
FIG.30D
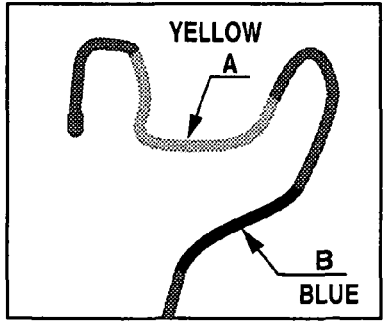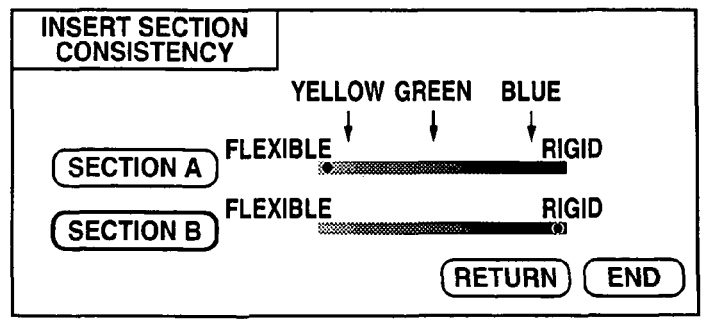

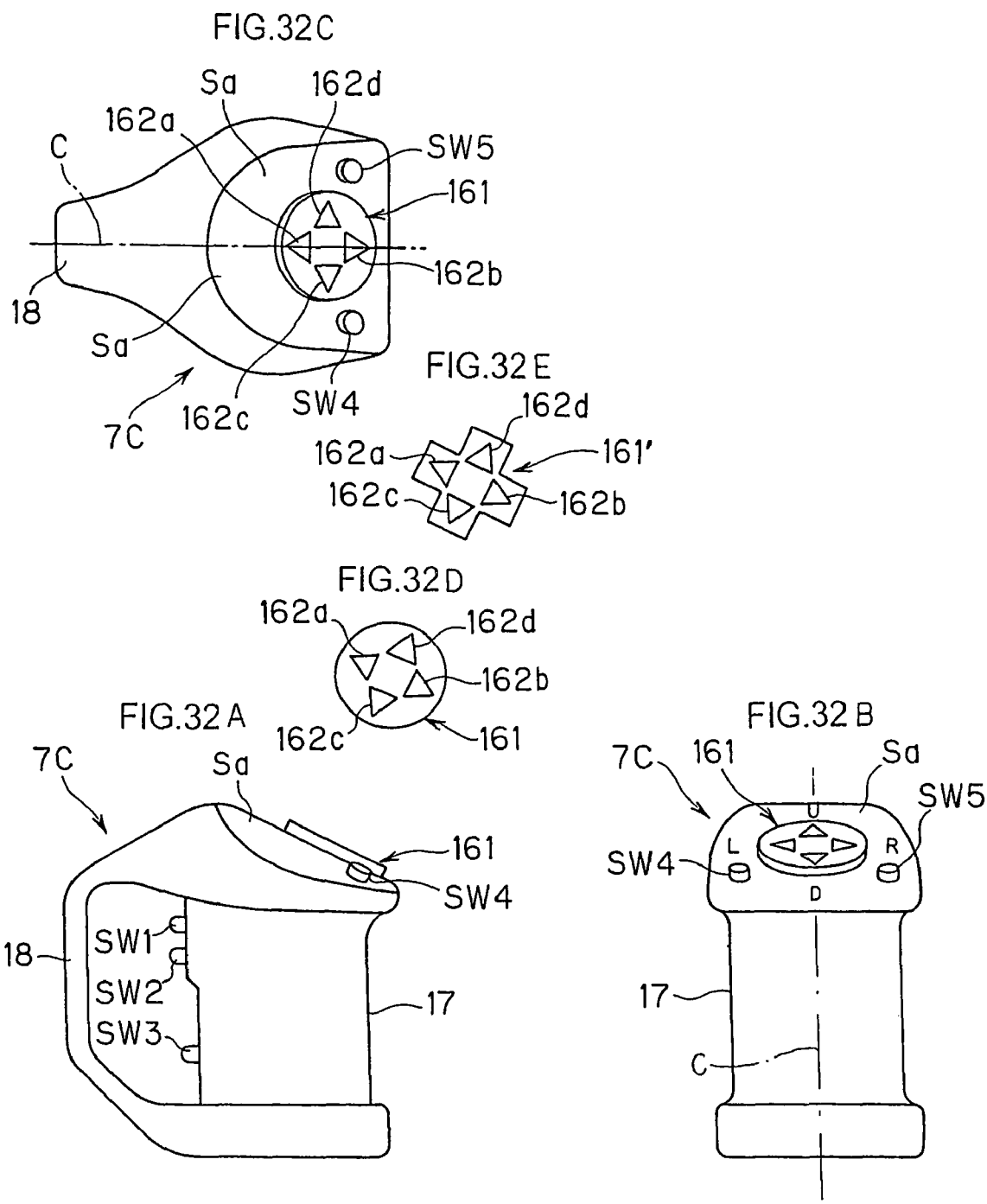

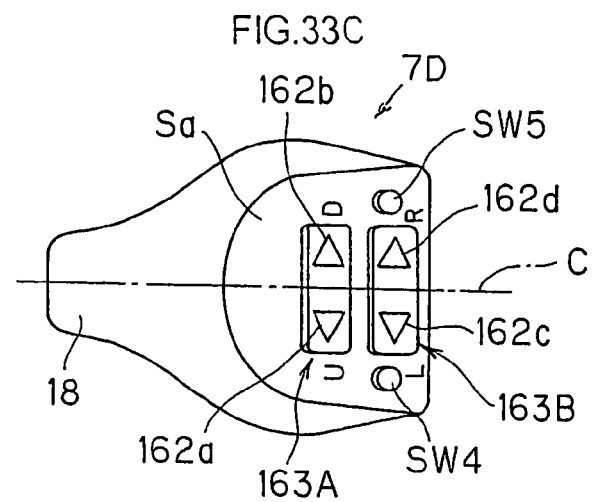
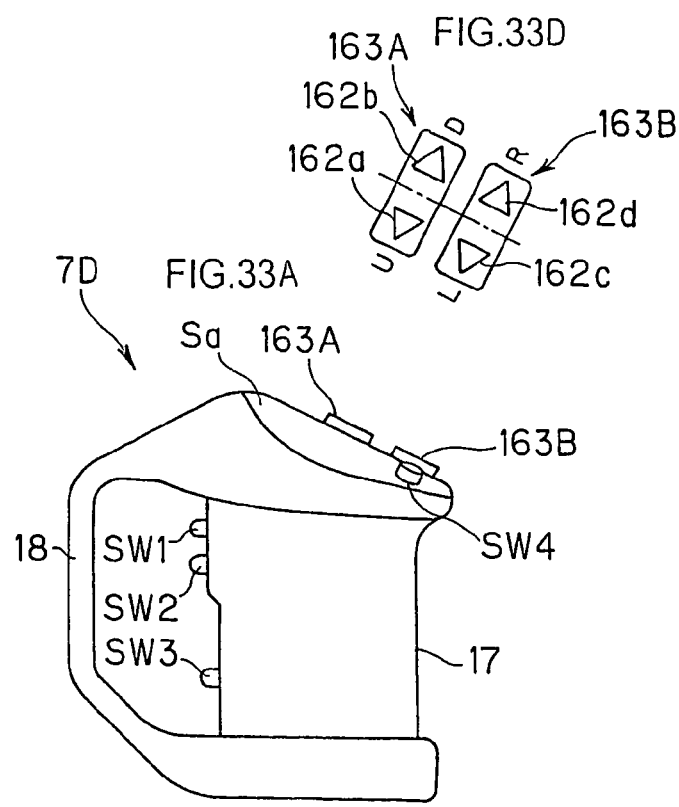
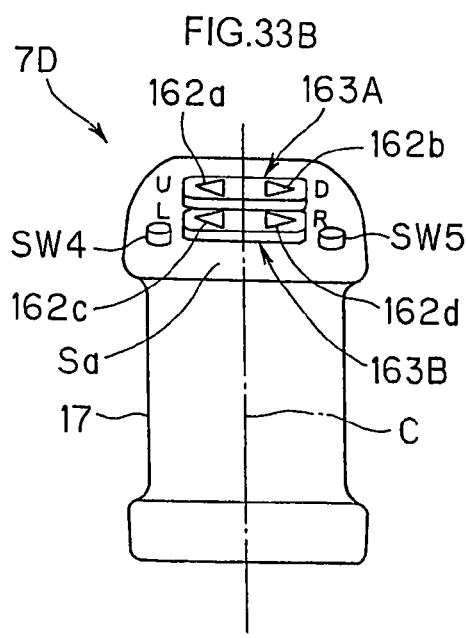

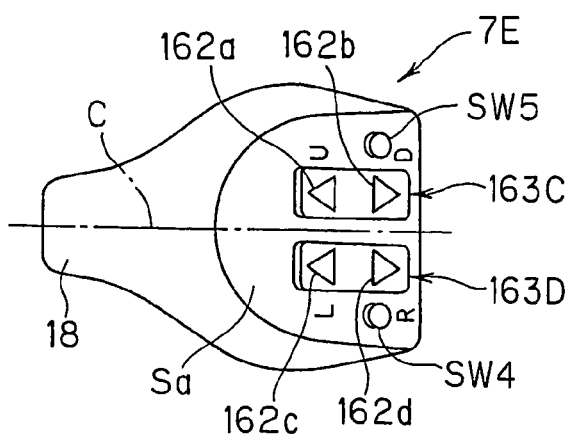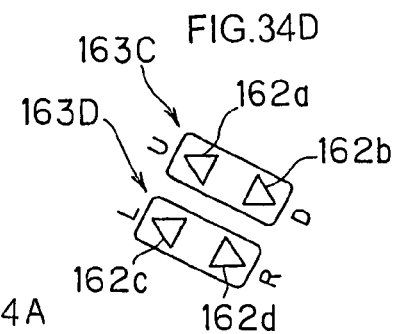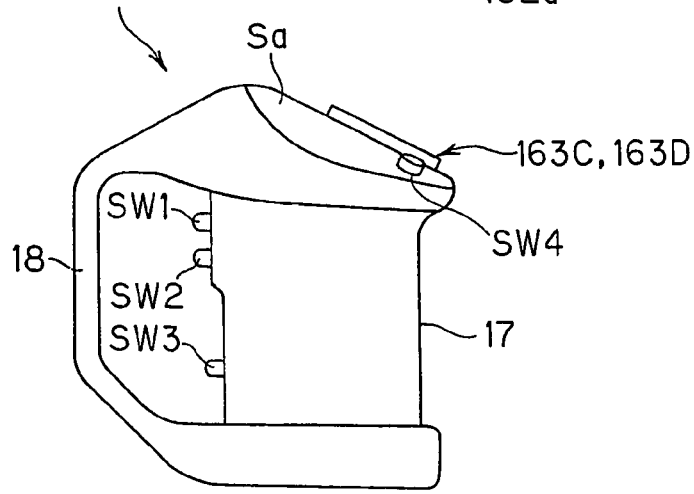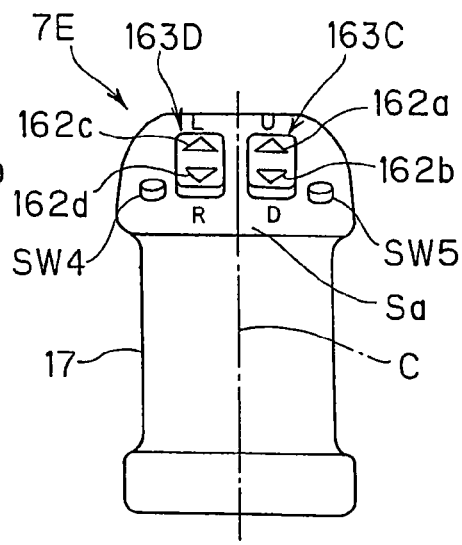

ENDOSCOPE WITH FIRST AND SECOND IMAGING AND ILLUMINATION UNITS

CROSS REFERENCES TO RELATED APPLICATIONS

This application is a continuation application of PCT/JP2005/003036 filed on Feb. 24, 2005 and claims benefit of Japanese Applications No. 2004-054678 filed in Japan on Feb. 27, 2004 and No. 2004-112329 filed in Japan on Apr. 6, 2004, the entire contents of each of which are incorporated herein by their reference.

BACKGROUND OF THE INVENTION

1. Field of the Invention

The present invention relates to an endoscope for performing an endoscopy in a body cavity or the like.

2. Description of the Related Art

In recent years, endoscopes are widely used in a medical field and an industrial field. Also, these days, a capsule endoscope having a capsule shape has been proposed. A user takes the capsule endoscope from the mouse or the like, and endoscopy can be relatively easily performed inside the body.

Meanwhile, Japanese Unexamined Patent Application Publication No. 2003-135388 discloses a capsule endoscope with a purpose of being placed inside the body.

In the prior art disclosed in this publication, while introduced into the body by an endoscope, at a location for placement, a balloon provided at an outer circumference of a capsule endoscope is supplied with a fluid and then expanded, whereby the capsule endoscope is separated and thus placed.

A capsule endoscope of a prior art generally includes an illumination section and an observation section in a capsule shaped container, as disclosed in Japanese Unexamined Patent Application Publication No. 11-225966, for example. Such a capsule endoscope of the prior art has no function of changing a direction of view in the observation by bending an insert section like an endoscope having an elongated insert section.

It should be noted that Japanese Unexamined Patent Application Publication No. 2000-342522 discloses a swallowable endoscope having an elongated tube shape. This endoscope has bending, and thus the direction of view can be set variable.

SUMMARY OF THE INVENTION

The endoscope according to an aspect of the present invention includes: a container body; an illumination section and an image pickup section provided to the container body; an elongated flexible tube body integrally provided to the container body; and a hollow duct line passing through the flexible tube body, a distal end of which penetrates through the container body with an opening formed on an outer surface of the container body.

The endoscope according to another aspect of the present invention includes a container body; an illumination section and an observation section provided to the container body; and a view field direction varying section provided in the container body for varying a view field direction of the observation section.

BRIEF DESCRIPTION OF THE DRAWINGS

FIG. 23A shows an entire structure of an endoscope according to a third embodiment of the present invention;

FIG. 23B shows a structure of the endoscope at the distal end according to the third embodiment of the present invention;

FIG. 27A shows an entire structure of an endoscope according to a fifth embodiment of the present invention;

FIG. 27B shows a structure of a part of the endoscope according to a modification example of the fifth embodiment of the present invention;

FIGS. 30A to 30D are explanatory diagrams of a setting operation of consistency varying and the like;

FIGS. 32A to 32E show a first modification example of the operation remote controller and the like;

FIGS. 33A to 33D show a second modification example of the operation remote controller and the like;

FIGS. 34A to 34D show a third modification example of the operation remote controller and the like.

DESCRIPTION OF THE PREFERRED EMBODIMENTS

Hereinafter, preferred embodiments of the present invention will be described with reference to the drawings.

First Embodiment

A description will be given of a first embodiment of the present invention with reference to FIGS. 1 to 18.

Figure 1:
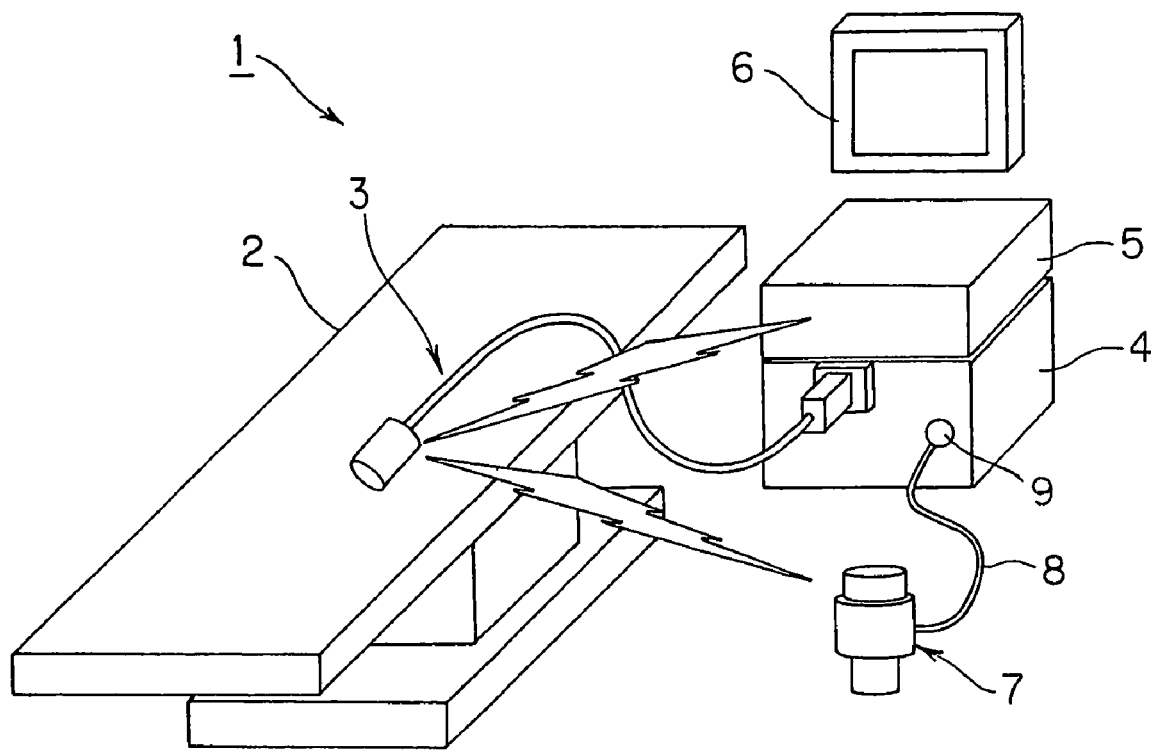
FIG. 1 is a schematic entire structure diagram of an endoscopic system according to a first embodiment of the present invention.

As shown in FIG. 1, an endoscopic system 1 according to the first embodiment of the present invention includes an endoscope 3 for inspecting a body cavity of a patient (not shown in the drawing) lying on an inspection bed 2, an air water supply/suction unit for performing airing, watering, and suction (abbreviated as AWS unit) 4 to which the endoscope 3 is detachably connected, an endoscopic system control device 5 for performing a control process for the endoscope 3 or the like, an observation monitor 6 for displaying an endoscopic image or the like generated by the endoscopic system control device 5, and an operation remote control unit for performing various remote operations for the endoscope 3 and the like (abbreviated as operation remote controller) 7. The operation remote controller 7 is detachably connected, for example, to a connector 9 of the AWS unit 4 via a connection cable 8.

Figure 2A:
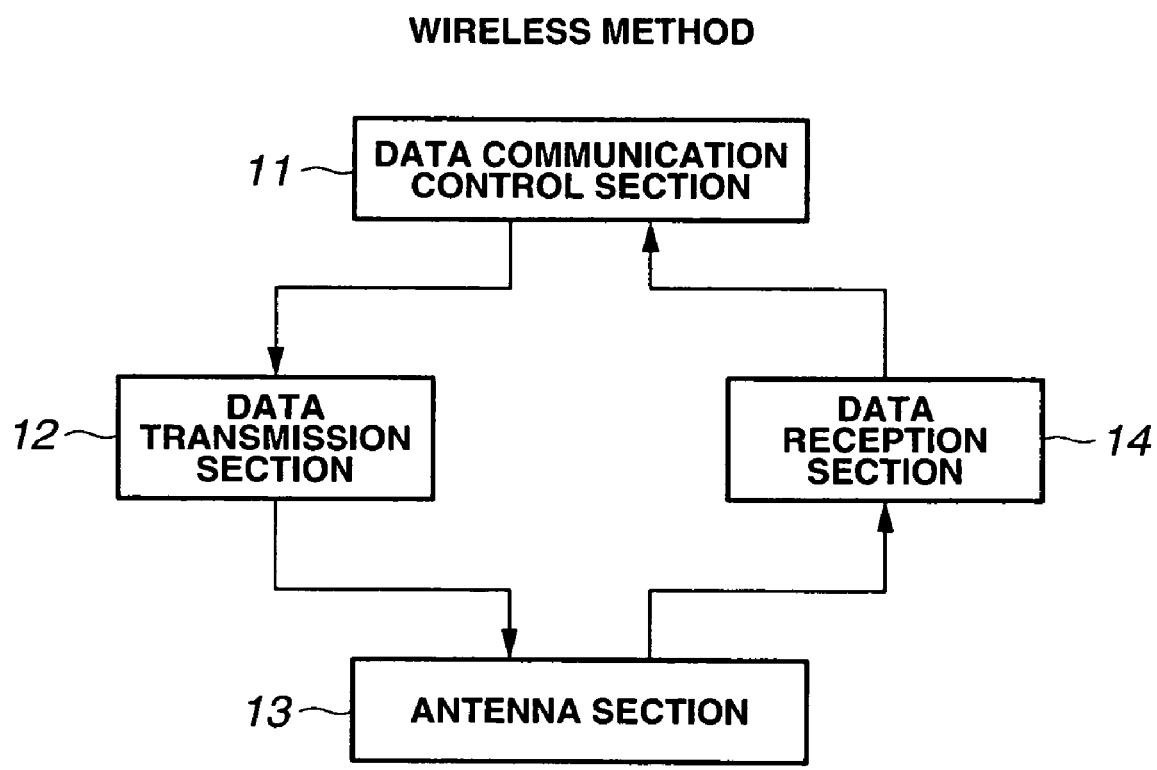
FIG. 2A shows a wireless data transmission mode used in the present invention.
Figure 2B:
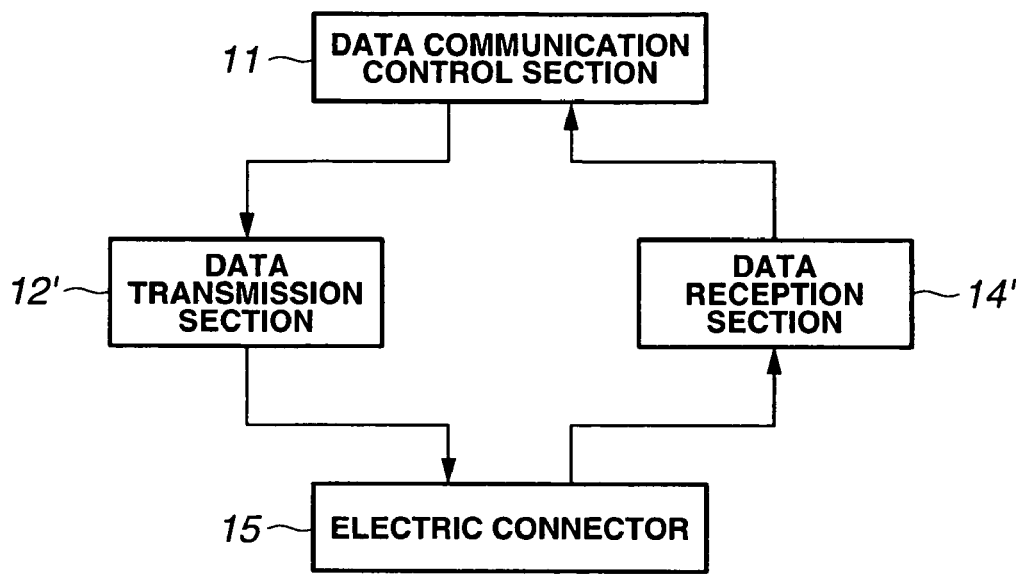
FIG. 2B shows a wired data transmission mode used in the present invention.
Figure 2C:
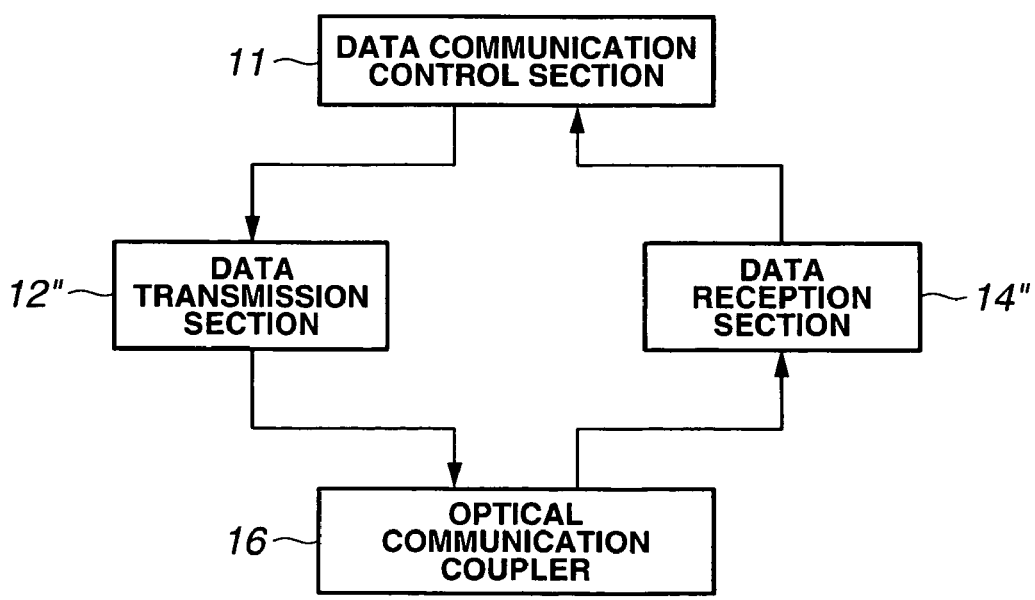
FIG. 2C shows an optical communication data transmission mode used in the present invention.

FIGS. 2A to 2C show data communication modes used in this embodiment and the like. The data communication modes are used as a data transmission and reception unit for data transmission and reception between the endoscope 3 and the operation remote controller 7, data transmission and reception between the endoscope 3 and the AWS unit 4, data transmission and reception between the AWS unit 4 and the endoscopic system control device 5, and the like.

FIG. 2A shows a wireless data transmission and reception unit. Herein, a description will be given of a case in which data transmission and reception are performed between the operation remote controller 7 and the endoscope 3. With a data communication control section 11 built in the operation remote controller 7, the operation remote controller 7 wirelessly transmits data, which is modulated by passing through a data transmission section 12, to the endoscope 3 from an antenna section 13.

Also, the operation remote controller 7 receives data, which is wirelessly transmitted from the endoscope 3 side, at the antenna section 13, and demodulates the data by a data reception section 14 to transmit the modulated data to the data communication control section 11. According to the present invention, when the data is transmitted in a wireless method, a wireless LAN is formed which has the maximum data communication speed of 54 Mbps on the basis of the IEEE802.11g standard, for example.

FIG. 2B shows a wired data transmission and reception unit. As a specific example, a description will be given of a case in which data transmission and reception are performed between the endoscope 3 and the AWS unit 4. With the data communication control section 11 built in the endoscope 3, the endoscope 3 transmits data via a data transmission section 12' to the AWS unit 4 from an electric connector 15 in a wired system. Then, the data transmitted from the AWS unit 4 passes through the electric connector 15 and a data reception section 14', and the data is transmitted to the data communication control section 11.

FIG. 2C shows an optical communication data transmission and reception unit. As a specific example, a description will be given of a case in which data transmission and reception are performed between the operation remote controller 7 and the endoscope 3. The data communication control section 11 built in the operation remote controller 7 is connected via a data transmission section 12" and a data reception section 14", which perform transmission and reception for optical communication, to an optical communication coupler 16 provided to the endoscope 3, and performs the data transmission and reception via the optical communication coupler on the endoscope 3 side.

Figure 3A:
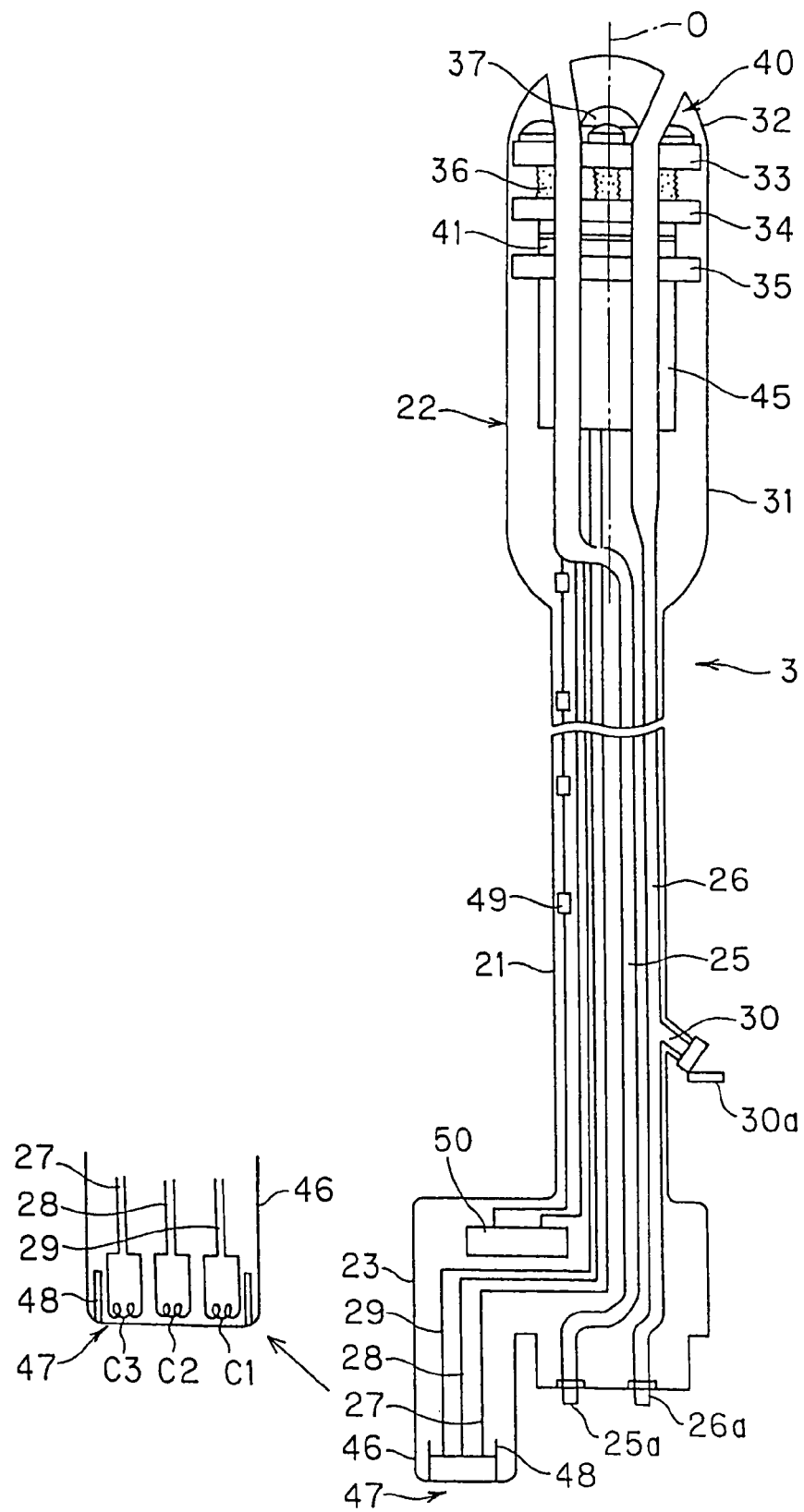
FIG. 3A shows an entire structure of an endoscope according to the first embodiment of the present invention.
Figure 3B:
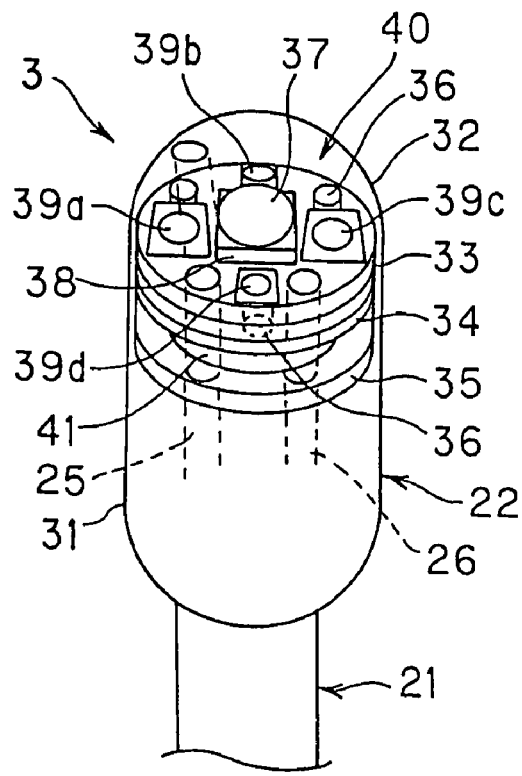
FIG. 3B shows a part of the endoscope at a distal end side according to the first embodiment of the present invention.

FIGS. 3A and 3B show a specific structure of the endoscope 3 according to this embodiment. It should be noted that FIG. 3A is a schematic cross sectional view, and FIG. 3B is a schematic perspective view with a transparent distal end cover seen through, showing an internal structure on the distal end side.

As shown in FIGS. 3A and 3B, the endoscope 3 includes an elongated insertion tube made of a flexible material (also referred to as tube body) 21 and a capsule section 22 having a capsule shape, which is integrally provided to a distal end of the insertion tube 21. A connector 23 is provided at a rear end of the insertion tube 21, and the connector 23 is detachably connected to the AWS unit 4.

In the insertion tube 21, an air water duct line 25 for performing airing and watering, a suction duct line 26 for performing suction, a power line 27, a (AWS unit) signal line 28, and a (remote control) signal line 29 are inserted. It should be noted that the power line 27 is connected to the AWS unit 4, whereby the power is supplied from the AWS unit 4 side. The (AWS unit) signal line 28 transmits a signal including image data between the AWS unit 4. The (remote control) signal lines 29 is a transmission line between the operation remote controller 7 for signal transmission mainly used for an operation section provided in the operation remote controller 7.

Rear ends of the air water duct line 25 and the suction duct line 26 are an air water connector 25a and a suction connector 26a in the connector 23, respectively. Then, the suction duct line 26 has an opening divaricated in an oblique direction on the rear end side in the vicinity of the connector 23, which functions as an endo-therapy product insert port through which an endo-therapy product such as forceps can be inserted (abbreviated as biopsy port) 30. The biopsy port 30 is occluded by a valve 30a when the endo-therapy product is not inserted. Distal end sides of the air water duct line 25 and the suction duct line 26 are respectively opened to the outside while penetrating through the inside of a capsule section 22.

In the capsule section 22, a capsule shaped exterior body (container body) 31 is integrally connected at a distal end of the thin insertion tube 21, whereby the inside of the exterior body 31 has a water tight structure. In this case, the exterior body 31 is connected to a hemi-spherical transparent distal end cover 32 on the distal end side of a substantially cylindrical trunk section with a structure in which light is transmitted in all the directions in the hemispherical form.

Then, as will be described later, via the operation remote controller 7, an inclination of a board of a first base member 33 on which an illumination and image pickup unit 40 in the capsule section 22 is provided is changed in an arbitrary direction. Thus, such a structure is achieved that illumination light is transmitted in arbitrary direction via the hemi-spherical transparent distal end cover 32, and at the same time reflection light on an external subject illuminated by the illumination light is transmitted, thereby forming the illumination section and the observation section (image pickup section) with which the observation in any direction can be performed.

In the exterior body 31, three disc shaped base members 33, 34, and 35 to be fitted to an inner circumference surface of the exterior body 31 are sequentially arranged in the longitudinal direction of the exterior body 31. The first base member 33 arranged at the most distal end is arranged in the vicinity of a base end of the hemispherical form in the distal end cover 32, and freely turnably arranged about a center axis O of the capsule section 22. Also, the first base member 33 is arranged in the vicinity of the base end of the hemispherical form in the distal end cover 32 so as to freely tilt in the following manner.

In addition, the first base member 33 is made an electroconductive polymer artificial muscle (abbreviated as EPAM), for example. The first base member 33 is connected to the second base member 34 via a view field varying articulation actuator 36 functioning as a view field varying section for varying the direction of view through expansion and contraction in response to voltage application. It should be noted that the view field varying articulation actuators 36 are respectively attached, as shown in FIG. 3B, for example, to three areas in the circumferential direction about the center axis O in a rod shape.

The second base member 34 is also freely turnable about the center axis O, and is arranged, for example, so as to be fitted to the inner circumference surface of the exterior body 31 while being prevented from tilting from the center axis O direction.

For this reason, as described above, the first base member 33 held to be freely tilting with the view field varying articulation actuators 36 provided at the three areas of the circumferential direction is expanded by applying the view field varying articulation actuator 36 with a voltage, whereby the first base member 33 is tilted in the view field varying articulation actuator 36 held in the least expanded state (tilted from the direction of a surface orthogonal to the center axis O).

As shown in FIG. 3B too, an objective lens 37 is arranged in the center of the disc of the first base member 33, and a charged coupled device (abbreviated as CCD) 38 having a gain varying function as an image pickup element is arranged at the image forming location, thereby forming an image pickup section. An R-LED 39a, a G-LED 39b, a B-LED 39c, and an IR-LED 39d for emitting lights in red, green, blue, and infrared wavelengths, respectively, are arranged as illumination sections at four areas around the CCD 38, for example, thereby forming the illumination and image pickup unit 40.

In the case of a normal observation mode in a visible area, for example, the R-LED 39a, the G-LED 39b, and the B-LED 39c are simultaneously caused to emit the lights to output the R, G, and B illumination lights to the front side of the distal end cover 32, and in the illumination state, the image pickup is performed by the CCD 38. Meanwhile, in the case of a special light observation mode by using a special light other than visible area lights, that is, in the case of an infrared observation mode for performing an infrared observation in this specific example, the IR-LED 39d is emitted and the infrared illumination light is output to the front side of the distal end cover 32, and in the illumination state, the image pickup is performed by the CCD 38. For example, when a deep area side is desired to be observed instead of a surface, this infrared observation mode is set and the observation is performed. As a result, optical information on the deeper area side is obtained as compared with the case of the visible area illumination light.

In this way, according to this embodiment, the normal observation mode and the infrared observation mode can be switched and performed. For this reason, for example, as shown in 11B described below, the normal observation mode or the infrared observation mode is selected from a main menu, and it is possible to set a state of the illumination light quantity corresponding to each of the modes, or the like. In addition, a function of switching the normal observation mode and the infrared observation mode by using a function switch can be allocated.

As described above, when the first base member 33 is tilted via the view field varying articulation actuator 36, the illumination and image pickup direction (observation view field direction) by the illumination and image pickup unit 40 can be changed. That is, by tilting the first base member 33, a view field direction varying section is formed.

As will be described later, the user operates to rotate a track ball 19 of the operation remote controller 7, thereby making it possible to tilt (bend) the board of the first base member 33 on which the illumination and image pickup unit 40 is formed, in an arbitrary direction. In this case, regarding the tilting angle, as shown in FIG. 3A, when a position in a state orthogonal to the center axis O corresponds to a reference view field direction, the board can be freely tilted by approximately 90° in an arbitrary direction from the reference observation view field direction (in this specification, the operating of changing the view field direction is also referred to as articulation operation in an analogous fashion to a bending operating).

As will be described later with FIG. 11A, the observation view field direction of the illumination and image pickup unit 40 is displayed on the observation monitor 6 together with an endoscope image, and thus satisfactory operability can be ensured.

In addition, a distal end turning actuator 41 functioning as a distal end turning member such as a motor is arranged between the second base member 34 and a third base member 35, so that the second base member 34 side is turnable by approximately 90° in the clockwise and anticlockwise directions with respect to the third base member 35 fixed to the inner circumference surface of the exterior body 31.

In this case, for example, when the observation view field direction of the illumination and image pickup unit 40 is along the center axis of FIG. 3A, the observation (more specifically, captured by the CCD 38) image plane is merely rotated. When the observation view field direction of the illumination and image pickup unit 40 is set in a different direction from the center axis O (by the view field direction varying section through the above-mentioned tilting), the view field direction can be changed through this rotating operation.

Therefore, by using the both in combination, the view field direction can be set to be widely changed.

The base members 33 to 35 have holes for letting the air water duct line 25 and the suction duct line 26 through. The air water duct line 25 and the suction duct line 26 inserted through the insertion tube 21 are opened on an outer peripheral surface of the distal end cover 32.

Then, the user performs an instruction operation to rotate the distal end turning actuator 41 by operating operation remote controller 7, whereby the distal end turning actuator 41 turns (with respect to the fixed third base member 35) the second base member 34 that is freely turnably arranged at the distal end thereof. In particular, the direction of the distal end side of the suction duct line 26 can be changed.

That is, when the endo-therapy product is inserted from the biopsy port 30 and a distal end side of the endo-therapy product protrudes from a distal end opening of the suction duct line 26, by turning the distal end turning actuator 41, the direction of the distal end side of the endo-therapy product can be controlled to be varied. In other words, the endoscope 3 according to this embodiment has a function like a hebel for varying and adjusting a protruding direction of the endo-therapy product.

Then, a video processing circuit 42 (not shown in the drawing) for performing a video processing on the CCD 38, a control circuit 43 (not shown in the drawing) for performing a control process for the respective sections in the endoscope 3, and a power supply circuit 44 for generating power (refer to FIG. 6) are arranged on a back side of the third base member 35, for example. It should be noted that the video processing circuit 42, the control circuit 43, and the power supply circuit 44 are abbreviated as control unit 45.

The power supply circuit 44 is connected to the power line 27, and the control circuit 43 and the video processing circuit 42 are connected to both the signal lines 28 and 29. Rear ends (base ends) of the power line 27 and both the signal lines 28 and 29 inserted through the insertion tube 21 are connected to a contactless transmission section 47 of an electric connector 46 in the connector 23. It should be noted that the contactless transmission section 47 is formed by coils C1, C2, and C3 as shown in the enlarged view of FIG. 3A. Then, circumferences of the respective coils of the contactless transmission section 47 and the entire circumference of these coils are coated with a shield member 48, thereby forming an electromagnetic shielding section for preventing noise radiation and contamination.

Also, according to this embodiment, in the insertion tube 21, insertion shape detecting coils (abbreviated as UPD coils) 49 for detecting the shape of the insertion tube 21 are further arranged at an appropriate interval. For example, in response to drive signals from UPD coil driver sections 50 arranged in the connector 23, the UPD coils 49 are sequentially driven.

The UPD coil driver section 50 is connected via a signal line to the control circuit 43 of the control unit 45.

Figure 4A:
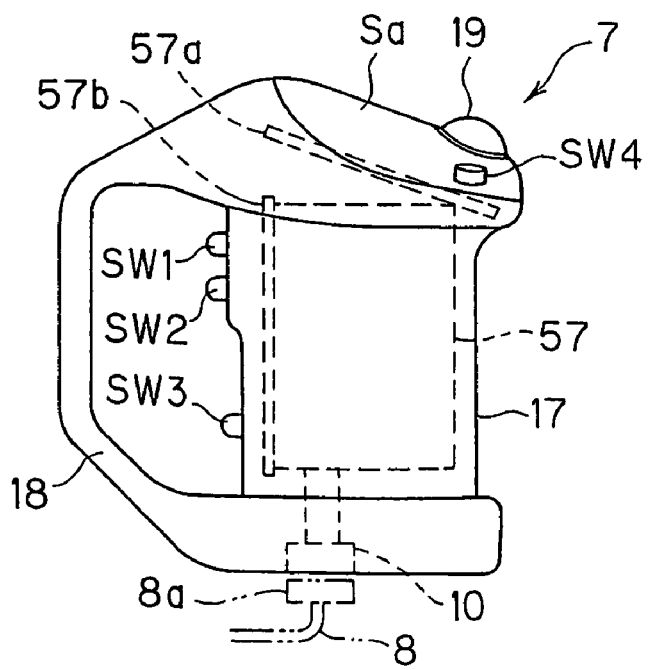
FIG. 4A is a side view showing an operation remote controller.
Figure 4B:
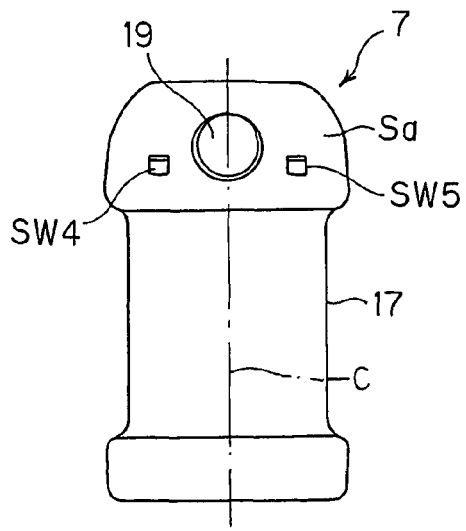
FIG. 4B is a front view showing the operation remote controller.
Figure 4C:
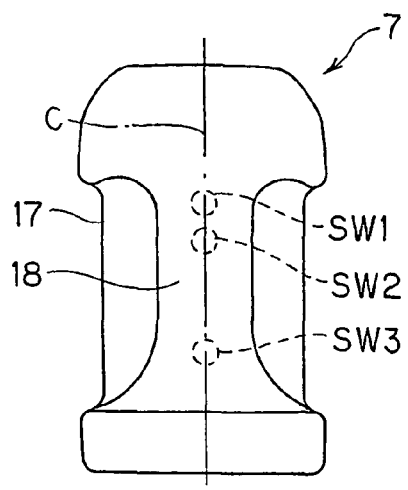
FIG. 4C is a back view showing the operation remote controller.
Figure 4D:
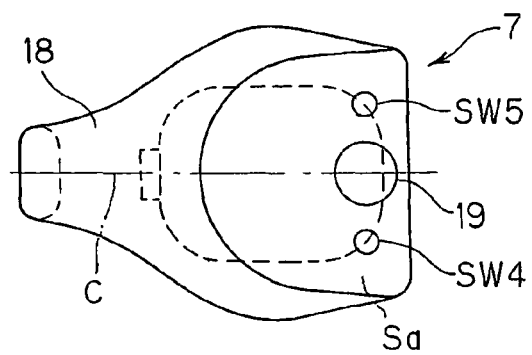
FIG. 4D is a plan view showing the operation remote controller.

On the other hand, the operation remote controller 7 detachably connected to the AWS unit 4 has, specifically, a structure shown in FIGS. 4A to 4D. It should be noted that FIG. 4A is a side view as seen from the side of the operation remote controller 7, FIG. 4B is a front view as seen from the right hand side of FIG. 4A, FIG. 4C is a back view as seen from the left hand side of FIG. 4A, and FIG. 4D is a plan view as seen from the top of FIG. 4A.

As shown in FIG. 4A or the like, the operation remote controller 7 includes a substantially cylindrical grasping section 17 which the user like a surgeon grasps, and also a substantially U-shaped hook (or, a handle) 18 for linking upper and lower sides of the grasping section 17. The hook 18 is thus provided, so even when the surgeon does not grasp the grasping section 17 hard, the operation remote controller 7 can be prevented from dropping.

The operation remote controller 7 according to this embodiment has an inclined surface Sa inclined to the upper end side and the track ball 19 for the articulation operation arranged on the inclined surface Sa.

The track ball 19 is located on a center line C extending in the longitudinal direction of the bilaterally symmetric operation remote controller 7 as shown in the front view of FIG. 4B. In addition, an air water switch SW4 and a suction switch SW5 are arranged at locations on both sides bilaterally symmetric to the track ball 19.

Moreover, function switches SW1 to SW3 are sequentially arranged from the upper side to the lower side on the end side opposite to the side where the track ball 19 is provided along the center line C of the back view of FIG. 4C. In this way, in the operation remote controller 7 according to this embodiment, the bilaterally symmetric shape is formed as is understood from FIGS. 4B and 4C, and at the same time the track ball 19, the function switches SW1 to SW3, the air water switch SW4, the suction switch SW5, which function as the operation section, are bilaterally symmetrically provided. In either of cases where the right-handed surgeon grasps the operation remote controller 7 and the left-handed surgeon grasps the operation remote controller 7, equally satisfactory operability can be ensured.

Figure 5B:
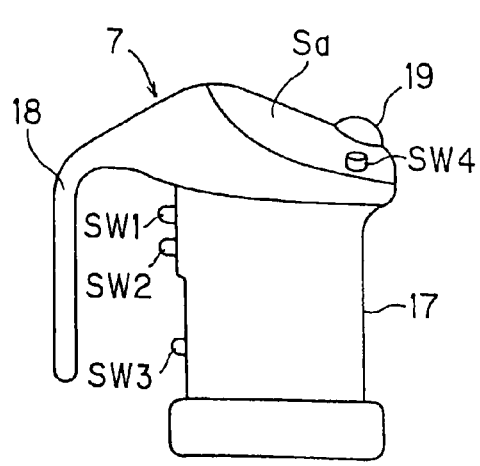
FIG. 5B shows a modification example of the operation remote controller.
Figure 5A:
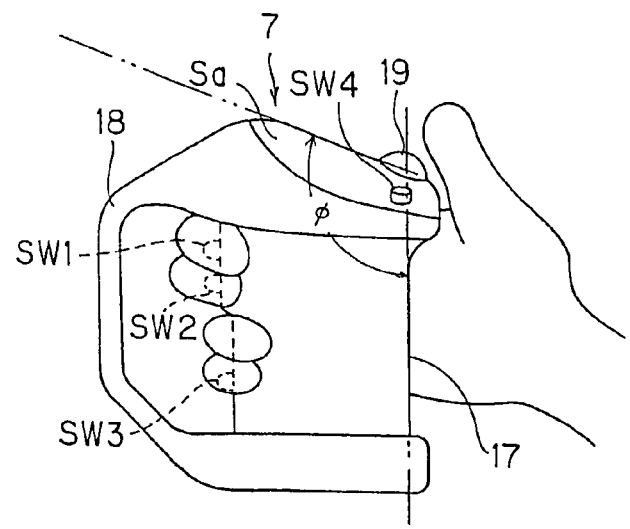
FIG. 5A shows a use example of the operation remote controller operated by being grasped.

To be specific, as shown in FIG. 5A, for example, the surgeon can easily operate by grasping the grasping section 17 with the right hand. In this case, for the surgeon who grasps the grasping section 17 with the left hand, the satisfactory operability can be ensured similarly.

It should be noted that, as shown in FIG. 5A, while an angle of the inclined surface Sa with respect to an axis of the longitudinal direction of the operation remote controller 7 (this axis is parallel to the center line C shown in FIG. 4B) is set as $\phi$, if $\phi$ is in the range from 90° to 180°, in the case where the grasping section 17 is operated with a thumb, the satisfactory operability can be ensured. An angle for more ease of use is desirably set in the range from 120° to 150°.

It should be noted that FIG. 5B shows a modification example of the operation remote controller 7. In this case, the lower end side of the hook 18 is not linked to the lower end side of the grasping section 17, and the lower end side of the hook 18 is opened.

Figure 7:
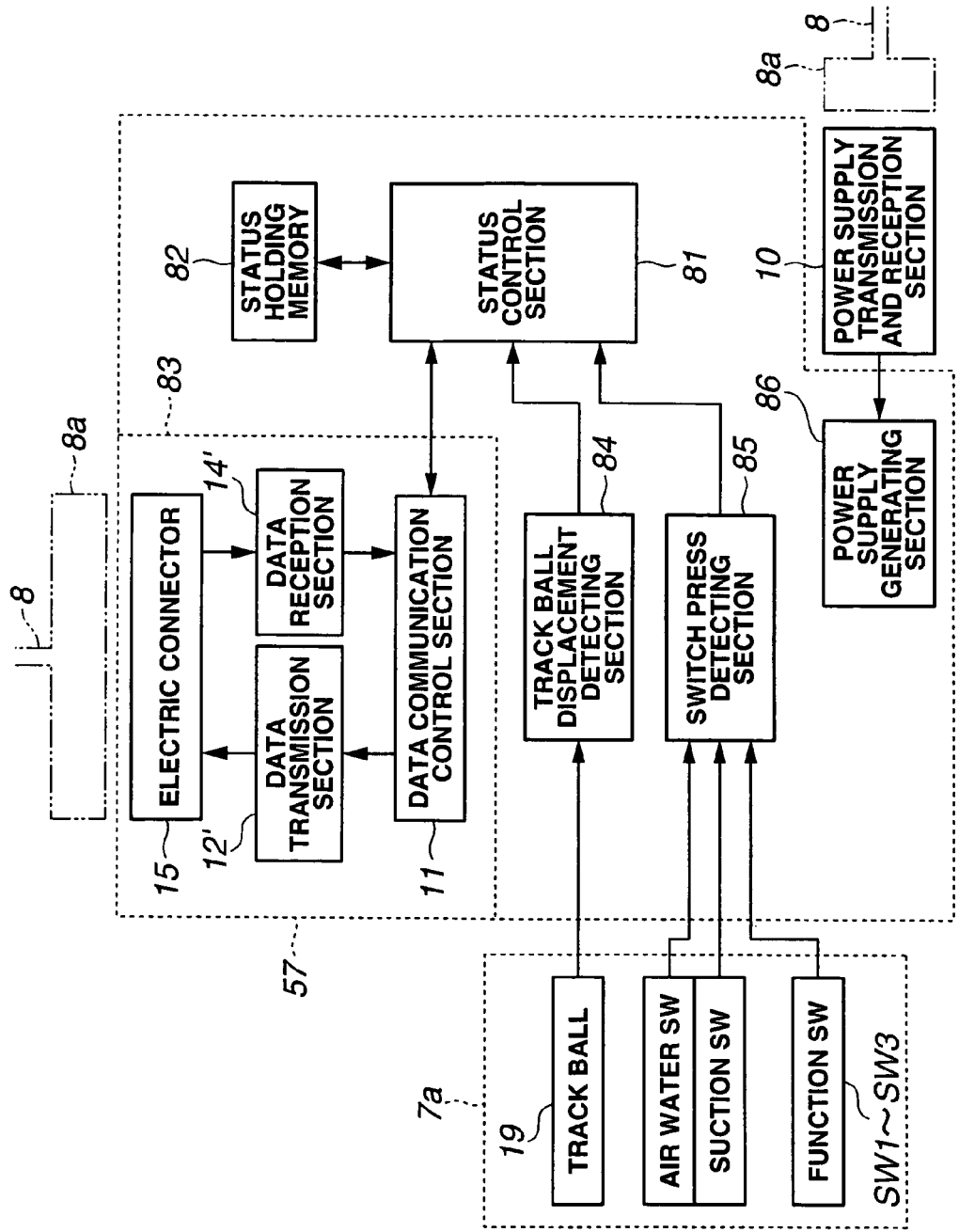
FIG. 7 is a block diagram showing an electrical system configuration of the operation remote controller.

The operation remote controller 7 has a control circuit 57 shown in FIG. 7 built in the exterior body having a water tight structure and a tolerance for a disinfection or sterilization process.

Also, as shown in FIG. 4A, for example, the contactless electric connector (a power supply transmission and reception section of FIG. 7) 10 is provided on the inner side of the lower side in the operation remote controller 7, and supplied with an alternating current power from the AWS unit 4 which is connected to a contactless electrical connector 8a arranged at one end of the connection cable 8 and also connected to an electrical connector 8b arranged at the other end of the connection cable 8. Then, the power supply generating section in the control circuit 57 accommodated inside the grasping section 17 generates a direct current power supply from the supplied alternating current power.

It should be noted that the control circuit 57 shown in FIG. 4A is formed by mounting a track ball board 57a to which the track ball 19 is connected, a switch board 57b to which the function switches SW1 to SW3 are connected, and the like.

In this manner, with the structure where the operation remote controller 7 is connected to the connection cable 8 in a contactless fashion, when the operation remote controller 7 is repeatedly subjected to washing and sterilization for a long period of time before or after the surgeon uses for the endoscopy, corrosion or the like can be effectively prevented in the case of the contactless fashion unlike the case of the contact fashion.

Next, with reference to FIG. 6, a structure of an electrical system of the endoscope 3 will be described. In a distal end portion 22a in the capsule section 22, a view field varying articulation actuator (the actuator is abbreviated as ACT in the drawings) 36, the encoder 51 for detecting the amount of displacement, an the LED 39 (reference numerals 39a to 39D of FIG. 3A are represented by one reference numeral 39), and the CCD 38 are arranged. Furthermore, in a trunk section 22b in the vicinity of the center of the capsule section 22, the distal end turning actuator 41 and an encoder 52 for detecting the amount of displacement are arranged.

The insertion tube 21 includes the UPD coils 49. The connector 23 of the insertion tube 21 includes the UPD coil driver section 50 and a power supply transmission and reception section 53 (specifically, the coil C1 of the contactless transmission section).

On the other hand, the control unit 45 including the video processing circuit 42 and the power supply circuit 44 has a status control section 61 composed of a CPU for managing control status of the respective sections, and the like. The status control section 61 is connected to a status holding memory 62 for holding (storing) a status of the respective sections, and also to transmission and reception units 63A and 63B of a wired method (according to this embodiment) for performing wired communication with the AWS unit 4 and the operation remote controller 7.

It should be noted that the transmission and reception units 63A and 63B are equivalent to the transmission and reception units of the wired method shown in FIG. 2B. In this case, the electric connector 15 is equivalent to the coil C2 of the contactless transmission section 47 connected to the AWS unit 4. The transmission and reception unit 63B has the same structure as that of the transmission and reception unit 63A. Then, the transmission and reception unit 63B functions as an electric connector connected to the electric connector 8b at the base end of the connection cable 8 that is connected to the operation remote controller 7.

The status control section 61 controls, via an illumination control section 64 for controlling the illumination, the LED driver section 65 to be controlled by the illumination control section 64. The LED driver section 65 applies an LED 39 functioning as an illumination section, with an LED driver signal for causing the LED 39 to emit the light.

With the light emission from the LED 39, a subject such as an illuminated affected area is image-formed on an image pickup surface of the CCD 38 arranged at the image forming location by the objective lens 37 attached to an observation window, and photoelectrically converted by the CCD 38.

The CCD 38 outputs a signal charge accumulated through the photoelectrical conversion as an image pickup signal in response to application of a CCD driver signal from a CCD driver section 66 controlled by the status control section 61. After converted into a digital signal from an analog signal by an A/D converter (abbreviated as ADC) 67, this image pickup signal is input to the status control section 61 and at the same time the digital signal (image data) is stored in an image memory 68. The image data of the image memory 68 is sent to the data transmission section 12' of the transmission and reception unit 63A.

Then, the image data is sent from the electric connector 15 through the AWS unit 4, and wirelessly transmitted from the AWS unit 4 to the endoscopic system control device 5 side.

An output signal of the ADC 67 is sent to a brightness detecting section 69. Information on the image brightness detected by the brightness detecting section 69 is sent to the status control section 61. The status control section 61 performs light intensity adjustment on the basis of this information, so that the illumination quantity by the LED 39 is set to an appropriate brightness via the illumination control section 64.

In addition, the status control section 61 controls an actuator driver section 72 via an articulation control section 71, and the actuator driver section 72 drives the view field varying articulation actuator (EPAM) 36. It should be noted that the drive amount of the view field varying articulation actuator 36 is detected by the encoder 51, and on the basis of the detection by the encoder 51, the drive amount of the view field varying articulation actuator 36 is controlled to be a value corresponding to the instructed amount.

Also, the status control section 61 controls a distal end turning control section 73, and the distal end turning control section 73 drives the distal end turning actuator 41 via the control of the actuator driver section 74 under the control of the status control section 61. The drive amount of the distal end turning actuator 41 is detected by the encoder 52.

In addition, the status control section 61 performs timing management or the like via the UPD coil driver sections 50 in the case in which the UPD coils 49 are driven.

Furthermore, the alternating current power transmitted from the power supply transmission and reception section 53 is supplied to the power supply circuit 44, and the power supply circuit 44 converts into direct current power supply for supplying the respective sections of the control unit 45 with the operation power.

It should be noted that device model information or use status unique to the respective endoscopes 3 may be written and held in the status holding memory 62 in the following manner, and the information may be effectively used.

To be specific, the status holding memory 62 holds, for example, device model information on the endoscope 3 (for example, information on a type of the CCD 38, the length of the insert section of the insertion tube 21, or the like), and individual information different in each of the endoscopes 3 due to the use status for the endoscopy or the like (for example, information on use time (summed up use time or accumulated use time for the endoscopy), the number of times for performing washing, an adjusted value, a maintenance history, or the like). These pieces of information are used for the system operation decision, information provision to the user, etc.

These pieces of information can be edited from the outside, such as the endoscopic system control device 5, a washing device not shown, or the like.

As a result, it is possible to effectively use the information (data) which the endoscope ID has, while the status holding memory 62 doubles as the function of the existing endoscope ID to be commonly used. It should be noted that the same applies to a status holding memory 82 which will be described later.

Moreover, with the provision of the status holding memory 62, it is unnecessary to additionally provide a separate endoscope ID, so more advanced function than the existing endoscope ID can be achieved, thereby making it possible to perform appropriate setting, adjustment, management, processing, and the like in more detail.

On the other hand, the internal structure of the operation remote controller 7 has such a structure shown in FIG. 7. The control circuit 57 inside the operation remote controller 7 has a status control section 81 composed of a CPU for managing control status of the respective sections, and the like. The status control section 81 is connected to a status holding memory 82 for holding (storing) a status of the respective sections, and also connected to a transmission and reception unit 83 of wired communication mode. The transmission and reception unit 83 is directly connected to the electric connector of the AWS unit 4, and is also connected via the electric connector to the electric connector of the endoscope 3, thereby mutually performing wired communication with the endoscope 3. The structure will be described later with respect to FIG. 8.

In addition, the status control section 81 is connected to a track ball displacement detecting section 84 for detecting the amount of displacement of the track ball 19 arranged at a location where the operation can be performed by a hand grasping on an outer surface 7a of the operation remote controller 7 (including the inclined surface or the like). The status control section 81 holds the detected amount of displacement in the status holding memory 82, and at the same time sends the data to the data communication control section 11 of the transmission and reception unit 83 to be transmitted to the endoscope 3.

Then, the air water switch SW4, the suction switch SW5, and the function switches SW1 to SW3 arranged at locations where the operation can be performed by the hand grasping on the outer surface 7a of the operation remote controller 7 are connected to a switch press detecting section 85. The switch press detecting section 85 detects when the respective switches are pressed, and outputs the detection signal to the status control section 81. The status control section 81 holds the detected respective switch statuses in the status holding memory 82, and at the same time sends the data to the data communication control section 11 of the transmission and reception unit 83 to be transmitted to the endoscope 3.

A power supply generating section 86 provided in the control circuit 57 is connected to the power supply transmission and reception section shown in FIG. 4A. The alternating current power transmitted from the power supply transmission and reception section is converted to the direct current power source, and the respective sections in the control circuit 57 are supplied with the operation power.

Figure 8:
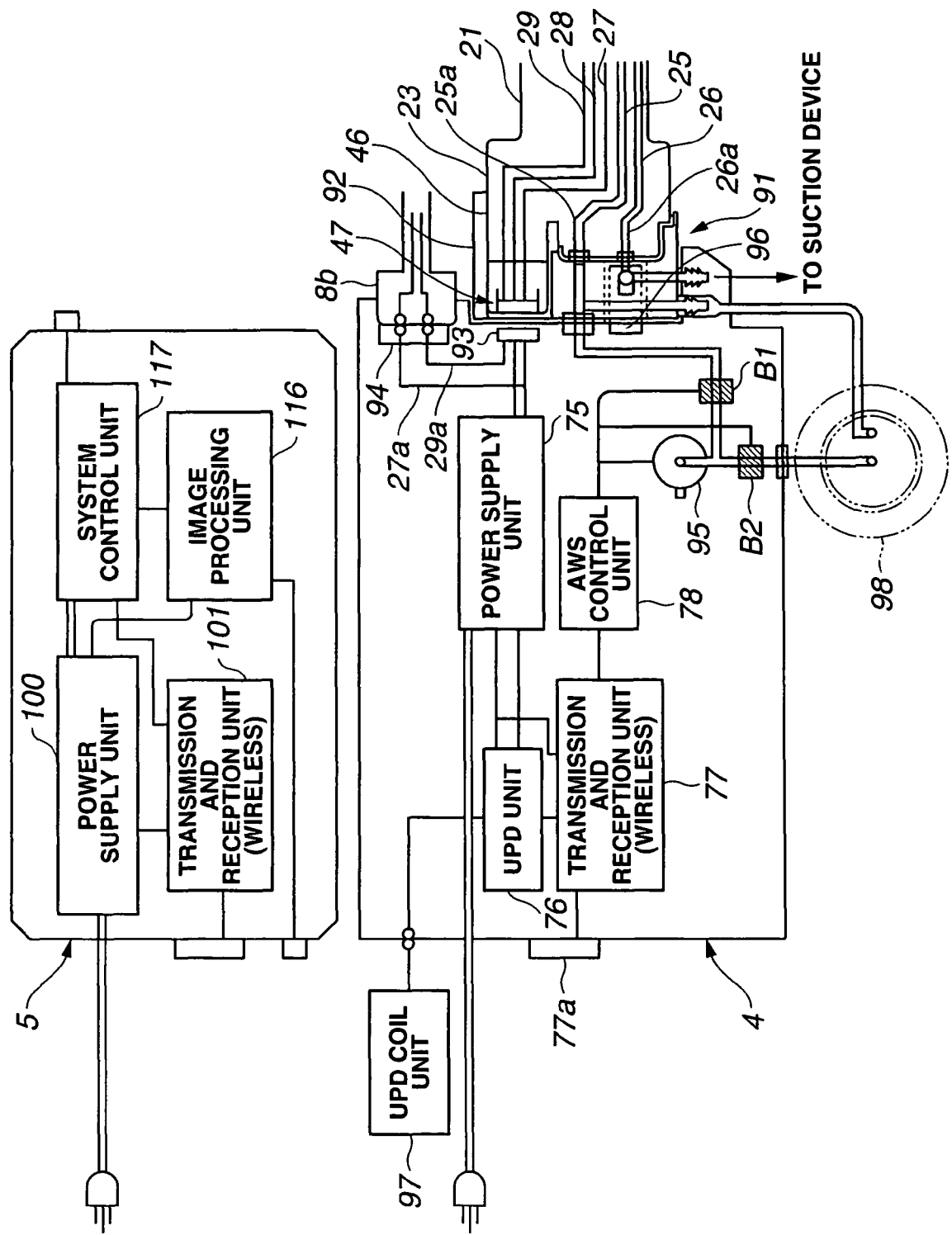
FIG. 8 shows a structure in the vicinity of a connector of an AWS unit.
Figure 9:
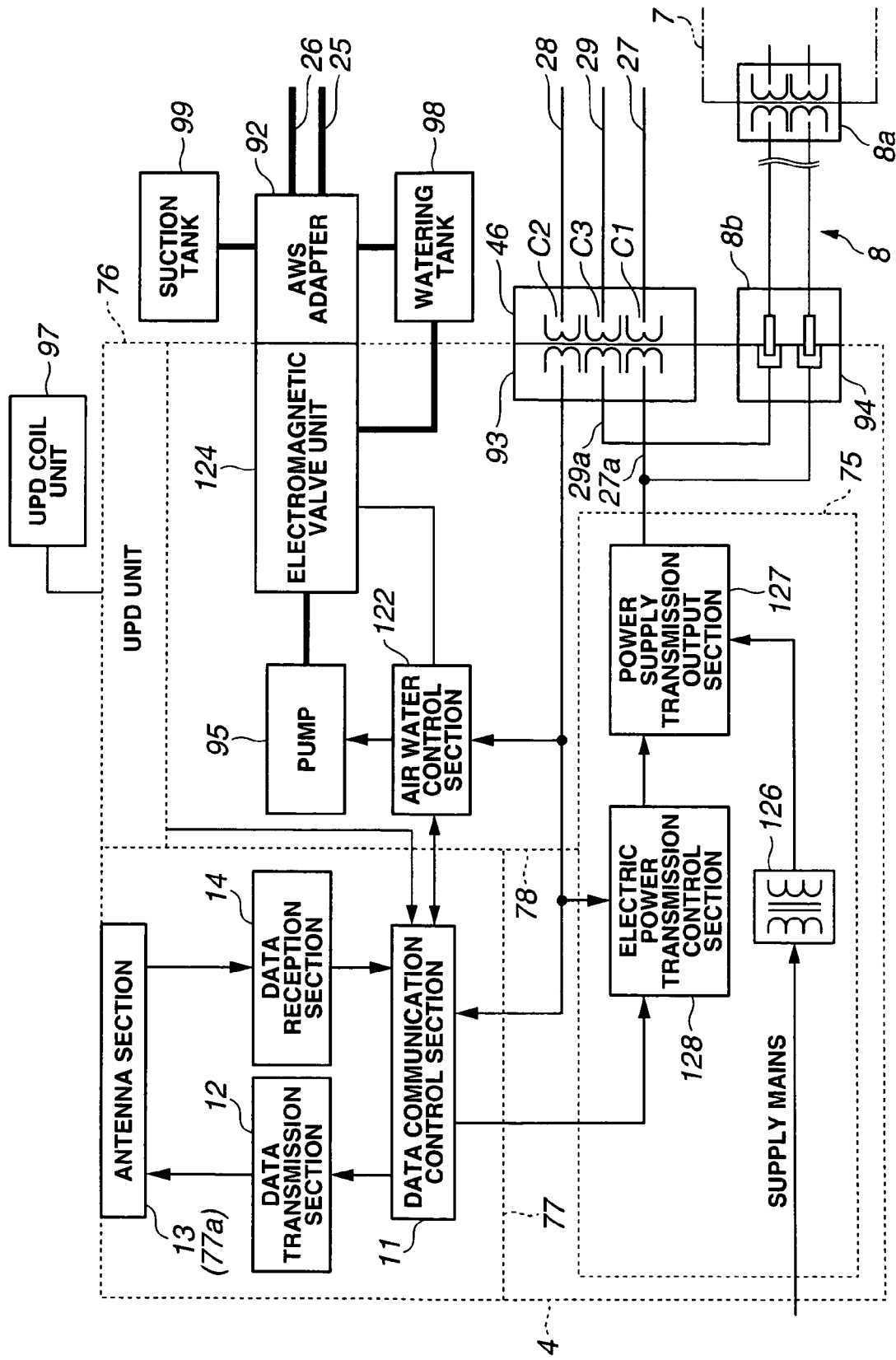
FIG. 9 is a block diagram showing an electrical system configuration of the AWS unit.

FIGS. 8 and 9 show the internal structure of the AWS unit 4.

The connector 23 of the endoscope 3 is connected to a scope connector 91 of the AWS unit 4 while an AWS adapter 92 is inserted.

A convex portion is formed on a front surface of the AWS unit 4. The AWS adapter 92 is detachably connected to the convex portion which is provided with the duct line connector. Also, the AWS adapter 92 includes a through hole. Via this through hole, the (contactless) electric connector 46 in the connector 23 is inserted, and an (contactless) electric connector 93 of the AWS unit 4 is detachably connected.

In addition, the connector 8b (for example, of an electrical contact method) provided to the connection cable 8 that is connected to the operation remote controller 7 is also detachably connected to an electric connector 94 of the AWS unit 4 (for example, of an electrical contact method).

Then, a signal line 29a connected to the signal line 29 of the electric connector 93 in the AWS unit 4 is connected to a contact of an electrical connector 94. That is, the signal line 29 of the endoscope 3 is connected to the operation remote controller 7 via the signal line 29a in the AWS unit 4 to transmit the operation information by the operation remote controller 7 to the endoscope 3, and is also capable of sending reply information from the endoscope 3 or the like to the operation remote controller 7.

Also, the power line 27 is connected to a power supply unit 75 via the electric connector 93, and the endoscope 3 is supplied with the alternating current power from the power supply unit 75 via the power line 27. Furthermore, the power line 27 is connected to a power line 27a for supplying the operation remote controller 7 in the AWS unit 4 with the power, and accordingly the operation remote controller 7 is also supplied with the alternating current power.

The AWS unit 4 has, in addition to the power supply unit 75 including a power supply control unit, an AWS control unit 78, a UPD unit 76, and a wireless transmission and reception unit 77 build therein.

The AWS control unit 78 performs operation control for an air water pump, and at the same time controls opening and closing of an electromagnetic valve B2 installed in the midway of a water duct between a watering tank 98 connected to a pump 95 and an electromagnetic valve B1 installed in the midway of an air duct.

The air water connector 25a of the endoscope 3 is branched inside the AWS adapter 92, one of which is connected to the air duct inside the AWS unit 4, and the other side of which branched to the side protrudes as a watering connector and is connected to the watering tank 98 via a tube connected to this watering connector. The suction connector 26a is branched inside the AWS adapter 92, one of which branched to the side protrudes as a suction connector and is connected to a suction device not shown, and the other of which, a relief duct, passes inside a pinch valve 96 protruding to the front side of the AWS unit 4.

The UPD unit 76 is connected to a UPD coil unit 97 located around the inspection bed 2. With the UPD coil unit 97, the locations of the UPD coils 49 are detected, and the shape of the insertion tube 21 is calculated, thereby performing a process of generating an image of an insertion shape (abbreviated as UPD image).

The transmission and reception unit 77 is connected to an antenna section 77a. Via the antenna section 77a, transmission and reception of information including the image data is wirelessly performed with the endoscopic system control device 5.

A further description will be given here. The information including the image data input (by the CCD 38) from the control circuit 43 of the endoscope 3 via the electric connector 93 is output to a data communication control section of the transmission and reception unit 77 shown in FIG. 9. Together with the UPD image data of the UPD unit 76, the information is transmitted from the antenna section 13 (77a) to the endoscopic system control device 5.

AWS related information on the operations for the air water switch SW4, the suction switch SW5, and the like, which are provided to the operation remote controller 7 is sent to an air water control section 122. The air water control section 122 controls the operations of the pump 95 and an electromagnetic valve unit 124 in accordance with the information on operation.

The air water duct line 25 is connected to the electromagnetic valve unit 124 via the AWS adapter 92. The watering tank 98 is connected to the electromagnetic valve unit 124 and the AWS adapter 92, and a suction tank 99 is connected to the AWS adapter 92.

The AWS unit 4 is supplied with supply mains (alternating current power), and this alternating current power is sent to a power supply transmission output section 127 via an insulation transformer 126. The power supply transmission output section 127 supplies the alternating current power insulating from the supply mains from the electric connector 93 to the power line 27 of the endoscope 3 connected to the electric connector 93.

Output control for electric power transmission of the power supply transmission output section 127 (corresponding to the contactless electric power transmission mode) is controlled by an electric power transmission control section 128 connected to the data communication control section 11 (as will be described later with reference to FIGS. 12 and 13).

Figure 10:
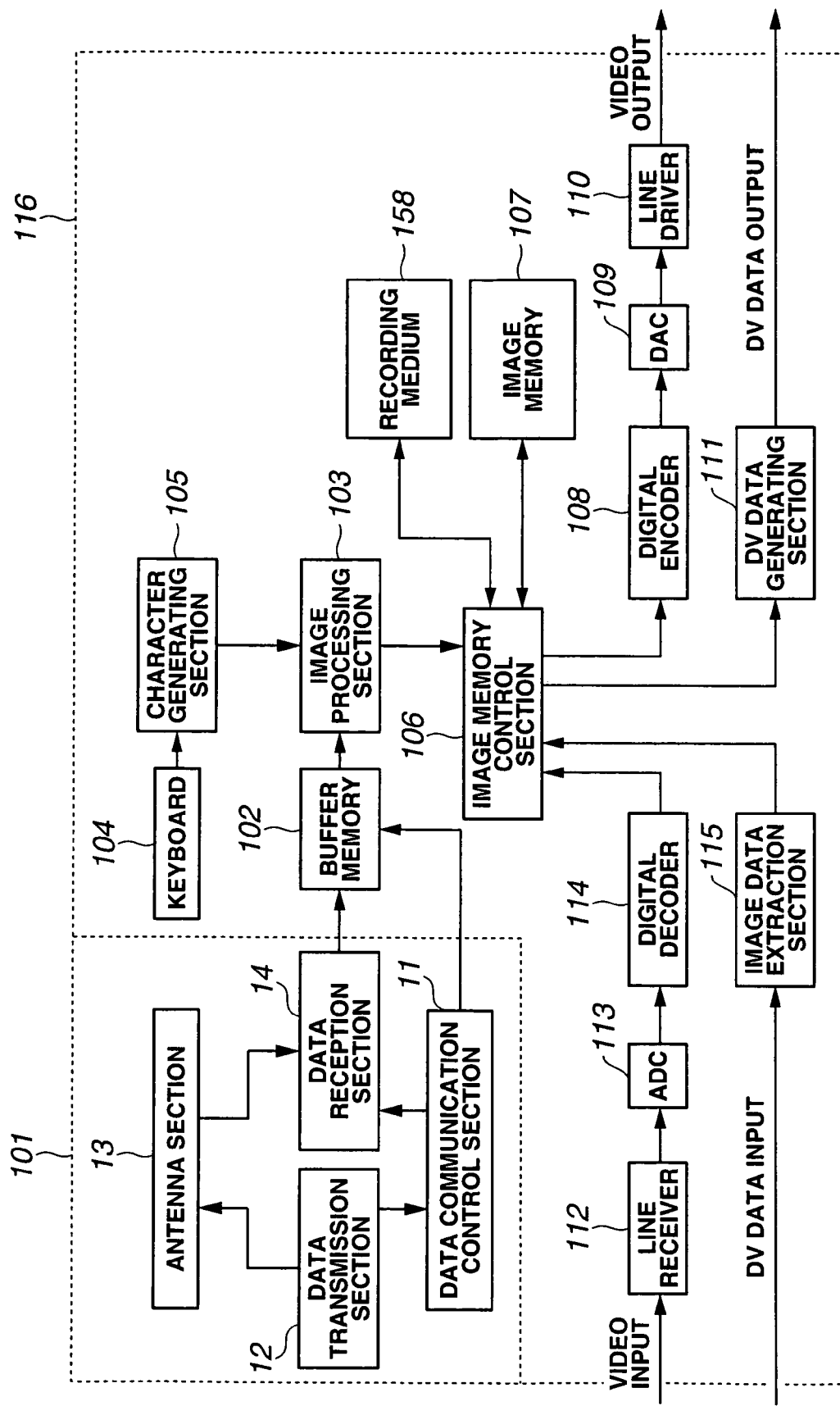
FIG. 10 shows structures of an image processing unit and a transmission and reception unit in an endoscopic system control device.

FIG. 10 shows internal structures of a transmission and reception unit 101 and an image processing unit 116 of FIG. 8 in the endoscopic system control device 5.

The endoscopic system control device 5 includes, for example, the wireless transmission and reception unit 101. Data such as an image signal wirelessly transmitted from the AWS unit 4 is taken in by the antenna section 13 to be sent to the data reception section 14. After being amplified, the data is subjected to a demodulation process. The operation of the data reception section 14 is controlled by the data communication control section 11, and the received data is sequentially accumulated in a buffer memory 102.

The image data in the buffer memory 102 is transmitted to an image processing section 103 for processing the image data. Character information from a character generating section 105 for generating character information in response to key input of a keyboard 104 is also input into the image processing section 103 other than the image data from the buffer memory 102, whereby it is possible to superimpose the character information or the like on the image data.

The image processing section 103 sends the input image data or the like to an image memory control section 106. Via the image memory control section 106, the image data or the like is temporarily stored in an image memory 107, and at the same time recorded in a recording medium 158.

The image memory control section 106 reads out the image data temporarily stored in the image memory 107 to be sent to a digital encoder 108. The digital encoder 108 encodes the image data into a predetermined video format and outputs the data to a D/A converter (abbreviated as DAC) 109. The DAC 109 converts a digital video signal into an analog video signal. The analog video signal is further output from a video output terminal to the observation monitor 6 via a line driver 110, and the observation monitor 6 displays an image corresponding to the video signal.

Then, the image data temporarily stored in the image memory 107 is read out to be input to a DV data generating section 111 as well. By the DV data generating section 111, DV data is generated to be, output from a DV data output terminal.

The endoscopic system control device 5 includes a video input terminal and a DV data input terminal. A video signal input from the video input terminal passes through a line receiver 112 and an ADC 113. The video signal converted into the digital signal is demodulated by a digital decoder 114 to be input to the image memory control section 106.

From the DV data input to the DV data input terminal, image data is extracted (decoded) by an the image data extraction section 115 to be input to the image memory control section 106.

The image memory control section 106 temporarily stores the video signal (image data) input from the video input terminal or the DV data input terminal in the image memory 107, records in the recording medium 158, or outputs from the video output terminal to the observation monitor 6.

According to this embodiment, from the AWS unit 4 side, image data captured by a CCD 25 of the endoscope 3 and the UPD image data generated from the UPD unit 76 are wirelessly input to the endoscopic system control device 5. The endoscopic system control device 5 converts these pieces of the image data into predetermined video signals to be output to the observation monitor 6.

Figure 11A:
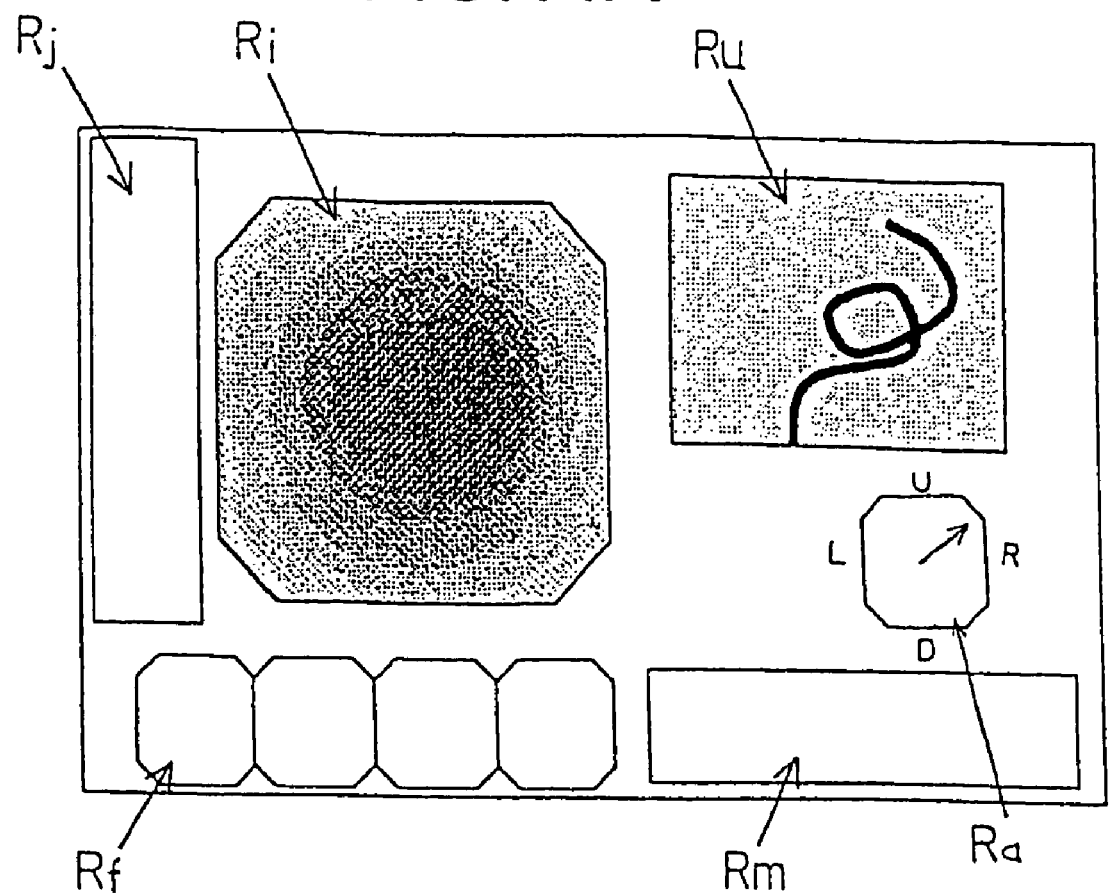
FIG. 11A shows a display example of an endoscopic image and the like on a monitor.

In the endoscopic system 1 according to this embodiment, when the power supply is activated, various images shown in, for example, FIG. 11A are displayed on the observation monitor 6. In this case, in addition to an information display area Rj for displaying patient information or the like, a display area Ri of the endoscope image, a display area Ru of the UPD image, a display area Rf of a freeze image, and a display area Ra of a view field varying articulation, a menu display Rm is provided. A menu is displayed on the menu display Rm.

Herein, a display area Ra of a view field varying articulation displays positioning dots U, D, L, and R indicating up, down, left, and right directions corresponding to directions of the operation of the track ball 19. Then, in accordance with the operation of the track ball 19, the view field direction in which the illumination and image pickup unit 40 is actually variably set, for example, is displayed with an arrow. In the case of FIG. 11A, when the track ball 19 is rotates in a direction between the up (U) direction and the right (R) direction, the view field direction corresponding to the operation is indicated by an arrow.

As the thus set view field direction is displayed in the display mode similar to the bending operation of the bending section, the user can easily find out the actual view field direction in the endoscope 3. For this reason, it is possible to visually easily perform the operation for setting the observation target within the field of view, and the operability can be improved.

Furthermore, the tube body needs no structure, such as the bending piece or the bending wire, for bending the tube body to change the view field direction. Therefore, it becomes easier to form the thin tube body, whereby the insertion performance can be improved and the patient burden can be reduced.

Figure 11B:
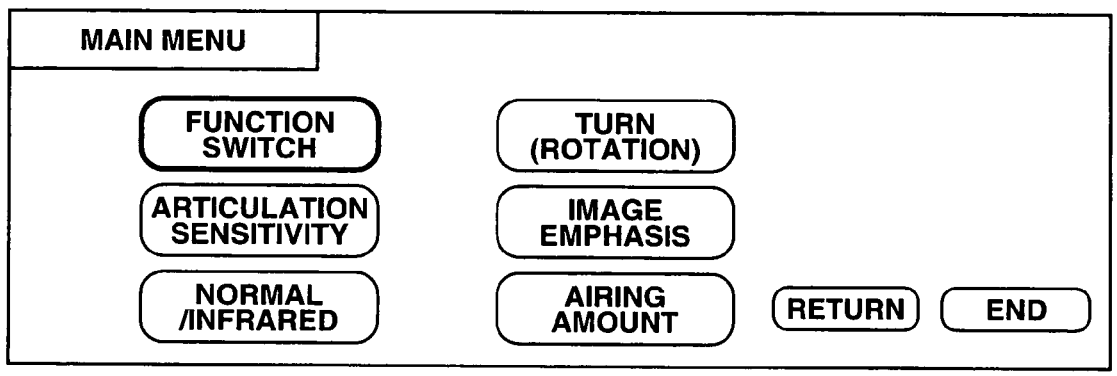
FIG. 11B shows a display example of a main menu on the monitor.
Figure 11C:
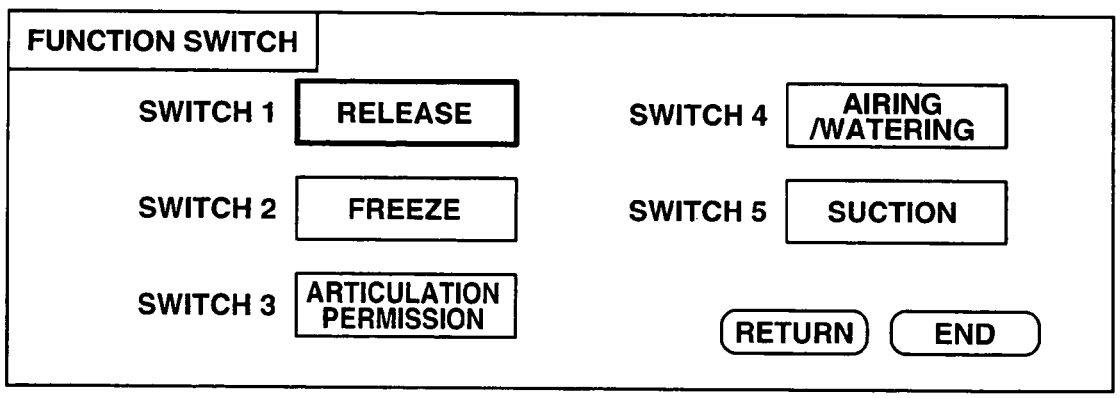
FIG. 11C shows an allocation example to function switches on the monitor.

The menu to be displayed on the menu display Rm includes a main menu shown in FIG. 11B. In this main menu, a return operation item for instructing to perform a return operation to the previous menu screen and an end item for instructing to perform a menu end operation are displayed together with the function switches, the articulation sensitivity at the time of the view field direction change, the respective settings for the normal observation and the infrared observation, the setting for the turning (rotating) sensitivity of the distal end turning actuator 41, the setting for the image emphasis in the signal processing, and the airing amount setting.

The user moves a selection frame by operating the track ball 19 or the like to select the item of, for example, the function switches, the frame of the item of the function switches is displayed in bold, indicating that the item is selected.

Moreover, by pressing the track ball 19 to confirm the operation, as shown in FIG. 1C, functions to be allocated to function switches SW1 to SW5 can be selected and set. It should be noted that the case is described in which the air water switch SW4 and the suction switch SW5 can also be allocated similarly to the function switches SW1 to SW3.

It should be noted that in other embodiments as will be described later, when other function other than the function of the capsule section 22 according to this embodiment is provided, the item for operating the function may also be allocated to the function switches SW1 to SW3 (and SW4 and SW5).

Next, operation of the endoscopic system 1 having such a structure will be described.

When the endoscopy is carried out, first of all, the endoscope 3 is connected to the AWS unit 4 to which the AWS adapter 92 is previously mounted. The connection cable 8 is connected to the operation remote controller 7, and an electrical connector 8b of the connection cable 8 is connected to the AWS unit 4.

The user connects the AWS unit 4 to the UPD coil unit 97, and connects the endoscopic system control device 5 to the observation monitor 6. Also, if necessary, the endoscopic system control device 5 is connected to an image recording unit or the like not shown, thereby completing the setup of the endoscopic system 1.

Next, power supplies of the AWS unit 4 and the endoscopic system control device 5 are turned ON. As a result, the respective sections are activated in the AWS unit 4. The power supply unit 75 can supply the endoscope 3 side with electric power via the power line 27, and also supply the operation remote controller 7 with electric power via a power supply line.

The operations at the time of activation on the AWS unit 4 and the endoscope in this case will be described with reference to FIGS. 12 and 13.

Figure 12:
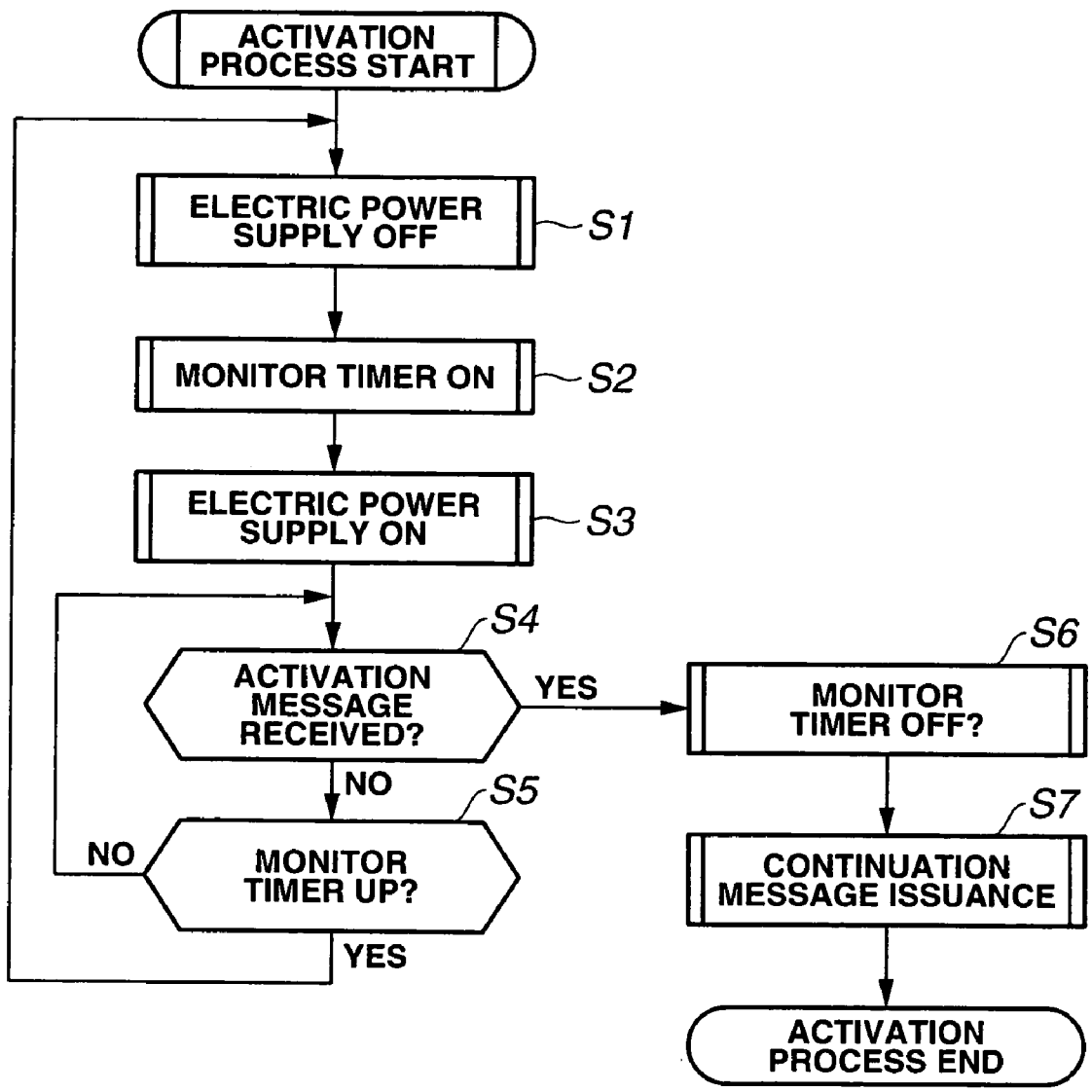
FIG. 12 is a flowchart showing a content of an activation process on the AWS unit side.

When the activation process is started, as shown in FIG. 12, first of all, in Step S1, the electric power transmission control section 128 in the power supply unit 75 of the AWS unit 4 shown in FIG. 9 puts the power supply transmission output section 127 in the electric power supply stop status, that is, the electric power supply is turned OFF.

After that, in Step S2, a monitor timer in the electric power transmission control section 128 is turned ON, and then, as shown in Step S3, the power supply transmission output section 127 is put in the electric power supply status, that is, the electric power supply is turned ON. As the power supply transmission output section 127 is in the electric power supply status, via the power line 27, the power supply circuit 44 in the control unit 45 of the endoscope 3 is supplied with the alternating current power from this electric power.

Also, the alternating current power is supplied to the power supply generating section 86 in the control circuit 57 of the operation remote controller 7.

After that, as shown in Step S4, the electric power transmission control section 128 is in a reception waiting status for an activation message via the signal line 28 from the endoscope 3 side. Then, when the activation message is not received, as shown in Step S5, the electric power transmission control section 128 judges whether or not it is running out of time in the monitor timer. In the case where time is not running out, the flow returns to Step S4, and in the case of running out of time, the flow returns to the first Step S1.

On the other hand, in Step S4, when the activation message is received before running out of time, the electric power transmission control section 128 turns the time measurement of the monitor timer OFF as shown in Step S6. Then, as shown in Step S7, the continuance message is issued, and the activation process is ended.

Meanwhile, in the control circuit 43 of the endoscope 3, as the power supply circuit 44 is supplied with the alternating current powers, necessary electric power for the operation in the control circuit 57 is supplied, and the activation process is started. Then, the status control section 81 shown in FIG. 13 waits, first of all, in Step S11, for stabilization of the power supply voltage in the power supply circuit 44.

When the power supply voltage is stabilized, in the next Step S12, the status control section 61 performs system resetting of the respective sections in the control unit 45. After the system reset, as shown in Step S13, the status control section 61 issues the activation message to the operation remote controller 7, and then in Step S14, waits for the activation message reception (of the reply message reception) from the operation remote controller 7.

Then, when the activation message reception data is received from the operation remote controller 7, as shown in Step S15, the activation message is issued to the AWS unit 4 in this time. Then, after the issuance of the activation message, as shown in Step S16, the status control section 61 waits for the continuance message reception from the electric power transmission control section 128 side. When the continuance message is received, the activation process is ended. On the other hand, when the continuance message is not received, as shown in Step S17, if a retry end condition (for example, a condition for the previously set number of retry times) is not met, the flow returns to Step S15, the activation message is reissued by the status control section 61. When the retry end condition is met, the error end is effected.

Figure 13:
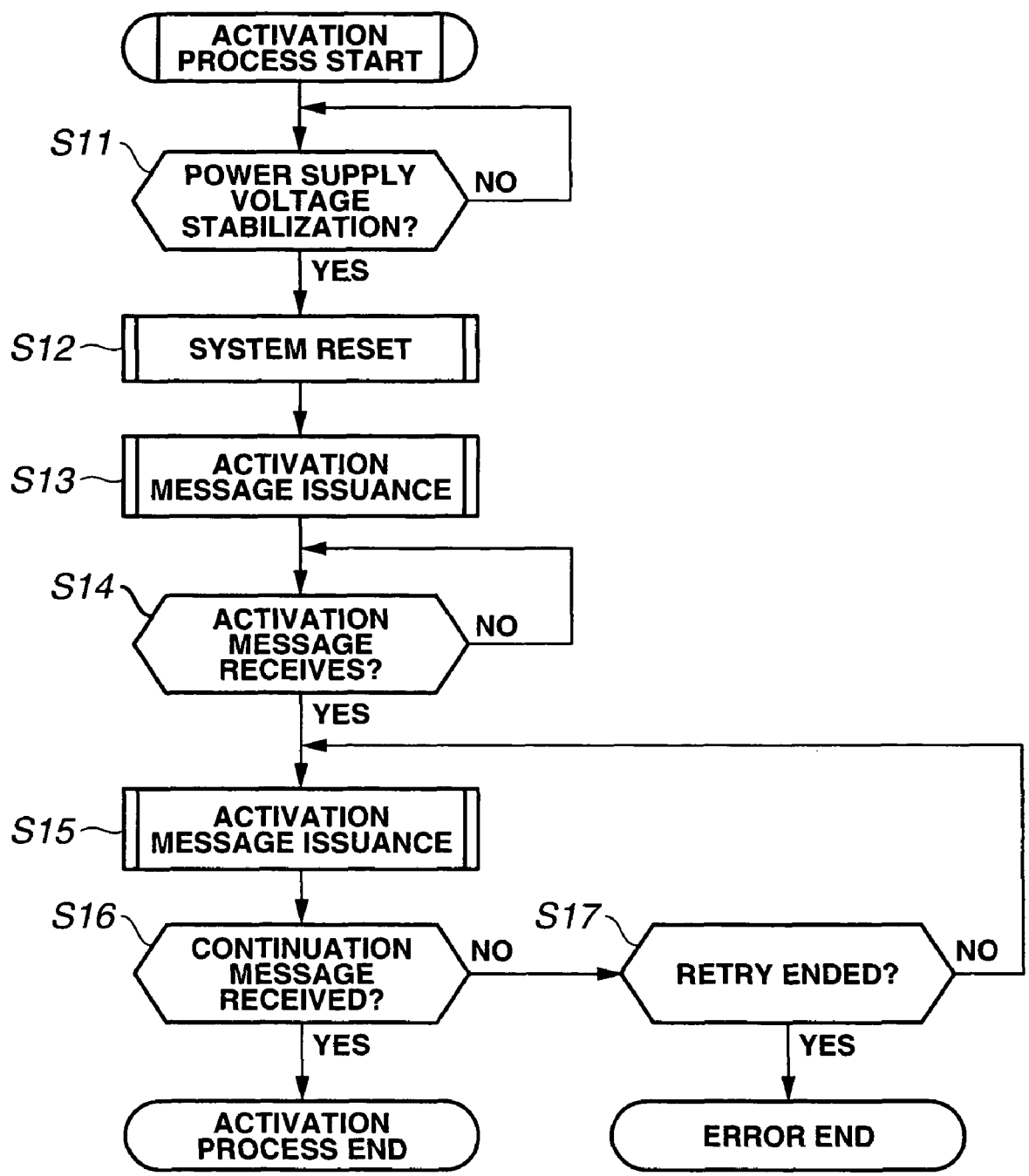
FIG. 13 is a flowchart showing a content of an activation process on the endoscope side.

While the activation process shown in FIGS. 12 and 13 is performed, also in the case where the endoscope 3 and the remote controller 7 are supplied with the alternating current power contactlessly from the AWS unit 4, the power supply operation can be performed with stability.

When the above-mentioned activation process is normally ended, image pickup by the CCD 38 is started. The user can perform the operations airing/watering and suction, articulation operation for field view varying, and the like as the operation section of the remote controller 7. Therefore, the user inserts the endoscope 3 from the distal end side into the body, and it is possible to start the endoscopy.

The endoscope 3 according to this embodiment integrally includes, in addition to the capsule section 22, the flexible insertion tube 21 functioning as an insert section significantly thinner than the outer diameter of the capsule section 22. Thus, the insertion into the body is easily performed, and at the same time the endoscopy or the therapy on the inspection target area can be much smoothly performed as compared to the case in which only the capsule section 22 is provided.

That is, in the case of the capsule section 22 without the insertion tube 21, the capsule section 22 moves under peristalsis or the like. It takes time to reach the inspection target area, and even when the capsule section reaches the inspection target area, as the capsule section moves under the peristalsis or the like, it is difficult to perform a close inspection. On the contrary, according to this embodiment, with the structure where the insertion tube 21 is integrally linked to the capsule section 22, by the operation of extruding the base end side of the insertion tube 21, the insertion into the deep side of the body can be easily performed.

In addition, it is unnecessary to provide a light guide for transmitting the illumination light to the insert section or a bending mechanism for bending the insert section unlike the normal endoscope having the insert section, whereby the diameter reduction of the tube body can be achieved, the operability can be improved, and the patient burden can be reduced. Thus, it is possible to achieve the status in which the target area can be observed in a short period of time, and at the same time if the insertion tube is held while the movement at the base end of the insertion tube 21 is restricted, the capsule section 22 at the distal end is remained in the target area, thereby making it possible to sufficiently inspect the target area.

There is a placement type as a prior art. In the case of placement, a piece corresponding to the insertion tube 21 obstructs, so the piece is removed when set in the use statue under placement. In this case, there is a drawback for example in that the observation view field has a reduced observation function due to deposit of body fluid and the problem cannot be solved. However, according to this embodiment, the reduction in observation function or the like can be prevented easily by performing airing, watering, etc.

Also, according to this embodiment, as the observation view field direction by the illumination and image pickup unit 40 can be changed, the observation function can be improved.

Figure 14:
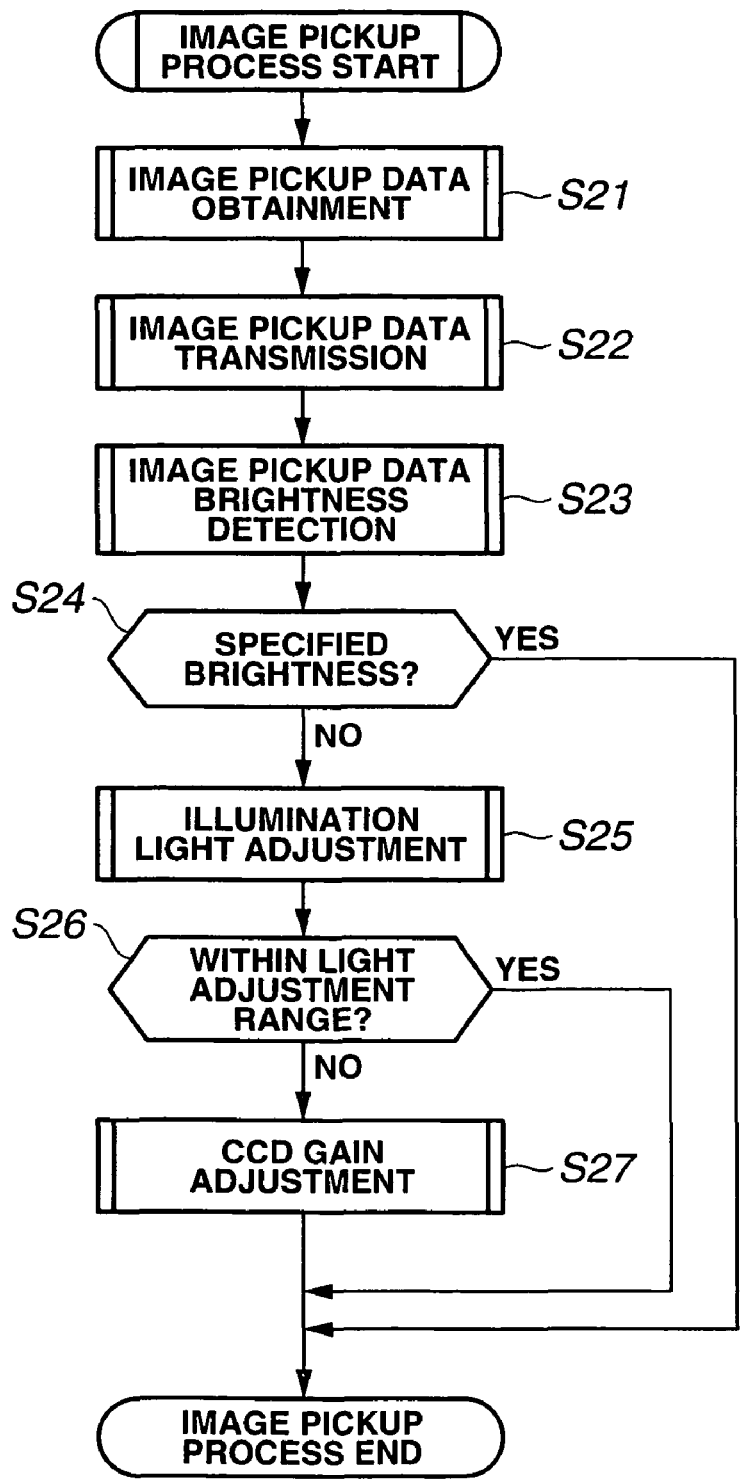
FIG. 14 is a flowchart showing a content of an image pickup process.

Representative process operations regarding these various operations will be described with reference to FIGS. 14 to 18. FIG. 14 shows an operation content of the image pickup control process.

As shown in FIG. 14, when the image pickup process is started, as shown in Step S21, the endoscope 3 obtains the image pickup data. To be specific, under the management (control) of the status control section 61, the LED 39 emits light, and at the same time the CCD driver section 66 starts an operation for driving the CCD 38. An image pickup signal captured by the CCD 38 is converted by the ADC 67 into a digital signal (image pickup data). The image pickup data (image data) is sequentially stored in the image memory 68, and the image pickup data is obtained.

The thus obtained image data is sequentially transmitted as shown in Step S22. The image data read from the image memory 68 is transmitted in a wired way from the transmission and reception unit 63A to the AWS unit 4, and further wirelessly transmitted from the transmission and reception unit 77 of the AWS unit 4 to the endoscopic system control device 5 side to be converted into a video signal inside the endoscopic system control device 5 and displayed on the observation monitor 6.

Then, the image pickup data of the ADC 67 is input to the brightness detecting section 69. As shown in Step S23, the brightness detecting section 69 calculates a mean value of the brightness data in the image pickup data over an appropriate time period or the like to detect the brightness in the image pickup data.

The detected data of the brightness detecting section 69 is input, for example, to the status control section 61, where it is judged whether or not the brightness is the instructed brightness (Step S24). Then, when the brightness is the instructed brightness, the image pickup process is ended, the flow shifts to the next image pickup process.

On the other hand, in Step S24, when the status control section 61 judges that the brightness is not the instructed brightness, as shown in Step S25, an instruction signal for illumination light adjustment (control signal) is sent to the illumination control section 64, and the illumination control section 64 adjusts the illumination light quantity. For example, the illumination control section 64 adjusts the illumination light quantity by increasing or reducing a driving current for causing the LED 39 to emit the light, or the like. The illumination control section 64 returns the adjustment result to the status control section 61.

Thus, the status control section 61 judges whether or not the brightness is in the brightness adjustment range by the illumination control section 64 on the basis of information on the adjustment result. Then, when the brightness adjustment based on the illumination control section 64 can be performed, a process in Step S27 is not performed, and the image pickup process control is ended. On the other hand, when the brightness is out of the brightness adjustment range by the illumination control section 64, as shown in Step S27, the status control section 61 outputs a CCD gain adjustment signal to the CCD driver section 66 to adjust the gain of the CCD 38, thereby adjusting the brightness of the image pickup data. Then, the image pickup process is ended. By performing the control in this way for prioritizing the adjustment by the illumination light and adjusting the observation image to have an appropriate brightness, it is possible to obtain the observation image with satisfactory S/N.

Next, an air water process of FIG. 15 will be described. As shown in FIG. 4B or the like, in general, functions of the air water switch SW4 and the suction switch SW5 are allocated on both sides of the track ball 19 in the operation remote controller 7.

Figure 15:
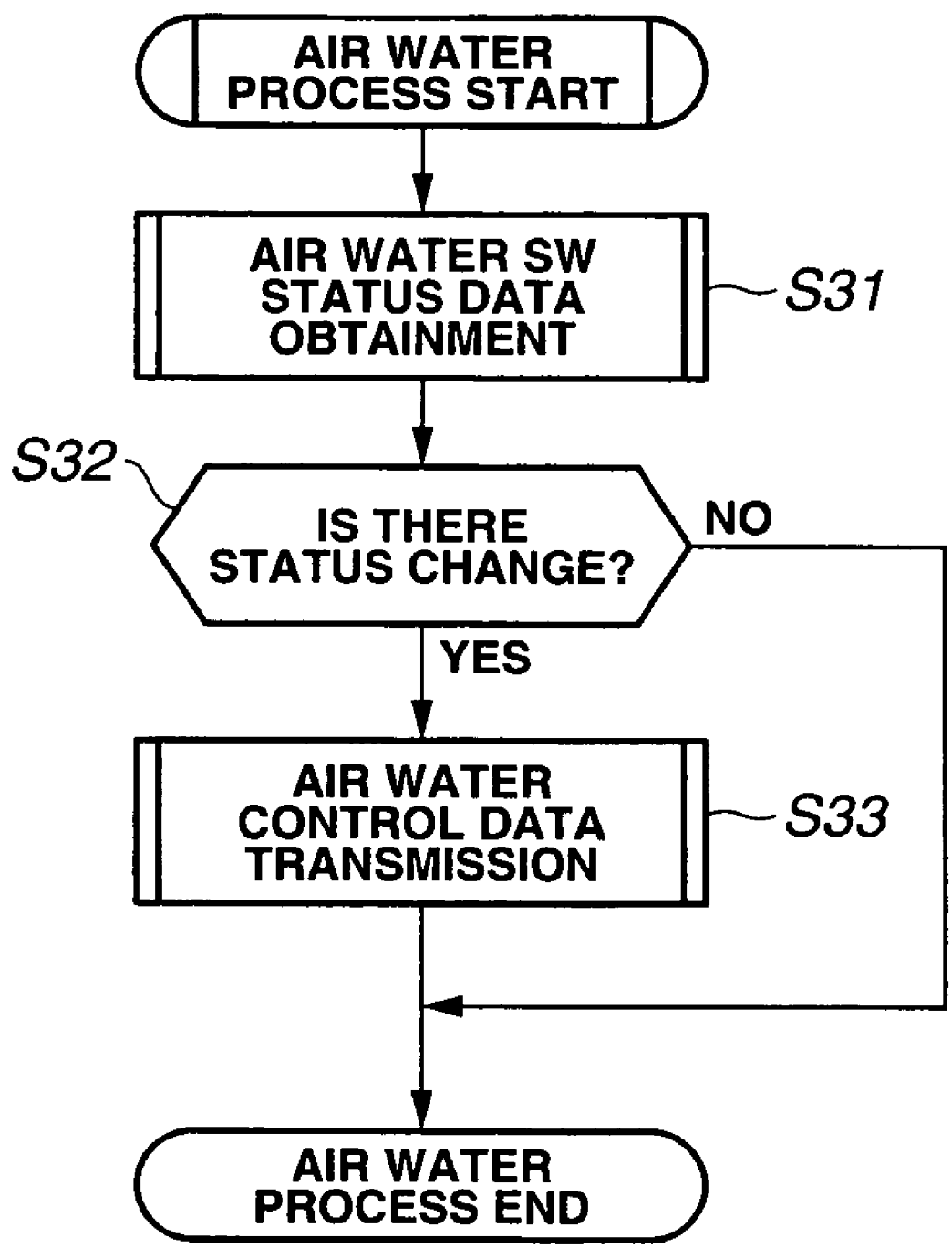
FIG. 15 is a flowchart showing a content of an air water process.

When the air water process is started, as shown in Step S31 of FIG. 15, the status control section 81 of the control circuit 57 obtains the status data of the air water switch SW4.

The operation of the air water switch SW4 is detected by the switch press detecting section 85 shown in FIG. 7. As the detection result information is input, the status control section 81 obtains the status data of the air water switch SW4.

Then, as shown in Step S32, the status control section 81 judges whether or not there is a status change in the air water switch SW4. In Step S32, when it is judged that there is a status change in the air water switch SW4, as shown in Step S33, the status control section 81 sends the air water control data corresponding to the instruction of the air water switch operated by the user, to the status control section 61 of the endoscope 3 via the transmission and reception unit 63B. The status control section 61 further uses the transmission and reception unit 63A to transmit the air water control data to the AWS unit 4 side.

The air water control section 122 in the AWS unit 4 performs the control operation for the pump 95 or the electromagnetic valve unit 124 in accordance with the air water control data. Then, the air water process operation is ended. On the other hand, in Step S32, when it is judged that there is no status change in the air water switch SW4, a process in Step S33 is not performed, and the air water process operation is ended.

According to this embodiment, the air water duct line 25 and the air water switch SW4 for performing airing or watering via the air water duct line 25 are thus provided, whereby it becomes easy to ensure the appropriate observation view field as will be described below.

For example, in the case where after the capsule section 22 is inserted in a body cavity, body fluid or the like attaches to the transparent distal end cover 32 to make a part of the observation view field (image pickup view field) by the objective lens 37 and the CCD 38 blurred or the like, thereby disturbing the observation, the air water switch SW4 is operated to deliver water in the watering tank 98 from the distal end opening via the air water duct line 25 to the outer surface of the distal end cover 32.

Then, the body fluid or the like attached to the outer surface which disturbs the observation can be easily washed off. If necessary, by further airing, the delivered water is blow off or the like to ensure the observation view field which is not affected by the body fluid or the like.

It should be noted that in the case of the air water process described above, when it is judged that there is a status change in the air water switch SW4 on the basis of the detection result of the switch press detecting section 85, the status control section 81 on the operation remote controller 7 sends the information to the status control section 61 of the endoscope 3, and the information from the status control section 61 to the AWS unit 4 side.

Instead of this method, the status control section 81 on the operation remote controller 7 sends information on a switch press detecting section 84 at a predetermined timing to the status control section 61 of the endoscope 3, and the status control section 61 of the endoscope 3 may perform the status management in a concentrated manner.

In FIG. 15, the air water process has been described. The suction process is almost the same operation as the air water process, so the operation in a flowchart will be omitted.

According to this embodiment, as described above, the suction duct line 26 and the suction switch SW5 for performing suction via the suction duct line 26 are provided. For example, when the body fluid disturbs the observation view field, by operating the suction switch SW5, the body fluid can be sucked from the distal end opening of the suction duct line 26 to be removed. As a result, the appropriate observation view field can be ensured.

Also, as the biopsy port 30 in communication with the suction duct line 26 is provided, the surgeon inserts the endo-therapy product from the biopsy port 30. A distal end of the endo-therapy product is caused to protrude from the distal end opening of the suction duct line 26 with respect to an affected area that is a therapy target in the observation view field by the objective lens 37 and the CCD 38. Then, such a therapy can also be conducted that an affected area tissue is collected and the collected tissue is inspected in detail or the affected area tissue is resected by a resecting endo-therapy product.

Moreover, in this case, the direction of the distal end side of the endo-therapy product protruding from the distal end opening of the suction duct line 26 can also be restricted or variably controlled by driving the distal end turning actuator 41, and thus the function of a therapy such as a biopsy can be improved.

In this way, according to this embodiment, as the air water duct line 25 and the suction duct line 26 are provided in the insertion tube 21, and the each distal end side penetrates through the capsule section 22 to have an opening on the outer surface, the treatment for airing and watering, the treatment for suction, and the diagnosis or therapy treatment based on the endo-therapy product insertion can be conducted, whereby it is possible to perform the more appropriate endoscopy and treatment.

Figure 16:
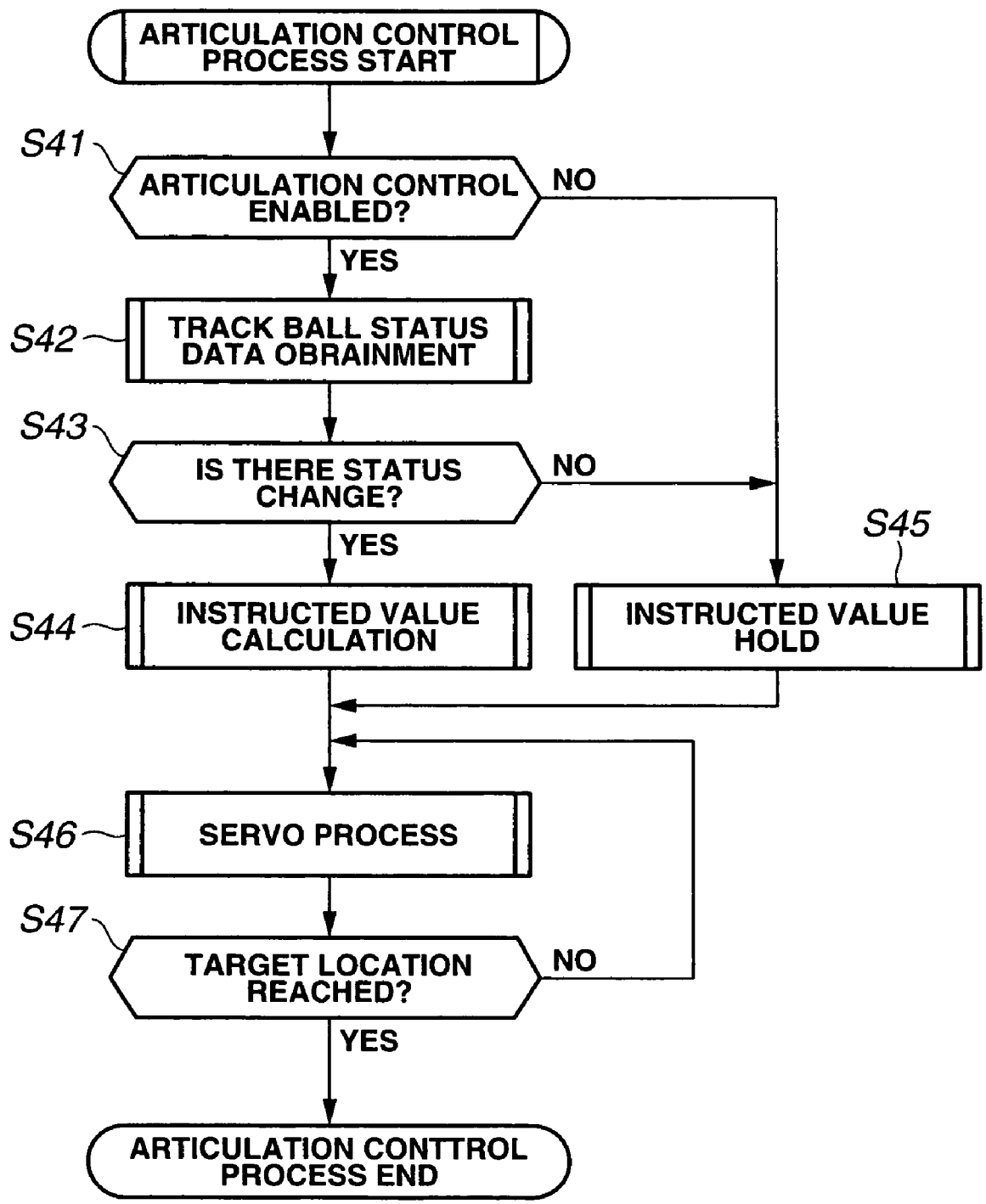
FIG. 16 is a flowchart showing a content of an articulation control process for setting a direction of view variable.

Next, with reference to FIG. 16, a process for controlling the view field varying articulation operation will be described. When the articulation control is started, as shown in Step S41, the status control section 81 judges whether or not the articulation control is enabled.

According to this embodiment, regarding the track ball 19, the status control section 81 judges whether or not the articulation control is enabled as shown in Step S41 on the basis of whether or not the track ball 19 is pressed. To be specific, the status control section 81 can detect the displacement operation and the press operation of the track ball 19 on the basis of the output of the track ball displacement detecting section 84. It should be noted that when the track ball 19 is pressed, the articulation control is turned OFF.

The status control section 81 judges whether or not the articulation control is enabled on the basis of the output of the track ball displacement detecting section 84.

Then, when it is judged that the articulation control is not enabled, the flow shifts to Step S45, where an instructed value of the previous view field change is held. On the other hand, when it is judged that the articulation control is enabled, the flow proceeds to the next Step S42, where the status control section 81 obtains the status data based on the operation of the track ball 19. Then, in the next Step S43, the status control section 81 judges whether or not there is a further status change on the basis of the output of the track ball displacement detecting section 84.

In this case, regarding the status control section 81, when it is judged that there is no status change, the flow shifts to Step S45. On the other hand, when it is judged that there is a status change, in the next Step S44, an instructed value corresponding to the rotation direction and the rotation amount of the track ball 19 is calculated.

After the process in Step S44 or S45, as shown in Step S46, the status control section 81 sends the instructed value to the status control section 61 of the endoscope 3. The status control section 61 sends the instructed value via the articulation control section 71 to the actuator driver section 72 to perform the servo process on the view field varying articulation actuator 36.

That is, the actuator driver section 72 drives the view field varying articulation actuator 36 so that an articulation angle (view field direction) corresponding to the instructed value is obtained on the basis of the instructed value. At that time, the articulation status of the view field varying articulation actuator 36 is detected by the encoder 51, and it is judged whether or not the target view field direction is reached in which the value detected by the encoder 51 corresponds to the instructed value (Step S47).

When it is judged that the target view field direction is not reached, the flow returns to Step S46. The actuator driver section 72 drives the view field varying articulation actuator 36 so that the target view field direction is reached. When the target view field direction is reached, this articulation control process is ended.

Next, the process content of a human interface integrating the above-described control processes in FIGS. 14 to 16 (including the operation remote controller 7) on the endoscope 3 side and on the endoscopic system control device 5 side will be described with reference to FIGS. 17 and 18. It should be noted that in the drawings, the human interface is abbreviated as HMI.

Figure 17:
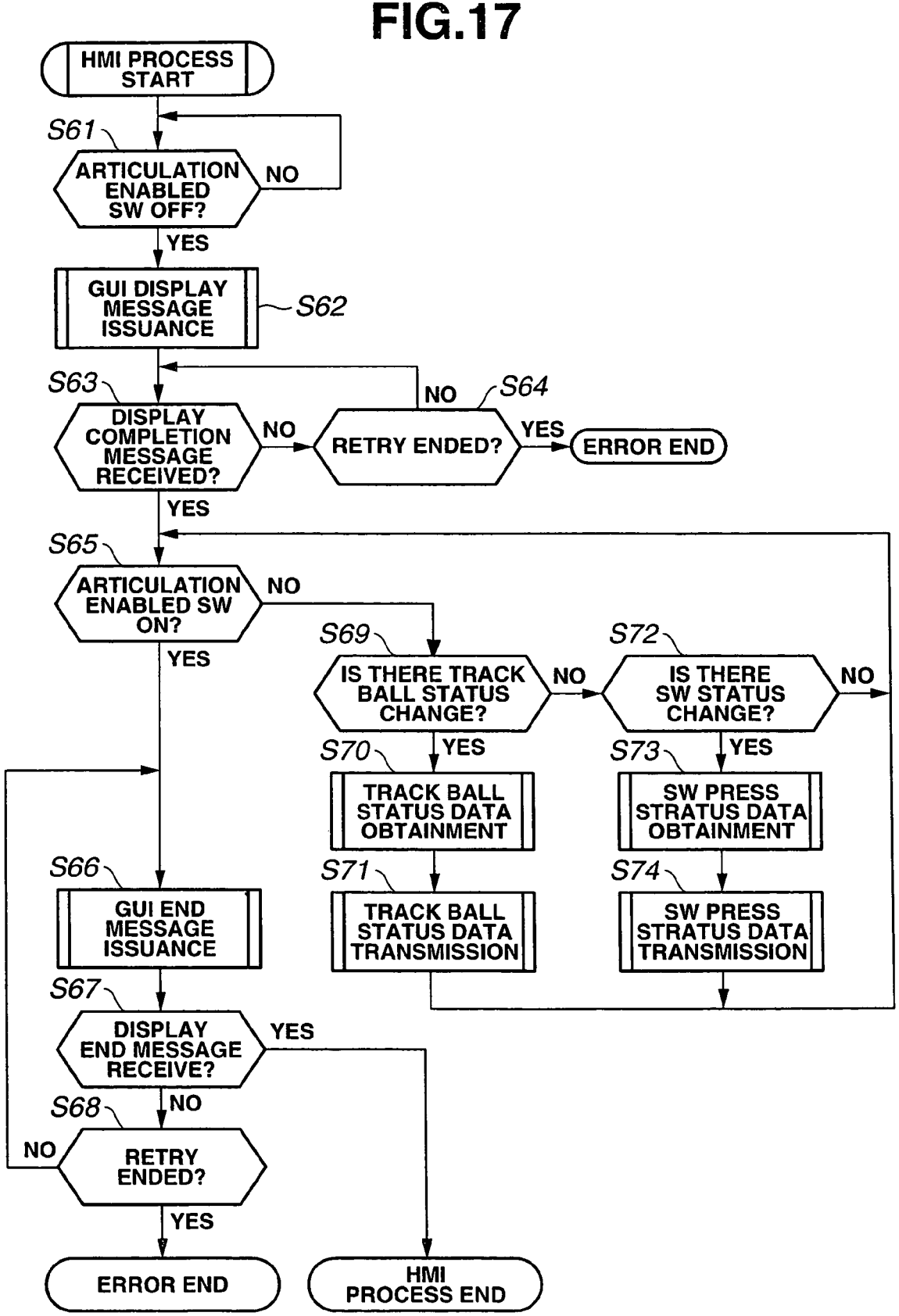
FIG. 17 is a flowchart showing a content of a process in a human interface on the endoscopic system control device side.

As shown in FIG. 17, when the human interface process is started, the status control section 61 of the endoscope 3 waits for a moment in which an articulation enabled switch is turned OFF (through the status control section 81 of the operation remote controller 7). That is, the status control section 61 of the endoscope 3 waits for a moment in which the articulation enabled switch is turned OFF after the track ball 19 is pressed.

Then, when the articulation enabled switch is turned OFF, as shown in the next Step S62, the status control section 61 issues a GUI (graphical user interface) display message. This GUI display message is wirelessly sent from the endoscope 3 via the AWS unit 4 to a CPU (control CPU) in a system control unit 117 of the endoscopic system control device 5.

After the status control section 61 issues the GUI display message, in the next Step S63, the status control section 61 waits for the GUI display completion message reception from the endoscopic system control device 5 side. Then, when the GUI display completion message cannot be received, the flow proceeds to Step S64, where the status control section 61 judges whether or not this is corresponding to a retry end condition. When this is not corresponding to the retry end condition, the flow returns to Step S63, and on the other hand when this is corresponding to the retry end condition, the error end is effected.

When the display completion message is received in the process in Step S63, the flow shifts to Step S65, and the status control section 61 judges whether or not the articulation enabled switch is turned ON (through the status control section 81 of the operation remote controller 7). When the articulation enabled switch is turned ON the status control section 61 issues a GUI end message as shown in Step S66.

The GUI end message is sent wirelessly via the AWS unit 4 to the endoscopic system control device 5 similar to the case of the GUI display message from the endoscope 3. Then, after issuing the GUI end message, the status control section 61 waits for a GUI display end message reception from the endoscopic system control device 5 side in the next Step S67. When this GUI display end message is received, the status control section 61 terminates this human interface process.

On the other hand, when this GUI display end message cannot be received, the flow proceeds to Step S68, where the status control section 61 judges whether or not this is corresponding to the retry end condition. When this is not corresponding to the retry end condition, the flow returns to Step S66, and on the other hand when this is corresponding to the retry end condition, the error end is effected.

Furthermore, in Step S65, when the articulation enabled switch is not turned ON, the flow shifts to the process in the menu screen on the Step S69 side. In this Step S69, the status control section 61 judges whether or not there is a status change in the track ball 19 on the basis of whether or not there is a change amount equal to or larger than a certain threshold from the output of the track ball displacement detecting section 84.

Then, as shown in Step S70, when it is judged that there is a change regarding the status in the track ball 19 (through the status control section 81 of the operation remote controller 7), the status control section 61 obtains the status data of the track ball 19 (change data)

In this case, the user can select and instruct a desired function of the item with use of a cursor moving in accordance with the operation of the track ball 19 on the menu screen in FIG. 11B.

Then, as shown in Step S71, the status control section 61 transmits the status data corresponding to the operation of the track ball 19 by the user. The status data is transmitted as packet data in sync with the image pickup data of the CCD 38 from the endoscope 3 via the AWS unit 4 to the endoscopic system control device 5. After the transmission of the status data, the flow returns to the process in Step S65.

In Step S69, when it is judged that there is no change in the status of the track ball 19, as shown in Step S72, the status control section 61 judges whether or not there is a change in the switch status (the switches SW1 to SW5) on the basis of the detection output from the switch press detecting section 85 (through the status control section 81 of the operation remote controller 7).

In Step S72, when there is no change in the switch status, the flow returns to Step S65, and on the other hand when there is a change in the switch status, as shown in Step S73, the status control section 61 obtains the switch press status data. Furthermore, in the next Step S74, the thus obtained switch press data is transmitted, whereby the flow returns to the process in Step S65.

Figure 18:
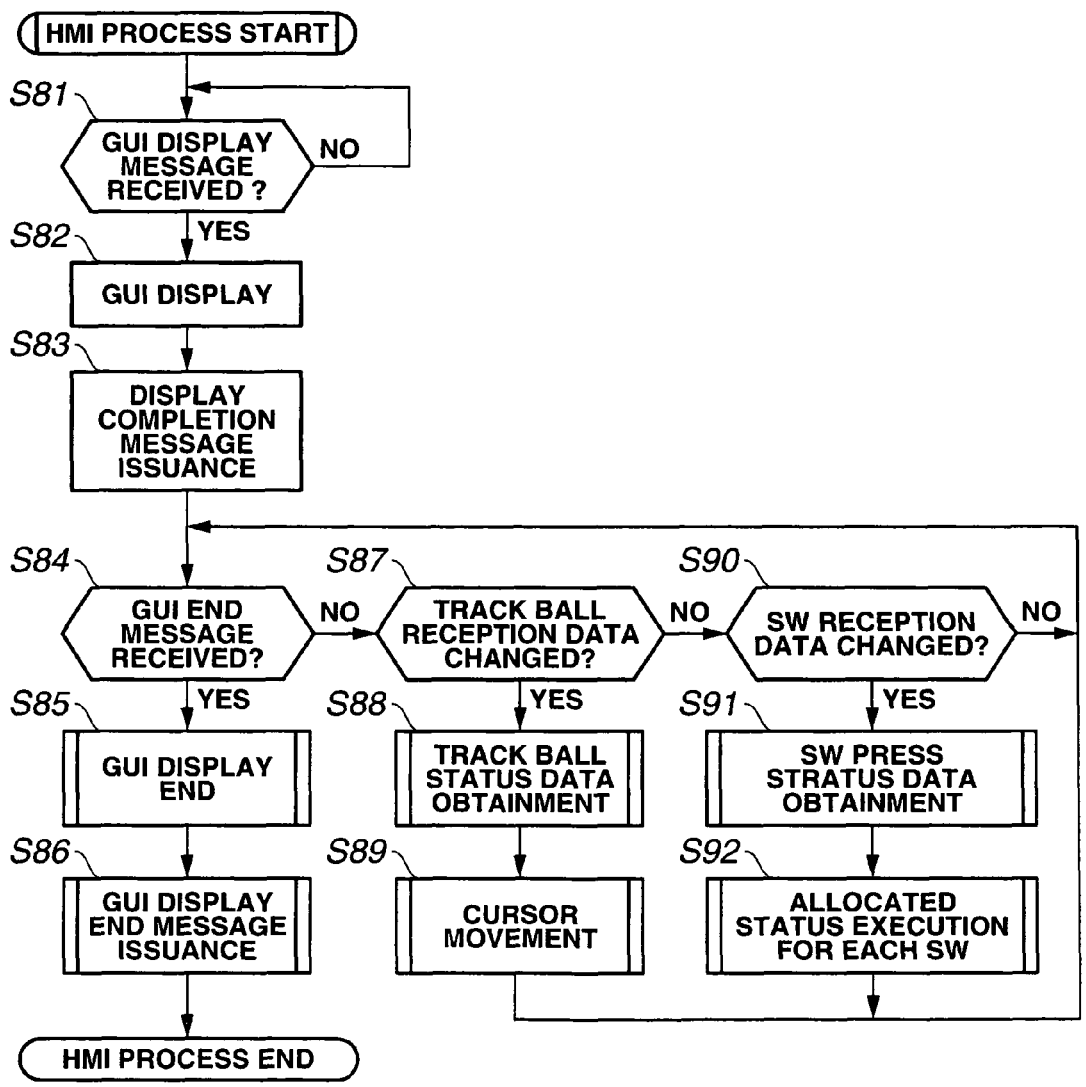
FIG. 18 is a flowchart showing a content of a process in the human interface on the endoscope side.

On the other hand, as shown in FIG. 18, when the human interface process is started, the CPU of the system control unit 117 in the endoscopic system control device 5, in the first Step S81, waits for the GUI display message reception from the endoscope 3 side. The CPU waits for the wireless GUI display message reception via the transmission and reception unit 101 of FIG. 8 or 10.

Then, as shown in Step S82, the CPU of the system control unit 117 performs the control process for the GUI display when the GUI display message is received. That is, the CPU performs the control for the GUI display with respect to the image processing unit 116.

After the GUI display process in Step S82, as shown in Step S83, the CPU issues a display completion message. The CPU transmits this display completion message via the transmission and reception unit 101. In the next Step S84, the CPU judges whether or not the GUI end message is received from the endoscope 3 side. Then, when the GUI end message is received, in Step S85, the CPU performs a process for ending the GUI display. After that, in the next Step S86, the CPU further issues a GUI display end message, and thereafter the human interface process is ended.

In Step S84, when the GUI end message is not received, the flow shifts to Step S87, where the CPU judges whether or not there is a change in the reception data of the track ball 19. The judgment as to whether or not there is a change in the reception data of the track ball 19 is performed in response to reception of the judgment result of the endoscope 3 side (including the operation remote controller 7) as to whether or not there is a status change in the track ball 19.

Then, when it is judged that there is a change in the reception data, as shown in Step S88, the status data of the track ball 19 is obtained. Furthermore, in the next Step S89, the CPU moves the cursor by the movement amount corresponding to the thus obtained status data of the track ball 19 (change data). Then, the flow returns to the process in Step S84.

On the other hand, in the process in Step S87, when it is judged that there is no change in the reception data of the track ball 19, the CPU judges whether or not there is a change in the reception data of the switch as shown in Step S90, on the basis of the transmitted information on the judgment result on the endoscope 3 side.

Then, there is a change in the reception data of the switch as shown in Step S91, the CPU obtains the switch press status data on the basis of the transmitted information from the endoscope 3 side. Furthermore, as shown in Step S92, the CPU performs a process for executing the function allocated to the switch, which has been pressed, and the flow returns to the process in Step S84. Also there is no change in the reception data of the switch in Step S90, the flow returns to the process in Step S84.

With the endoscope 3 according to this embodiment which forms the endoscopic system 1 for performing the above-mentioned operations, the duct line for performing airing/watering or suction and the insert section for the endo-therapy product are provided in the flexible insertion tube 21, the endoscopy or the diagnosis can be performed more appropriately.

Also, with the endoscope 3 according to this embodiment for performing the above-mentioned operations, such a structure is provided in which the view field direction of the observation section composed of the illumination and image pickup section can be changed and set (changing operation) to an arbitrary angle within a range of predetermined angles. Thus, by controlling the operation remote controller 7, the view field direction can be set in a desired direction, and the tube body does not need a structure for bending the tube body or a light guide for transmitting the illumination light, so while the diameter reduction of the tube body is achieved, the observation function can be significantly improved.

More specifically, the first base member 33 to which the illumination and the image pickup unit 40 is attached can face in the desired direction (with respect to the second base member 34) by driving the view field varying articulation actuator 36 to change the inclination angle.

Moreover, together with the first base member 33, the second base member 34 is held freely turnable about the center axis O with respect to the third base member 35 by the distal end turning actuator 41. By the operation of the operation remote controller 7, the distal end turning actuator 41 is driven to change the turning angle of the second base member 34 side, thereby causing the observation section to face the desired direction.

For this reason, as the operation for changing the inclination angle and the operation for changing the turning angle are performed by the operation remote controller 7, it is possible to approach the inspection target area or the diagnosis target area in various directions, so the observation function can be significantly improved as compared to the prior art.

In addition, according to this embodiment, the electric connector 46 of the connector 23 on the distal end side of the endoscope 3 has a structure for detachable connection in a contactless manner. Thus, even when the endoscope 3 is subjected to repeated washing or sterilization, no contract conduction failure or the like is generated unlike the case in which the contact is not a contactless contact, thereby improving the reliability.

Also, the operation remote controller 7 has a structure for detachable connection in a contactless manner. Thus, even when the operation remote controller 7 is subjected to repeated washing or sterilization, no contract conduction failure or the like is generated unlike the case in which the contact is not a contactless contact, thereby improving the reliability.

In the endoscope 3 according to this embodiment, the electric connector 46 in the connector 23 has a contactless structure, but as a modified example, the electric connector 46 may have a structure including an electric contact.

It should be noted that in the above description, the endoscope 3 includes the dedicated transmission and reception units 63A and 63B for performing the wired data transmission and reception with the AWS unit 4 and the operation remote controller 7. However, as a modified example, one common transmission and reception unit may be provided for performing the wired data transmission and reception with the AWS unit 4 and the operation remote controller 7.

In this case, in general, the endoscope 3 may be set in such a status that transmission and reception are performed with the AWS unit 4 so that image data with large data transmission amount can be efficiently transmitted, so that transmission and reception of data on the operation information are performed with the operation remote controller 7 in a time-sharing mode.

Second Embodiment

Next, with reference to FIGS. 19A to 21, a second embodiment of the present invention will be described.

Figure 19A:
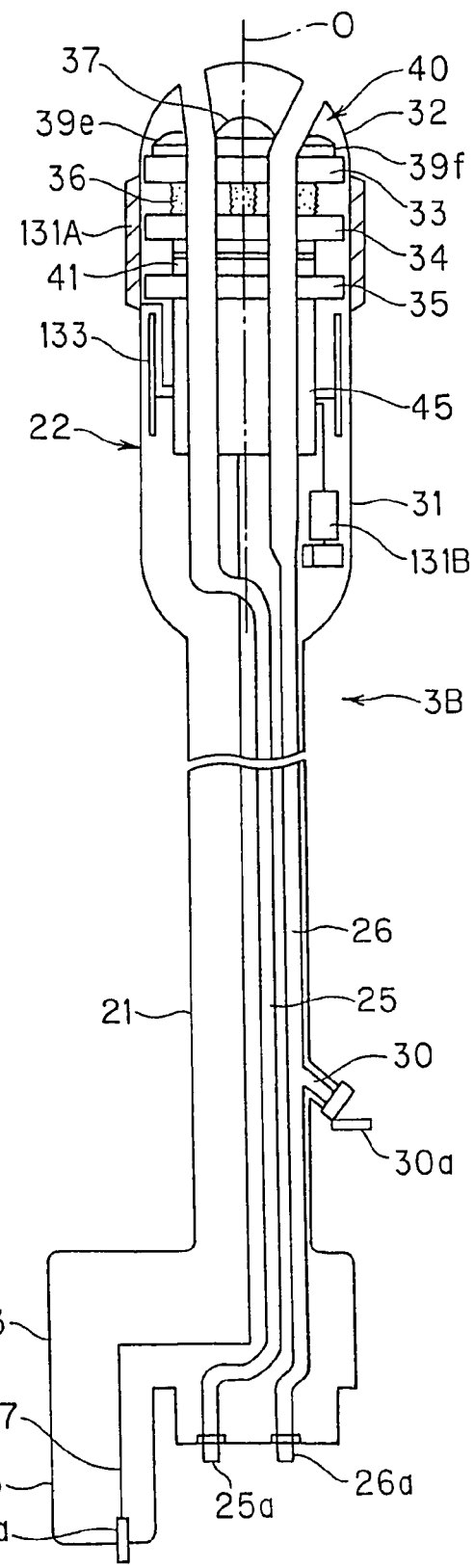
FIG. 19A shows an entire structure of an endoscope according to a second embodiment of the present invention.
Figure 19B:
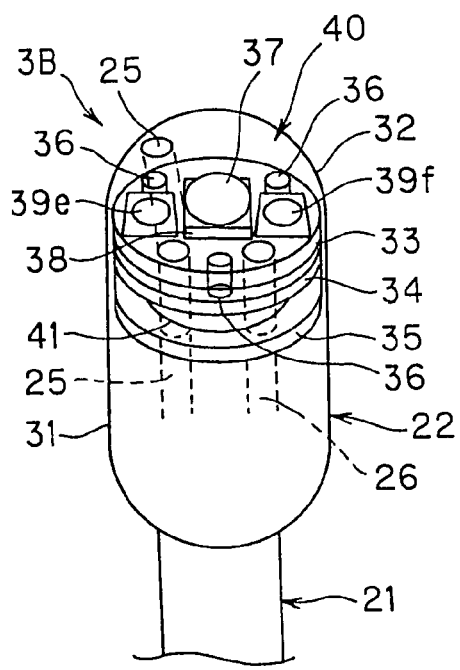
FIG. 19B shows a part of the endoscope at a distal end according to the second embodiment of the present invention.

FIG. 19A show an endoscope 3B according to the second embodiment of the present invention. Then, FIG. 19B is a perspective view of a distal end side in FIG. 19A, showing the internal structure on the distal end side of the capsule section 22.

The endoscope 3B adopts, for example, two white LEDs 39e and 39f, instead of the four illumination sections: the R-LED 39a, the G-LED 39b, the B-LED 39c, and the IR-LED 39d in the endoscope 3 of FIG. 3A, with a structure for performing the normal observation in a visible area.

In addition, the endoscope 3B according to this embodiment includes, for example, a vibration actuator (vibration unit) 131A having an annular shape piezoelectric oscillator on the outer circumference surface of the distal end section of the capsule section 22 (or the inner circumference surface may be used). For example, the vibration actuator 131A is connected to the control circuit 43 not shown in the drawing here which is provided in the control unit 45 inside the capsule section 22 via a signal line.

A vibration actuator 131B composed of a vibrating motor or the like is eccentrically accommodated on the rear end section side inside the capsule section 22, and the vibration actuator 131B is also connected to the control circuit 43 in the control unit 45 via the signal line.

Also, according to this embodiment, instead of providing the signal lines 28 and 29 in the first embodiment, an antenna section 133 for performing transmission and reception is provided in the capsule section 22. Via the antenna section 133, transmission and reception of a signal between the operation remote controller 7 and the AWS unit 4 are performed. It should be noted that according to this embodiment, such a structure is adopted that the UPD coils 49 and the UPD coil driver sections 50 in the first embodiment are not provided.

Furthermore, according to this embodiment, the power line 27 inserted in the insertion tube 21 is connected to an electric contact of the electric connector 46 in the connector 23. The other structure is the same as that of the first embodiment.

It should be noted that the power supply generating section 86 the operation remote controller 7 may be composed of a charging battery and a charging circuit, and the connection cable 8 may not be used. In this modified example, when the operation remote controller 7 is unused, the power supplied via the connection cable 8 is received by the power supply transmission and reception section, whereby the battery becomes rechargeable.

Figure 20B:
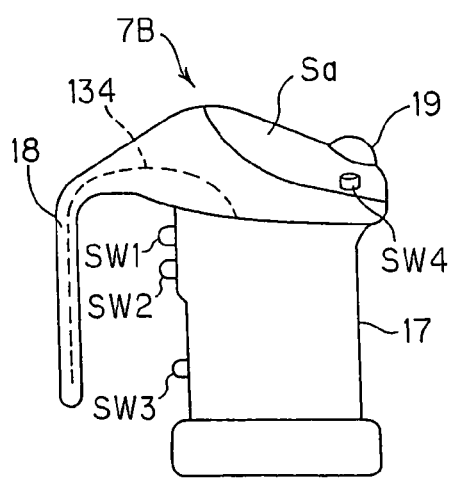
FIG. 20B shows a modification example of the operation remote controller.
Figure 20A:
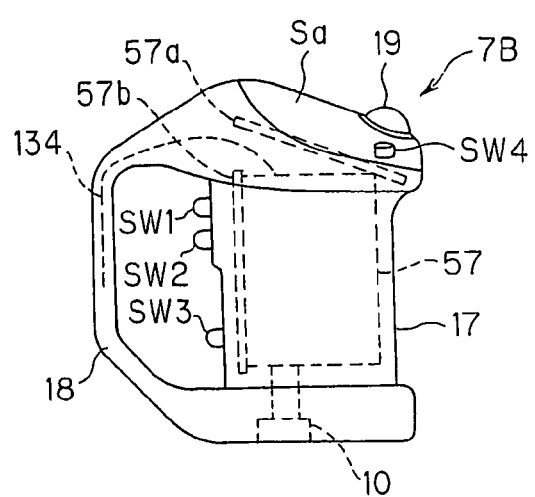
FIG. 20A shows the operation remote controller.

FIG. 20A shows an operation remote controller 7B used together with the endoscope 3B according to this embodiment.

The operation remote controller 7B has the outer shape similar to that of the operation remote controller 7 shown in FIG. 4A or the like. For the inside, as shown by a dotted line, an antenna section 134 for transmission and reception is arranged along the hook 18 from the control circuit 57. That is, along the extending direction in the hook 18, the antenna section 134 is arranged therein.

Then, the operation remote controller 7B performs wireless transmission and reception of data such as the operation information with the endoscope 3B by using the antenna section 134. It should be noted that similarly to the case of the hook 18 shown in FIG. 5B, as shown in FIG. 20B, the antenna section 134 may be provided inside the hook 18.

Figure 21:
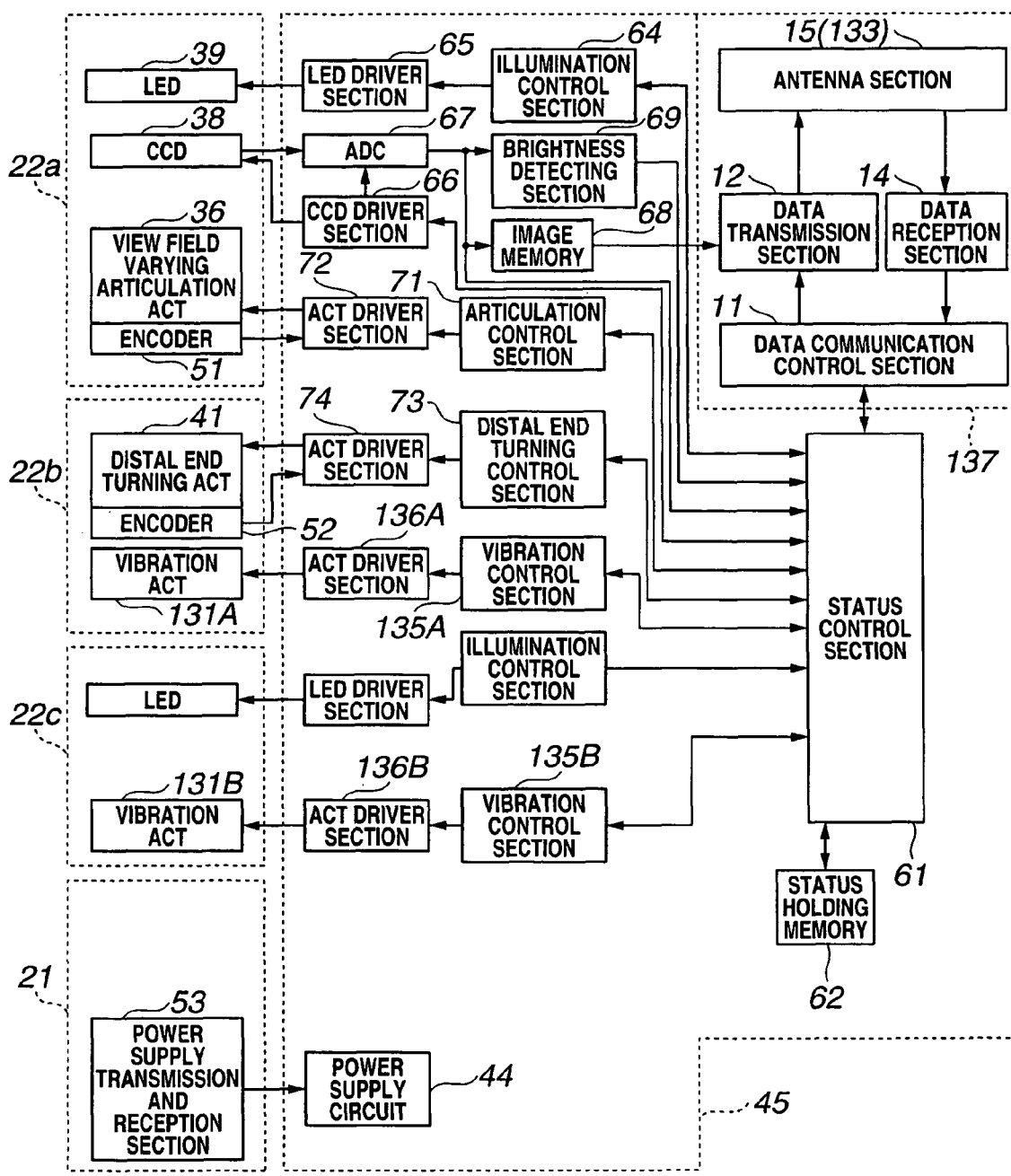
FIG. 21 is a block diagram showing the electrical system configuration of the endoscope.

FIG. 21 shows a structure of an electrical system of the endoscope 3B. The structure shown in FIG. 21 further includes a vibration actuator 131A at the distal end portion 22a of the capsule section 22 in the structure shown in FIG. 6.

In addition, the vibration actuator 131B is arranged at a rear end section 22c in the capsule section 22.

Then, the status control section 61 drives the vibration actuator 131A via a vibration control section 135A and an actuator driver section 136A.

The status control section 61 also drives the vibration actuator 131B via a vibration control section 135B and an actuator driver section 136B.

Figure 6:
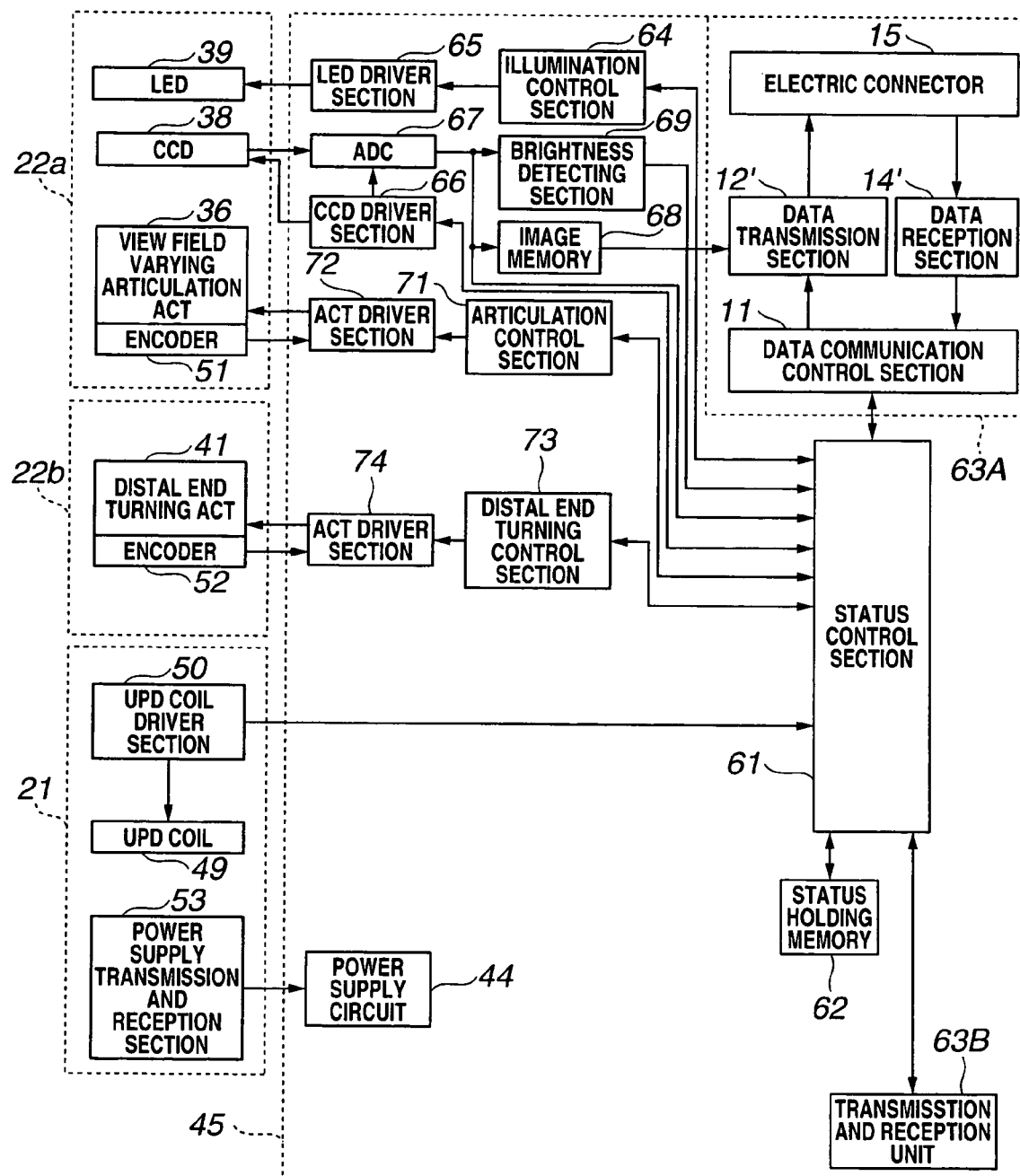
FIG. 6 is a block diagram showing an electrical system configuration of the endoscope.

Then, instead of the transmission and reception units 63A and 63B in FIG. 6, a transmission and reception unit 137 for wirelessly performing transmission and reception is provided. The transmission and reception unit 137 is relevant to FIG. 2A. The transmission and reception unit 137 adopts the antenna section 133.

It should be noted that in FIG. 21, such a structure is adopted that the UPD coils 49 and the UPD coil driver sections 50 shown in FIG. 6 are not provided. Other structure is the same as that of FIG. 6.

Figure 22:
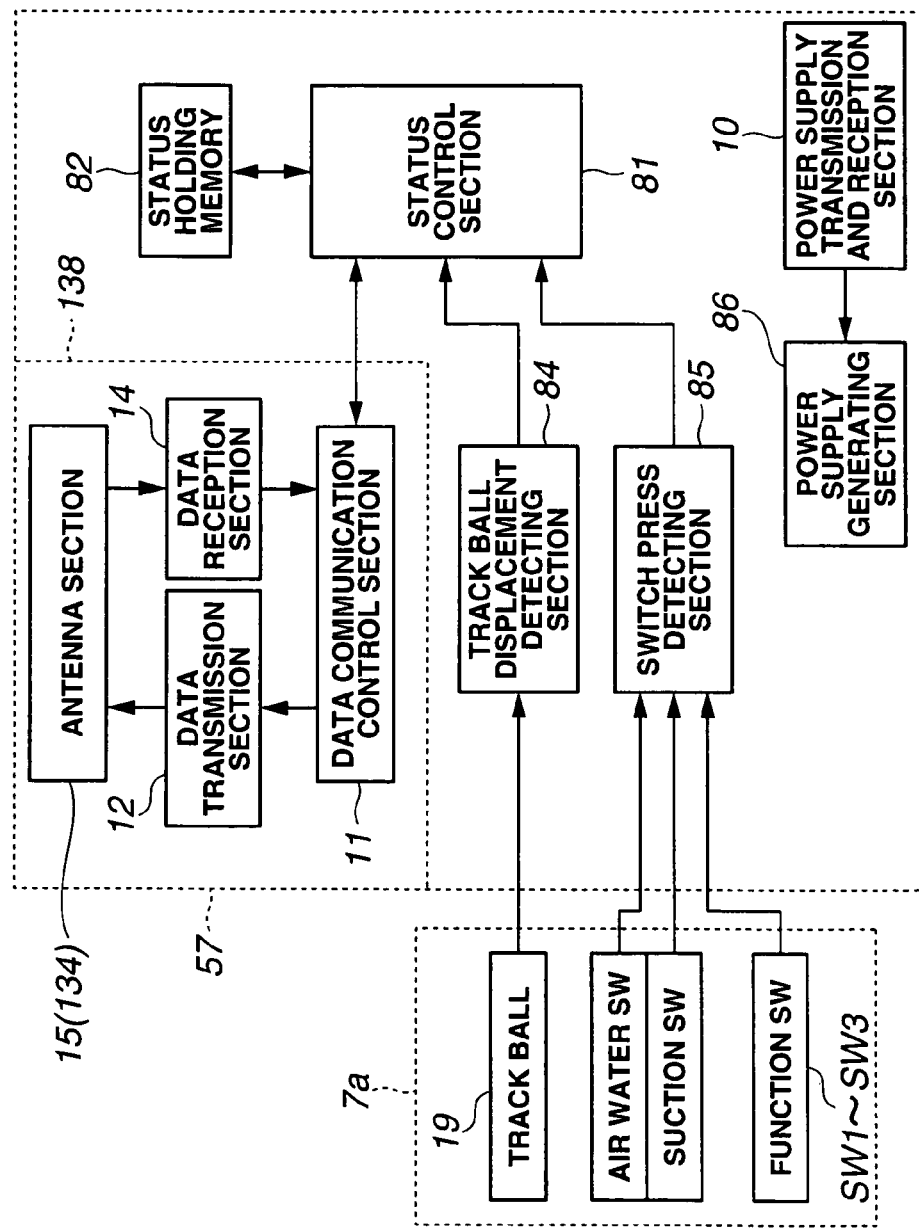
FIG. 22 is a block diagram showing the electrical system configuration of the operation remote controller.

Then, FIG. 22 shows a structure of an electrical system of the operation remote controller 7B. A structure of an electrical system of the operation remote controller 7B includes a wireless transmission and reception unit 138 instead of the wired transmission and reception unit 83 in the structure of FIG. 7. The transmission and reception unit 138 adopts an antenna section 134.

It should be noted that as operation functions of the vibration actuators 131A and 131B are allocated to the function switches SW1 to SW3, by operating the function switches to which the functions are allocated, the capsule section 22 can be vibrated. Other structure is the same as that of FIG. 7.

According to this embodiment, with the provision of the vibration actuators 131A and 131B, when a part of a distal end of the capsule section 22 is fitted into, for example, a local convex portion and the smooth insertion cannot be performed by merely performing an operation for pushing towards the front, by performing the vibrating operation for the vibration actuator 131A or 131B, the capsule section 22 is also vibrated, and therefore becomes easy to be removed from the convex portion, and thus the smooth insertion and the like can be realized.

Except for the obtainment of the UPD image by using the UPD coils 49 in the first embodiment, almost the same effect can be attained as compared with the first embodiment.

Third Embodiment

Next, with reference to FIGS. 23A to 24, a third embodiment of the present invention will be described.

FIGS. 23A and 23B show an endoscope 3C according to the third embodiment of the present invention. In the endoscope 3C, the rear end section side of the exterior body 31 of the capsule section 22 is also made of a transparent material unlike the endoscope 3 of FIG. 3A, and a base member 140 is provided in the rear end section.

On a back side of the base member 140, for example, a white LED 141 for the back side illumination, and an objective lens 38B for performing image pickup under the illumination of the white LED 142 and a CCD 38B are attached, thereby forming a rear side illumination and image pickup unit 40B. The CCD 38B is also a CCD having a gain variable function in a CCD element.

In this way, according to this embodiment, the illumination and image pickup unit 40 for performing illumination and image pickup on the front side (inside the body cavity) is provided on the distal end side of the capsule section 22. Furthermore, the rear side illumination and image pickup unit 40B for performing illumination and image pickup on the back side (inside the body cavity) is provided on the back side of the capsule section 22.

Also, according to this embodiment, similarly to the second embodiment (not using the signal lines 28 and 29 in the first embodiment), the antenna section 133 for transmission and reception is provided in the capsule section 22. According to this embodiment, for example, such a structure is adopted that the UPD coils 49 and the UPD coil driver sections 50 are not built in. Other structure is the same as that of the first embodiment.

Figure 24:
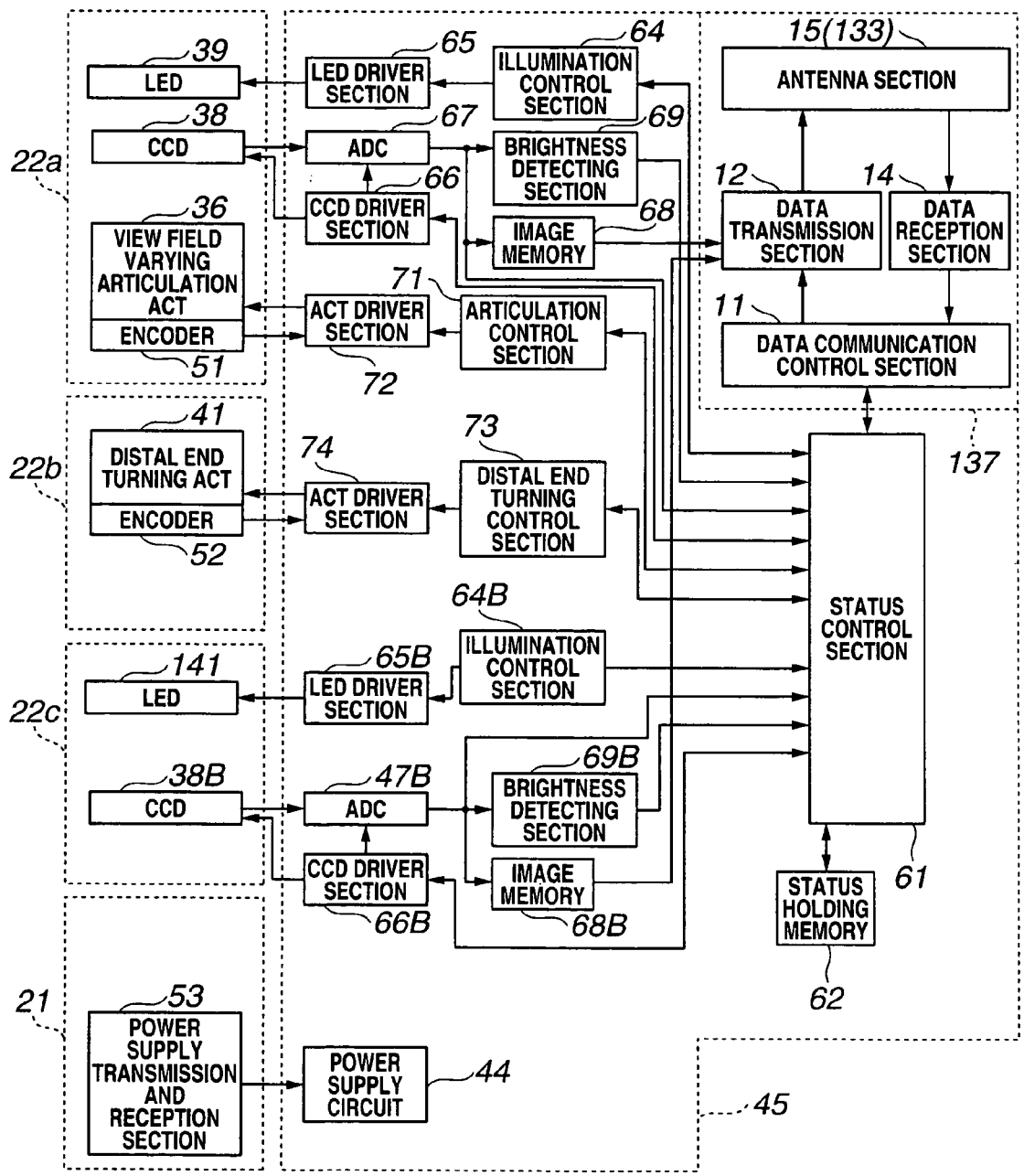
FIG. 24 is a block diagram showing the electrical system configuration of the endoscope.

FIG. 24 shows a structure of an electrical system of the endoscope 3C. The structure shown in FIG. 24 further includes an LED 141 and a CCD 38B arranged in a rear end section 22c in the capsule section 22 as compared with the structure shown in FIG. 6.

Also, as described in the second embodiment, according to this embodiment as well, instead of the transmission and reception units 63A and 63B in FIG. 6, the transmission and reception unit 137 for wirelessly performing transmission and reception is provided. The transmission and reception unit 137 adopts the antenna section 133.

Then, the status control section 61 controls the light emission timing and the light quantity of the LED 141 via the illumination control section 64B and the LED driver section 65B.

In addition, the status control section 61 drives the CCD 38B via the CCD driver section 66B. The CCD 38B outputs a signal charge photoelectrically converted by the application of the drive signal from the CCD driver section 66B. This output signal is converted into the digital signal by the ADC 67B to be input to the image memory 68B and the brightness detecting section 69B as well as to the status control section 61.

The image memory 68B temporarily stores the digital signal (image data) converted by the ADC 67B. The image data appropriately read from the image memory 68B is sent to the data transmission section 12 similarly to the image data from the image memory 68. Then, the image data is transmitted from the data transmission section 12 via the antenna section 133.

Then, the brightness detecting section 69B detects the mean brightness from the output signals from the ADC 67B to send the data to the status control section 61. The status control section 61 controls the light quantity of the LED 141 or the like via the illumination control section 64B in comparison with the reference value that corresponds to the appropriate brightness.

As described with reference to FIG. 14, when the adjustment cannot be performed within the brightness adjustment range by the LED 141, the adjustment is further performed by adjusting the gain of the CCD 141 to have the appropriate brightness.

It should be noted that according to this embodiment, the operation remote controller 7B of the second embodiment can be used.

According to this embodiment, the distal end side is illuminated with the illumination light from the distal end side of the capsule section 22. In addition to an image picked up in the illumination status, the illumination light is irradiated towards the rear side from the rear end side of the capsule section 22, an image picked up in the illumination status is also displayed on the observation monitor 6, whereby the user (specifically, the surgeon) can observe the image.

In this way, according to this embodiment, as the observation in both the front and back directions can be performed, it becomes easier for the surgeon to conduct the diagnosis or the like on the basis of the endoscopy, and also the operability can be improved. That is, with the structure in which the observation only in one direction can be conducted, to observe the other direction, the surgeon needs an operation for moving the endoscope or the like. However, according to this embodiment, as the observation in both the directions can be conducted, the operation for moving the endoscope is unnecessary for the observation, and also the operability can be improved. Moreover, the observation function can be improved.

Fourth Embodiment

Figure 25:
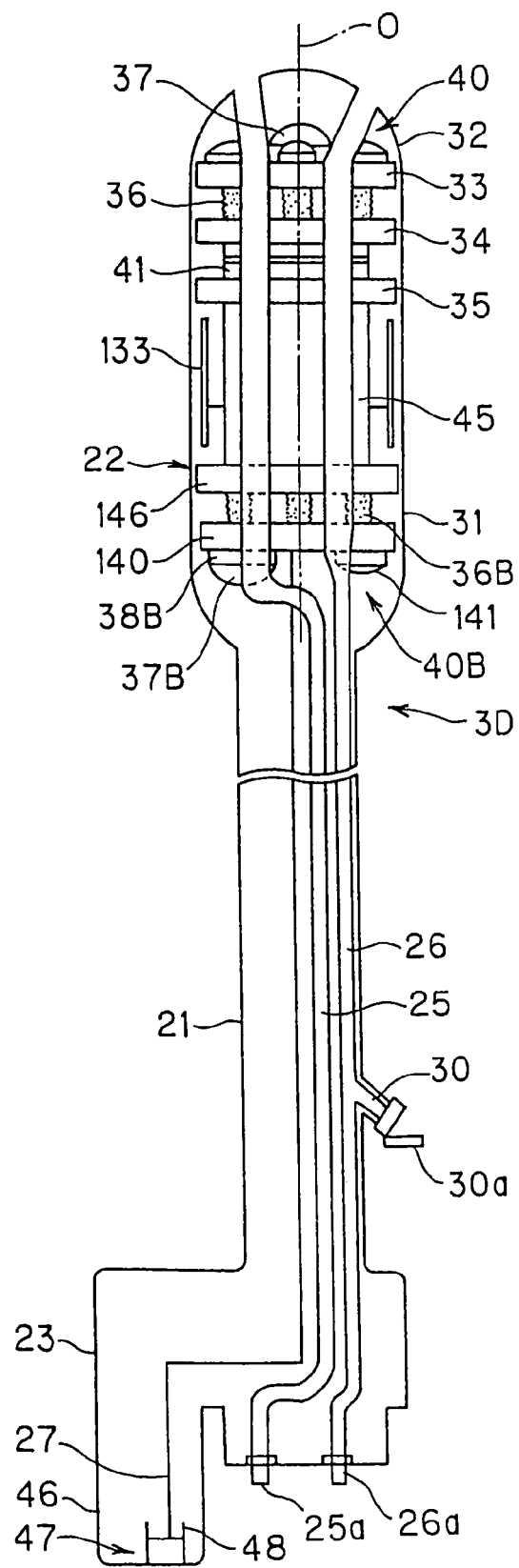
FIG. 25 shows an entire structure of an endoscope according to a fourth embodiment of the present invention.

Next, with reference to FIGS. 25 and 26, a fourth embodiment of the present invention will be described. FIG. 25 shows an endoscope 3D according to the fourth embodiment of the present invention.

The endoscope 3D includes the base member 140 having the rear side illumination and image pickup unit 40B accommodated so as to freely tilt in the inner circumference surface of the exterior body 31, in the endoscope 3C according to the third embodiment shown in FIGS. 23A and 23B.

Then, the base member 140 is supported by a base member 146 that is fixed to the inner circumference surface of the exterior body 31 via a second view field varying articulation actuator 36B. The second view field varying articulation actuator 36B has the same structure as that of the view field varying articulation actuator 36, and is connected to the control circuit 43 via a signal line inside the control unit 45.

The other structure is the same as that of the third embodiment. Then, according to this embodiment, as in the case of the endoscope 3C of the third embodiment, the operation remote controller 7B of the second embodiment can be used.

Figure 26:
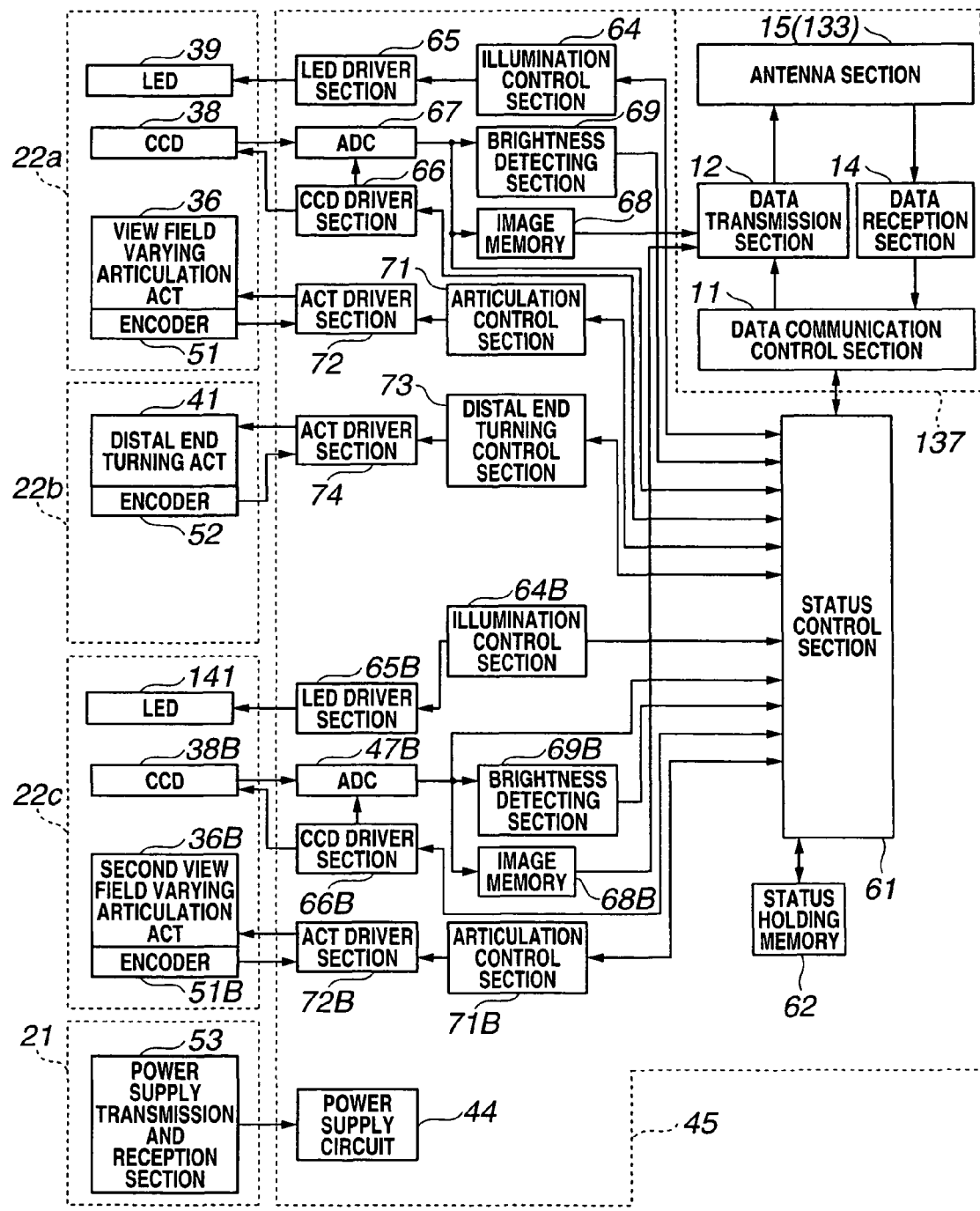
FIG. 26 is a block diagram showing the electrical system configuration of the endoscope.

FIG. 26 shows a structure of an electrical system of the endoscope 3D. The structure shown in FIG. 26 further includes the second view field varying articulation actuator 36B and the encoder 51B for detecting the displacement thereof in the rear end section 22c of the capsule section 22, in the structure of FIG. 24.

The second view field varying articulation actuator 36B and the encoder 51B are connected to the status control section 61 via the actuator driver section 72B and the articulation control section 71B. Then, as in the case of the distal end illumination and image pickup unit 40, the track ball 19 of the operation remote controller 7B is operated, whereby the view field direction of the rear side illumination and image pickup unit 40B can be varied.

According to this embodiment, the operation effect of the third embodiment is attained, and further, at the same time, the direction of the image pickup view field (the observation view field) of the rear side illumination and image pickup unit 40B can be changed to perform the observation, so the operability can be improved. In addition, the observation function can be more improved.

Fifth Embodiment

Next, with reference to FIGS. 27A to 31, a fifth embodiment of the present invention will be described. FIG. 27A shows an endoscope 3E according to the fifth embodiment of the present invention.

The endoscope 3E includes consistency varying actuators 154A and 154B for varying the consistency at plural locations in the insertion tube 21, for example, at a location close to the distal end side and a location at a rear end side, in the endoscope 3D according to the fourth embodiment shown in FIG. 25. The consistency varying actuators 154A and 154B are formed of, for example, EPAM. As the consistency changes due to extension when being applied with a voltage, the consistency at the location where the respective consistency varying actuators 154A and 154B are provided can be varied.

The consistency varying actuators 154A and 154B are connected to the control circuit 43 in the control unit 45 via a signal line inserted in the insertion tube 21. By operating the operation remote controller 7B, the consistency at the part where the consistency varying actuators 154A and 154B are provided can be varied.

Figure 28:
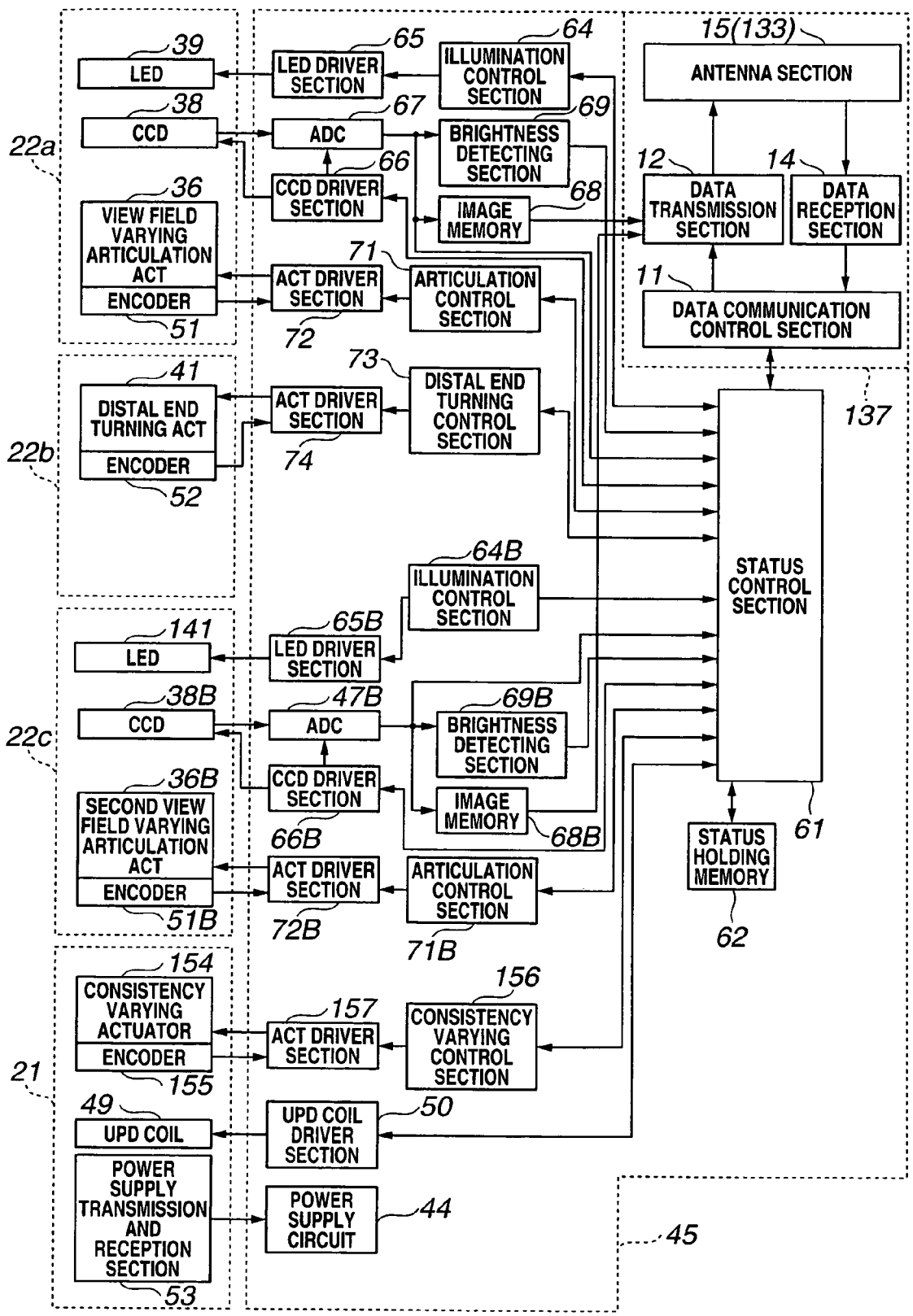
FIG. 28 is a block diagram showing the electrical system configuration of the endoscope.

Also, according to this embodiment, the UPD coils 49 are arranged at a predetermined interval inside the insertion tube 21 as in the case of the first embodiment. Inside the connector 23, the UPD coil driver section 50 is arranged. The coils are connected to the control circuit 43 in the control unit 45. FIG. 28 shows a structure of an electrical system of the endoscope 3E. The structure shown in FIG. 28 includes the consistency varying actuator 154 inside the insertion tube 21 (reference numeral 154 represents 154A and 154B in FIG. 28), in the structure of FIG. 26. The amount of displacement of the consistency varying actuator 154 is detected by an encoder 155.

The status control section 61 controls an actuator driver section 157 via a consistency varying control section 156 and controls for the drive of the consistency varying actuator 154 with use of the actuator driver section 157. The drive amount of the consistency varying actuator 154 is detected by the encoder 155, and accordingly the drive amount is controlled to be a value corresponding to the instructed value.

Figure 29:
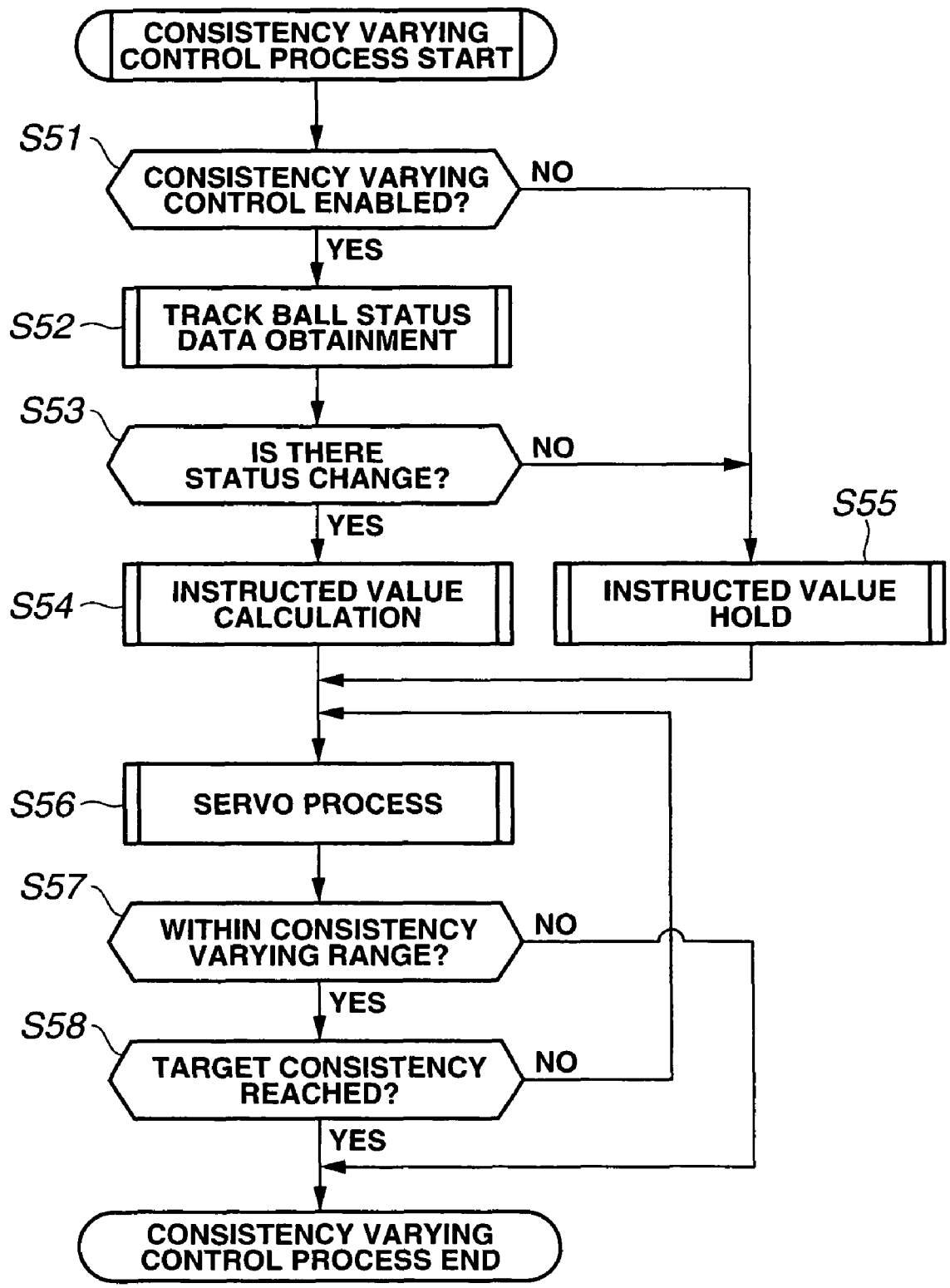
FIG. 29 is a flowchart showing a process content of a consistency varying control.

Next, with reference to FIG. 29, a control process for varying the consistency varying will be described.

When the control process for varying the consistency is started, as shown in Step S51, the status control section 61 judges whether or not the consistency varying control is enabled.

To be specific, as shown in FIG. 11B, from the main menu, the insert section consistency is allocated to one of the function switches SW1 to SW3 (and SW4 and SW5). The status control section 61 judges whether or not the function switch of the insert section consistency is pressed to be enabled (through the status control section 81 of the operation remote controller 7B).

When it is judged that the consistency varying control is not enabled, the flow shifts to Step S55, where the status control section 61 holds the previous instructed value. On the other hand, when it is judged that the consistency varying control is enabled, the flow proceeds to the next Step S52, where the status control section 61 obtains the status data by the operation of the track ball 19.

Then, in the next Step S53, the status control section 61 judges whether or not there is a further status change on the basis of the output of the track ball displacement detecting section 84.

In this case, when it is judged that there is no status change, the process shifts to Step S55, and on the other hand when it is judged that there is a status change, in the next Step S54, the status control section 61 calculates the instructed value corresponding to the rotation direction and the rotation amount of the track ball 19.

After the process in Step S54 or S55, as shown in Step S56, the status control section 61 sends the instructed value via the consistency varying control section 156 to the actuator driver section 157, for performing the servo process on the consistency varying actuator 154.

In other words, the actuator driver section 157 drives the consistency varying actuator 154 so that the target consistency corresponding to the instructed value is obtained on the basis of the instructed value. At that time, the consistency variable status of the consistency varying actuator 154 is detected by the encoder 155, and the actuator driver section 157 drives the consistency varying actuator 154 so that the value detected by the encoder 155 reaches the target consistency.

In Step S57 which is in a midway for performing such a servo process, the consistency varying control section 156 or the status control section 61 judges whether or not this value is in the variable range of the consistency varying actuator 154 on the basis of the actuator driver section 157. When this value is out of the variable range, the consistency varying control process is ended.

Also, in Step S57, when this value is in the variable range of the consistency varying actuator 154, further in the next Step S58, the consistency varying control section 156 or the status control section 61 judges whether or not the value reaches the target consistency. When the value does not reach the target consistency, the flow returns to Step S56 to continue the servo process. In this way, when the value reaches the target consistency, the consistency varying control process is ended.

Then, the UPD unit 76 in the AWS unit 4 (refer to FIG. 8) detects the positions of the UPD coils 49 arranged in the insertion tube 21 of the endoscope 3E by the UPD coil unit 97 to calculate the insertion shape of the insertion tube 21. The shape of the insertion tube 21, in other words, the UPD image is displayed on a display screen of the observation monitor 6.

FIGS. 30A to 30D show a state in which menu screens on the right hand side respectively correspond to UPD images on the left hand side. Consistency parts of the consistency varying actuators 154A and 154B provided at plural positions (two positions in the specific example) in the case in which the user selects and sets the consistency of the consistency varying actuators 154A and 154B from the menu screen are displayed in a color corresponding to the set consistency, whereby the consistency of the part becomes easy to be distinguished.

FIG. 30A shows a display state of the main menu. FIG. 30A shows the case in which the user in this display state selects the insert section consistency variable (by the insertion tube 21). It should be noted that herein the function switch is abbreviated as FN switch.

In this case, the UPD image is displayed in a state in which sections A and B of the consistency varying actuators 154A and 154B are displayed in a color which is not distinguished from sections other than the sections A and B, as immediately before the insert section consistency variable is selected.

As shown in FIG. 30B, when the insert section consistency variable is selected, section ranges regarding the consistency set to the sections A and B of the consistency varying actuators 154A and 154B at the two positions are shown. A consistency setting screen is displayed in which the consistency is set between a flexible state to a rigid state in the sections A and B. The current consistency is indicated by a circle in the respective sections. In this case, the flexible state to the rigid state are displayed in different colors.

Therefore, the corresponding UPD image is displayed in a display color corresponding to the consistency at which the consistency varying actuator is set, with the part of the consistency varying actuator being displayed in color. In the state of FIG. 30B, the consistency section is set close to the flexible state. The sections A and B of the consistency varying actuator 154A and 154B in the UPD image in this case are shown in yellow.

FIG. 30C shows the case in which the consistency of the section B of the consistency varying actuator 154B is set in the vicinity of the center in the state of FIG. 30B, for example. The section B of the consistency varying actuator 154B in the UPD image in this case is shown in green.

Then, FIG. 30D shows the case in which the consistency of the section B of the consistency varying actuator 154B is set to the rigid state (a value showing the rigid state) in the state of FIG. 30B or 30C, for example. The section B of the consistency varying actuator 154B in the UPD image in this case is shown in blue.

By displaying in this way, the user can freely set the consistency of the consistency varying actuators 154A and 154B, and the thus set sections A and B of the consistency varying actuators 154A and 154B are displayed in a display color corresponding to the set consistency. Thus, the user can easily distinguish the consistency of the consistency varying actuators 154A and 154B. It should be noted that as a modified example of the endoscope 3E shown in FIG. 27A, an endoscope 3E' having a structure shown in FIG. 27B may be used. The endoscope 3E' holds the control unit 45 in a front side (surface) of a base member 35B, holds the stator side of the actuator 41B for turning the rear end on the back side of the base member 35B and attaches the base member 146 side to the rotor side thereof, and holds the base member 146 side so as to freely turn, in the endoscope 3E of FIG. 27A.

In this case, the base member 35B is fixed to the inner wall surface of the exterior body 31, and the base member 146 is freely turnably arranged to be fitted into the cylindrical inner periphery surface of the exterior body 31.

Then, the power supply line 28, the signal line connected to the UPD coils 49, and the signal lines connected to the consistency varying actuators 154A and 154B pass along near the center of the insertion tube 21, and also pass along near the center axis O in the capsule section 22. In this case, the base members 140, 146, and 35B include holes (hollow sections) for allowing the power supply line 28 and the like to pass through. Also, the rear end turning actuator 41B composed of an ultrasonic motor or the like includes a hole for allowing the power supply line 28 and the like to pass through.

With the endoscope 3E having such a structure, in addition to the function of observing the target with the rear side illumination and image pickup unit 40B in the case of the endoscope 3E by changing the image pickup view field (the observation view field) with the rear side direction along the center axis O as the reference to an arbitrary direction of up, down, left, and right from, further, the observation can be performed by changing the image pickup view field (the observation view field) through turning the rear side illumination and image pickup unit 40B about the center axis O. Therefore, the observation function can be further improved.

Figure 31:
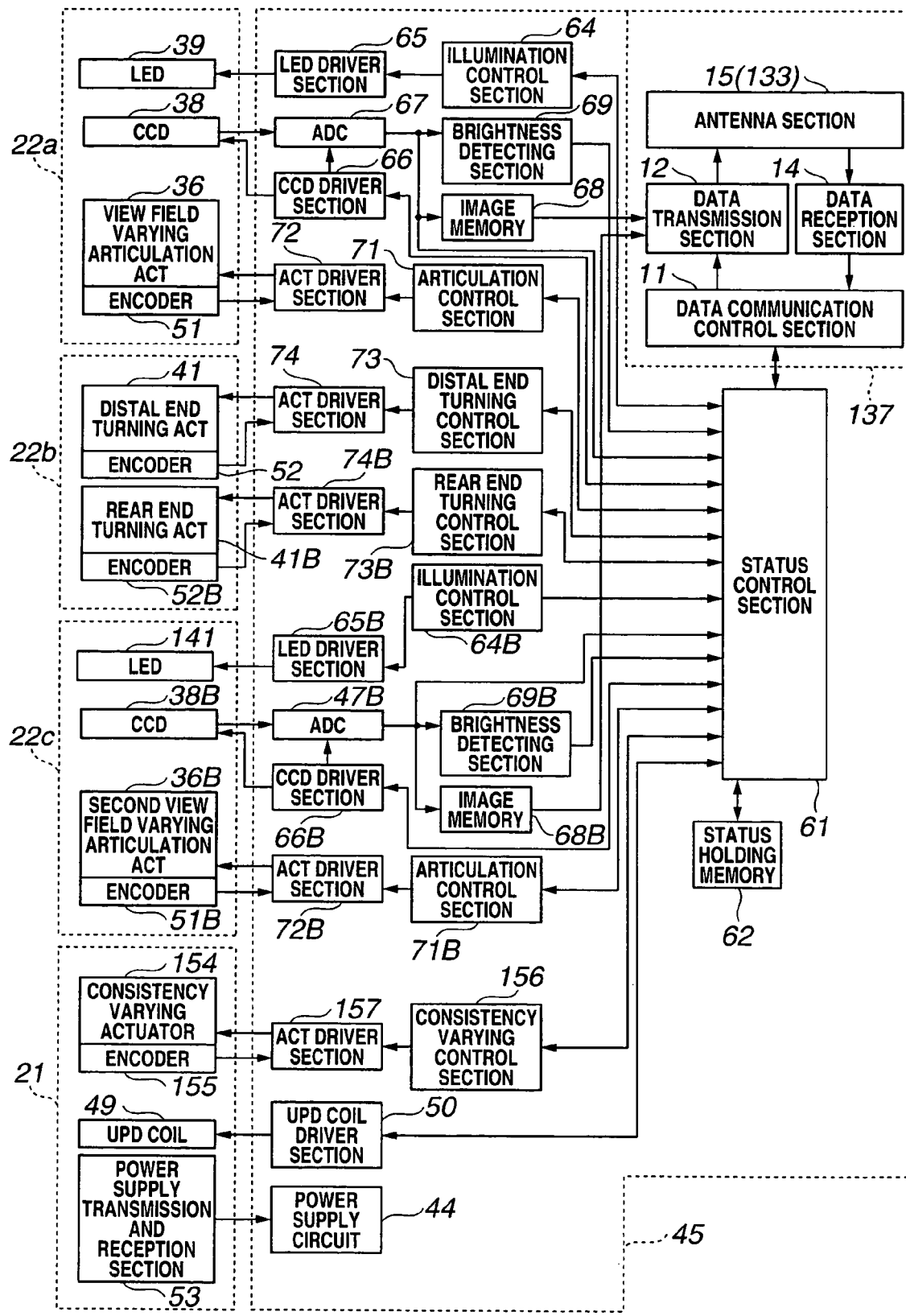
FIG. 31 is a block diagram showing a modification example of the electrical system configuration of the endoscope.

It should be noted that FIG. 31 shows a structure of an electrical system in the case of FIG. 27B. The electrical system of this structure includes a process system for the rear end turning actuator 41B that is the same as the process system for the distal end turning actuator 41, in the structure of FIG. 28.

In other words, the rear end turning actuator 41B and the encoder 52B for detecting the amount of displacement are arranged in the trunk section 22b.

Then, the status control section 61 controls an actuator driver section 74B via a rear end turning control section 73B. With use of the actuator driver section 74B, the drive of the rear end turning actuator 41B is controlled. The drive amount of the rear end turning actuator 41B is detected by the encoder 52B so that the drive amount is controlled to be a value corresponding to the instructed value. The other structure is the same as that of FIG. 28. In this way, according to this modified example, the observation function can be further improved as compared with the case of the fifth embodiment.

It should be noted that according to the above-mentioned embodiments, instead of the track ball 19 in the operation remote controller 7 or 7B, an operation pad shown below may be used.

FIGS. 32A to 32E show a first modified example of an operation remote controller 7C used together with the endoscope 3E according to this embodiment, for example.

It should be noted that FIG. 32A is a side view as seen from the side of the operation remote controller 7C, FIG. 32B is a front view as seen from the right hand side of FIG. 32A, FIG. 32C is a plan view as seen from the top of FIG. 32A, FIG. 32D shows an operation pad 161 provided to the inclined surface Sa in FIG. 32A is set parallel to the inclination direction of the inclined surface Sa, and FIG. 32E shows an operation pad 161' of a modification example in a display mode relevant to FIG. 32D.

The operation remote controller 7C shown in FIGS. 32A to 32C adopts the disc-shaped operation pad 161 instead of the track ball 19 in the operation remote controller 7B shown in FIG. 20A. That is, the operation pad 161 is attached on the inclined surface Sa, so that the center thereof is located on the center axis C bilaterally symmetric to the operation remote controller 7C.

The operation pad 161 includes switches 162a, 162b, 162c, and 162d for an operation instruction for four directions of up, down, left, and right, which are provided at four locations corresponding to up, down, left, and right. The switches 162a, 162b, 162c, and 162d are arranged so as to be bilaterally symmetric.

The other structure is the same as that of FIG. 20A. The operation effect in this case is almost the same as that of FIG. 20A.

In addition, as a first modified example of the operation pad 161, as shown in FIG. 32E, an cross shaped operation pad 161' may be adopted. To the operation pad 161' as well, the switches 162a, 162b, 162c, and 162d for an operation instruction for four directions of up, down, left, and right are provided at four locations corresponding to up, down, left, and right.

FIGS. 33A to 33D show an operation remote controller 7D according to a second modified example. It should be noted that FIG. 33A is a side view as seen from the side of the operation remote controller 7D, FIG. 33B is a front view as seen from the right hand side of FIG. 33A, FIG. 33C is a plan view as seen from the top of FIG. 33A, and FIG. 33D shows operation pads 163A and 163B provided to the inclined surface Sa in FIG. 33A are set parallel to the inclination direction of the inclined surface Sa.

As shown in FIG. 33C, for example, the operation remote controller 7D includes the two operation pads 163A and 163B provided parallel in a vertical direction with respect to the center axis C of the operation remote controller 7C at positions of the track ball 19 in FIG. 20A.

The operation pad 163A includes switches 162a and 162b for up and down directions, and the operation pad 163B includes switches 162c and 162d for left and right directions.

The other structure is the same as that of FIG. 20A.

The operation remote controller 7D of FIGS. 33A to 33C includes the two operation pads 163A and 163B provided parallel in a vertical direction with respect to the center axis C of the operation remote controller 7C. As shown in a third modified example of the operation remote controller 7E shown in FIGS. 34A to 34C, the two operation pads 163C and 163D may be provided in parallel with respect to the center axis C of the operation remote controller 7D. It should be noted that FIG. 34A is a side view as seen from the side of the operation remote controller 7E, FIG. 34B is a front view as seen from the right hand side of FIG. 34A, FIG. 34C is a plan view as seen from the top of FIG. 34A, and FIG. 34D shows the two operation pads 163C and 163D provided to the inclined surface Sa in FIG. 32A are set parallel to the inclination direction of the inclined surface Sa in FIG. 34A.

In the case of using the operation remote controller 7C to 7E as well, almost the same operability can be ensured.

According to the first to fifth embodiments described above, the endoscopy can be smoothly conducted in such a manner that airing and watering are performed via the duct line provided in the tube body to clean the image pickup window to prevent reduction in the image pickup function or the endo-therapy product is inserted to perform the treatment.

Sixth Embodiment

Figure 35:
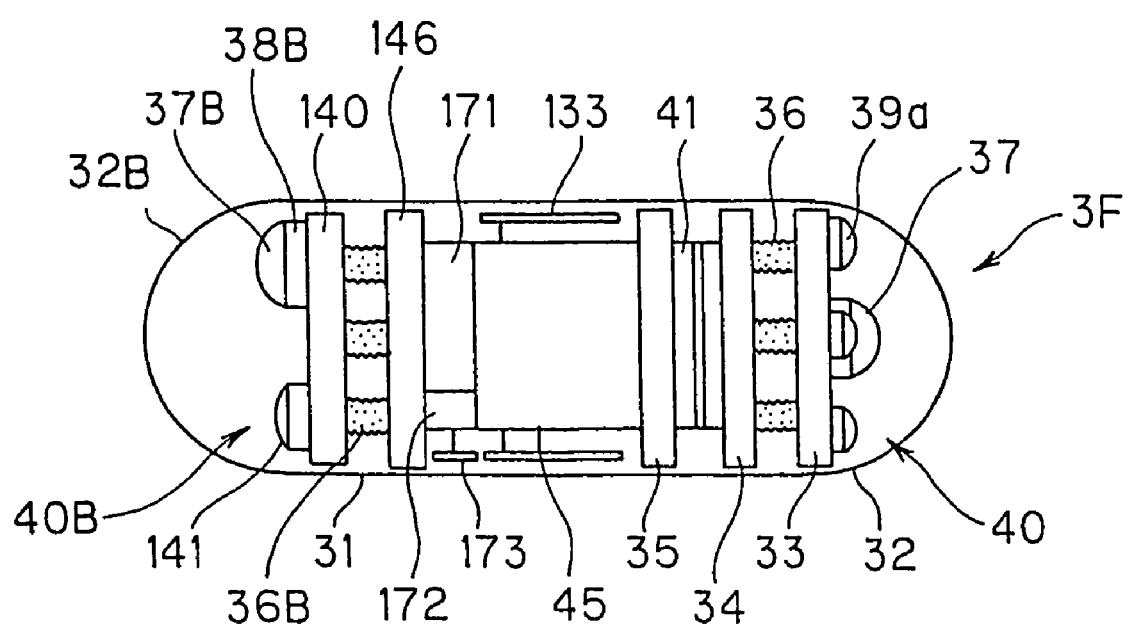
FIG. 35 shows an endoscope according to a sixth embodiment of the present invention.

Next, with reference to FIG. 35, a sixth embodiment of the present invention will be described. FIG. 35 shows an endoscope 3F according to the sixth embodiment of the present invention.

The endoscope 3F does not include, for example, the insertion tube 21 in the endoscope 3D of FIG. 25. According to the structure, the rear end side of the exterior body 31 only includes the capsule section 22 formed of hemispheric (dome shaped) transparent cover 32B similarly to the transparent distal end cover 32 on the distal end side.

The capsule section 22 has built therein a battery 171 functioning as a rechargeable secondary battery, a charging circuit 172 for recharging the battery 171, and a noncontact feeding coil 173 that is connected to the charging circuit 172 and receives an alternating current power from the outside to supply the charging circuit 172 with the alternating current power in a noncontact manner.

In other words, the battery 171 is built in the water tight capsule shaped exterior body 31 for recharging in a noncontact or contactless manner.

The endoscope 3F according to this embodiment has a structure of being separated from the insertion tube 21 to which the air water duct line 25 and the suction duct line 26 are provided and having no duct line in communication with the air water duct line 25 and the suction duct line 26.

In this way, in the case of the endoscope 3F without having the insertion tube 21 as well, it is possible to set such that by operating the operation remote controller 7B or the like, the view field direction of the illumination and image pickup unit 40 provided inside the endoscope 3F is changed to observe the desired direction.

In addition, the inclination angle on the rear side illumination and image pickup unit 40B side is changed, thereby making it also possible to set the observation direction on the rear side illumination and image pickup unit 40B side to the desired direction. In this way, according to this embodiment too, the satisfactory observation function can be ensured.

It should be noted that the structure on the rear side illumination and image pickup unit 40B side according to this embodiment may have almost the same structure as the illumination and image pickup unit 40 side. For example, an objective lens 37B and the CCD 38B are arranged in the center of the disc-shaped base member 140, the plural white LEDs 141 or the LEDs for emitting lights in red, green, and blue are arranged around there, and the infrared LED is further arranged, whereby illumination and image pickup may be performed in an infrared mode.

Also, this embodiment is applied to the endoscope 3D of the fourth embodiment, but this embodiment may be applied to the modification example of the fifth embodiment, in other words, the endoscope 3E' of FIG. 27B. In this case, the inclination angle on the rear side illumination and image pickup unit 40B side can be changed and at the same time the observation can be conducted while the turning angle is changed, whereby the observation function can be significantly improved.

It should be noted that the view field varying articulation actuator 36 or the like is not limited to the case of the electroconductive polymer artificial muscle (EPAM), and the view field varying articulation actuator may be formed by laminating piezoelectric element in a rod shape or the like. Moreover, as the distal end turning actuator 41 and the rear end turning actuator 41B, the ultrasonic motor, another motor, or the like can be used.

It should be noted that the view field direction as the reference may be set in a direction inclined by a certain angle from the direction of the center axis O so that the view field direction can be changed only by the distal end turning actuator 41 or the rear end turning actuator 41B.

It should be noted that other embodiments structured by combining parts of the above-mentioned embodiments and the like are also within the scope of the present invention.

What is claimed is:

1. An endoscope, comprising:
   a container body;
   an illumination section and an image pickup section provided to the container body;

a tube body integrally provided to the container body;

a hollow duct line passing in the tube body and including a distal end which penetrates through the container body and has an opening on an outer surface of the container body; and a first and second illumination and image pickup units each of which includes the illumination section and the image pickup section, the first and second illumination and image pickup units being accommodated to have opposite reference view field directions in the container body and are respectively freely tilted in an arbitrary direction within predetermined inclination angles from the reference view field direction.

2. The endoscope according to claim 1, wherein the duct line includes at least one of an air water duct line for performing airing and watering and a suction duct line for performing suction, which are inserted in the tube body.

3. The endoscope according to claim 2, further comprising on a base end side of the suction duct line, an endo-therapy product insert port for allowing insertion of an endo-therapy product.

4. The endoscope according to claim 3, wherein the container body accommodates a turning section for freely turning a distal end side of the container body, and when an endo-therapy product is inserted from the endo-therapy product insert port into the suction duct line, a direction of the endo-therapy product protruding from the port can be variably controlled.

5. The endoscope according to claim 2, further comprising on a base end of the tube body, connectors for detachably attaching the air water duct line and the suction duct line to an external air water section and an external suction section, respectively.

6. The endoscope of claim 1, further comprising a view field direction varying section which is capable of varying the view field direction.

7. The endoscope according to claim 6, wherein the view field direction varying section can tilt a board of the illumination and image pickup unit in an arbitrary direction of up, down, left, and right.

8. The endoscope according to claim 1, wherein the container body accommodates a turning section for freely turning a distal end side of the container body.

9. The endoscope according to claim 1, wherein the image pickup section includes a high sensitivity image pickup element having a gain varying function inside the image pickup element.

10. The endoscope according to claim 1, wherein the tube body has a plurality of position detecting elements arranged along a longitudinal direction of the tube body.

11. The endoscope according to claim 1, wherein the container body accommodates a power supply circuit, and the power supply circuit is supplied with an alternating current power via a contactless electrical connector.

12. The endoscope according to claim 1, wherein the endoscope performs communication with remote operation sections which are separately provided from the endoscope for performing various operation instructions of remote operations for the endoscope via a signal transmission section that transmits a signal.

13. The endoscope according to claim 12, wherein the remote operation section includes a grasping section grasped by a user, and the grasping section is provided with a plurality of switches for performing various operation instructions to the endoscope, the switches being bilaterally symmetrically arranged.

14. The endoscope according to claim 1, further comprising consistency varying sections at a plurality of positions on the tube body, which are capable of varying a consistency of the tube body.

15. The endoscope according to claim 1, wherein the illumination section includes a visible area illumination section for performing illumination in a visible area and a special wavelength area illumination section for performing illumination in a special wavelength area other than the visible area.

16. The endoscope according to claim 1, wherein a distal end side of the container body is in a dome shape.

17. The endoscope according to claim 1, further comprising a control process section for performing a control process at least for the image pickup section.

18. The endoscope according to claim 17, wherein the control process section includes a device model information on the endoscope as control information for the control process.

19. The endoscope according to claim 18, wherein the device model information on the endoscope includes at least one of type information on a solid-state image pickup element structuring the image pickup section, and insert section length information.

20. The endoscope according to claim 17, wherein the control process section includes information unique to the endoscope as control information for performing the control process.

21. The endoscope according to claim 20, wherein the information unique to the endoscope includes at least one of information on endoscope use time, and information on the number of times the endoscope has been washed.

22. An endoscope device, comprising:

an endoscope comprising:

a container body including an illumination section and an image pickup section;

a tube body that is integrally provided to the container body and has a hollow duct line inserted therein having at least an opening at one end on an outer surface of the container body; and a first and second illumination and image pickup units each of which includes the illumination section and the image pickup section; and a remote operation unit that is separately provided from the endoscope and includes an operation section for performing an instruction operation for at least the image pickup section, the first and second illumination and image pickup units being accommodated to have opposite reference view field directions in the container body and are respectively freely tilted in an arbitrary direction within predetermined inclination angles from the reference view field direction.

* * * * *